US009840470B2

(12) United States Patent
He et al.

(10) Patent No.: US 9,840,470 B2
(45) Date of Patent: Dec. 12, 2017

(54) TARGETING GLI PROTEINS IN HUMAN CANCER BY SMALL MOLECULES

(71) Applicant: The Regents of the University of California, Oakland, CA (US)

(72) Inventors: Biao He, Foster City, CA (US); Michael Mann, San Francisco, CA (US); David M. Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/761,230

(22) PCT Filed: Jan. 22, 2014

(86) PCT No.: PCT/US2014/012466
§ 371 (c)(1),
(2) Date: Jul. 15, 2015

(87) PCT Pub. No.: WO2014/116651
PCT Pub. Date: Jul. 31, 2014

(65) Prior Publication Data
US 2015/0361048 A1 Dec. 17, 2015

Related U.S. Application Data

(60) Provisional application No. 61/755,878, filed on Jan. 23, 2013.

(51) Int. Cl.
| | |
|---|---|
| *C07D 231/06* | (2006.01) |
| *A61K 31/415* | (2006.01) |
| *A61K 45/06* | (2006.01) |
| *A61K 31/4439* | (2006.01) |
| *A61K 31/517* | (2006.01) |
| *A61K 31/519* | (2006.01) |
| *A61K 31/5377* | (2006.01) |
| *A61K 33/24* | (2006.01) |
| *C07D 231/14* | (2006.01) |
| *C07D 409/04* | (2006.01) |
| *A61K 31/4155* | (2006.01) |

(52) U.S. Cl.
CPC .......... *C07D 231/06* (2013.01); *A61K 31/415* (2013.01); *A61K 31/4155* (2013.01); *A61K 31/4439* (2013.01); *A61K 31/517* (2013.01); *A61K 31/519* (2013.01); *A61K 31/5377* (2013.01); *A61K 33/24* (2013.01); *A61K 45/06* (2013.01); *C07D 231/14* (2013.01); *C07D 409/04* (2013.01)

(58) Field of Classification Search
None
See application file for complete search history.

(56) References Cited

U.S. PATENT DOCUMENTS 7,714,014 B2 * 5/2010 He .................. C07D 231/06
514/403
2014/0303160 A1 10/2014 He et al.

FOREIGN PATENT DOCUMENTS

| | | |
|---|---|---|
| JP | 07041459 | 10/1995 |
| JP | 2010070514 | 4/2010 |
| WO | 2007067814 | 6/2007 |
| WO | 2010032200 | 3/2010 |
| WO | WO 2010094009 | 8/2010 |
| WO | 2013013190 | 1/2013 |

OTHER PUBLICATIONS

Pinedo et al. (2000).*
McMahon et al. (2000).*
Vippagunta et al. (2001).*
Wolff et al. (1996) Banker et al. (1996).*
Cancer Drug Design and Discovery Neidle, Stephen, ed. (Elsevier/Academic Press, 2008) pp. 427-431.*
Mahindroo et al. J.Med. Chem. 2009, 52, 4277-4287.*
Mahindroo et al., (2009) "Structure-Activity Relationships and Cancer-Cell Selective Toxicity of Novel Inhibitors of Glioma-Associated Oncogene Homologue 1 (Gli1) Mediated Transcription," J. Med. Chem. 52: 4277-4287.
Patani et al., (1996) "Bioisosterism: A Rational Approach in Drug Design," Chem. Rev. 96: 3147-3176.
Pirkle et al., "A widely Useful Chiral Stationary Phase for the High-Performance Liquid Chromatography Separation of Enantiomers," J. Am. Chem. Soc., 103:3964-3966 (1981).
Tremblay et al., "Recent patents for hedgehog pathway inhibitors for the treatment of malignancy," Expert Opinion on Therapeutic Patents, 19(8): 1039-1056 (2009).

* cited by examiner

*Primary Examiner* — Paul V Ward
(74) *Attorney, Agent, or Firm* — Rudy J. Ng; Bozicevic, Field & Francis LLP

(57) ABSTRACT

The present disclosure provides compositions, pharmaceutical preparations and methods for the diagnosis and treatment of cancers expressing a GLI polypeptide. The disclosed compositions and pharmaceutical preparations may comprise one or more pyrazolyl-containing compounds, or an analog or derivative thereof.

17 Claims, 25 Drawing Sheets

| Cancer | Cell Lines | #4 | P1 | P2 | Cancer | Cell Lines | #4 | P1 | P2 |
|---|---|---|---|---|---|---|---|---|---|
| Melanoma | Clau6 | 2.27 | 8.67 | 1.58 | Mesothelioma | H2052 | 1.59 | 12.81 | 0.87 |
| | SK-Mel30 | 4.27 | 8.19 | 2.93 | | REN | 1.37 | 5.33 | 0.75 |
| | LOX | 1.52 | 11.03 | 0.81 | | H2452 | 4.09 | 8.21 | 2.50 |
| | MelJuso | 0.96 | 8.12 | 0.49 | | 211H | 4.78 | 13.31 | 2.59 |
| | Mel144 | 1.15 | 6.27 | 0.69 | | H290 | 1.11 | 4.93 | 0.65 |
| | Mel202 | 3.54 | 6.08 | 1.94 | | MS1 | 2.09 | 8.11 | 0.88 |
| Lung | H322 | 2.55 | 9 | 1.34 | Colon | COLO-201 | 6.79 | 8.25 | 5.20 |
| | H460 | 2.2 | 6.55 | 1.36 | | Caco-2 | 1.55 | 6.72 | 1.20 |
| | A549 | 2.87 | 8.14 | 1.33 | | DLD-1 | 1.9 | | 0.80 |
| | H1703 | 5.79 | 9.01 | 3.96 | | HCT116 | 13.50 | | 6.50 |
| | H1299 | 5.03 | 10.78 | 3.3 | Pancreatic | CFPAC1 | 1.22 | 9.41 | 0.69 |
| | H1975 | 4.93 | 13.99 | 2.93 | | ASPC-1 | | | 2.80 |
| | H441 | 6.6 | 10.67 | 5.29 | | Panc 02.13 | | | 6.10 |
| | H522 | 0.95 | 7.59 | 0.54 | | PANC-1 | | | 6.80 |
| | H2170 | 16.27 | 17.97 | 13.17 | Prostate | DU145 | 3.17 | 6.02 | 2.54 |
| | H838 | 2.89 | 12.04 | 1.38 | | | | | |
| | A427 | 1.1 | 7.08 | 0.59 | | | | | |

FIG. 18

TARGETING GLI PROTEINS IN HUMAN CANCER BY SMALL MOLECULES

CROSS-REFERENCE TO RELATED APPLICATIONS

This application is a U.S. national stage application of international application PCT/US2014/012466, filed Jan. 22, 2014, which application claims priority pursuant to 35 U.S.C. §119(e) to the filing date of U.S. Provisional Patent Application Ser. No. 61/755,878 filed on Jan. 23, 2013, the disclosures of each of which are herein incorporated by reference.

INTRODUCTION

Hedgehog (Shh or Hh), WNT, FGF and BMP signaling pathways network together during embryogenesis, tissue regeneration, and carcinogenesis. Aberrant activation of Hh signaling pathways leads to pathological consequences in a variety of human tumors. Hedgehogs are secreted glycoproteins that initiate Hh signal transduction by binding to a transmembrane protein complex comprising PATCHED1 (ptch1) and SMOOTHENED (smo) and eliciting a cascade of cytoplasmic signal transduction events, including the inhibition of a protein kinase A that leads to the transcription of the GLI zinc-finger transcription factors. The GLI family of zinc-finger transcription factors then translate the extracellular Hh-stimulus into defined transcriptional programs in a context-dependent and cell-type specific manner (Ruiz I Altaba et al., 2002, *Nat. Rev. Cancer* 2:361-72).

Several proteins, including GLI proteins, are involved in mediating Hh signaling (Katoh and Katoh, 2005, *Cancer Biol. Ther.* 4:1050-4). Vertebrates have at least three distinct GLI proteins, GLI (also referred to as GLI1), GLI2, and GLI3. These proteins are members of the GLI family of zinc finger transcription factors and share a highly conserved $C_2$—$H_2$ zinc finger domain (having five zinc finger DNA-binding motifs) with *Drosophila Cubitus interruptus* (Ci) and the *Caenorhabditis elegans* sex-determining gene tra-1 (Hui et al., 1994, *Dev. Biol.* 162:402-13).

Though much is known about Hh-signaling in *Drosiphila* and murine development, understanding of the molecular mechanisms and tumorigenic programs that are activated in response to Hh-signaling and GLI activity in human cancer is still very limited. A common property of Hh-associated cancers is the elevated expression level of one or more GLI proteins.

SUMMARY

The present disclosure relates generally to compositions and methods of inhibiting tumorigenesis, tumor growth and tumor survival. The compositions comprise small molecule compounds inhibiting Hedgehog and GLI signaling pathways. The compositions find use in treating cancers wherein GLI proteins are overexpressed.

The embodiments provide compounds, pharmaceutical compositions, kits and methods useful for the detection and treatment of a number of cancers wherein GLI protein is overexpressed. Such cancers include lung cancer, NSCLC, breast cancer, colon cancer, mesothelioma, melanoma, sarcoma, prostate cancer, ovarian cancer, renal cancer, esophageal cancer, gastric cancer, hepatocellular cancer, nasopharyngeal cancer, pancreatic cancer, glioma, and others.

Aspects of the present disclosure include a compound of formula (I):

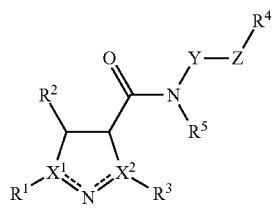

wherein
each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C;
$R^1$ is aryl or substituted aryl;
$R^2$ is selected from aryl, substituted aryl, heteroaryl, substituted heteroaryl, and alkyl;
$R^3$ is aryl or substituted aryl;
Y is a direct bond or $C_1$-$C_4$ alkyl;
Z is $C_1$-$C_4$ alkyl or aryl;
$R^4$ is —OH; and
$R^5$ is hydrogen or $C_1$-$C_6$ alkyl;
and salts, hydrates, solvates, stereoisomers and prodrugs thereof.

In some embodiments of the compound, $X^1$ is N and $X^2$ is C.
In some embodiments of the compound, $X^1$ is C and $X^2$ is N.
In some embodiments of the compound, $R^1$ is aryl.
In some embodiments of the compound, $R^2$ is selected from aryl, substituted aryl, heteroaryl, and alkyl.
In some embodiments of the compound, $R^2$ is selected from heteroaryl and alkyl.
In some embodiments of the compound, $R^3$ is aryl.
In some embodiments of the compound, $R^3$ is substituted aryl.
In some embodiments of the compound, $R^5$ is hydrogen.
In some embodiments of the compound, Y is $C_1$-$C_4$ alkyl and Z is $C_1$-$C_4$ alkyl.
In some embodiments of the compound, Y is $C_1$-$C_4$ alkyl and Z is $C_1$-$C_4$ alkyl, such that Y and Z form —(CH$_2$)$_3$—C(CH$_3$)$_2$—CH$_2$—.
In some embodiments of the compound, Y is $C_1$-$C_4$ alkyl and Z is aryl.
In some embodiments of the compound, Y is $C_1$-$C_4$ alkyl and Z is aryl, such that Y and Z form

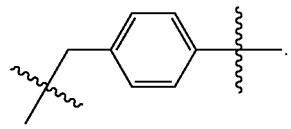 [SMILES: *Cc1ccc(*)cc1]

In some embodiments of the compound, $R^1$ is aryl, $R^2$ is heteroaryl, and $R^3$ is aryl.
In some embodiments of the compound, $R^1$ is aryl, $R^2$ is alkyl, and $R^3$ is substituted aryl.
In some embodiments of the compound, $R^1$ is aryl, $R^2$ is aryl, and $R^3$ is aryl.
In some embodiments of the compound, $R^1$ is aryl, $R^2$ is substituted aryl, and $R^3$ is substituted aryl.
In some embodiments of the compound, the compound is 1,3-diphenyl-5-thiophen-3-yl-4,5-dihydro-1H-pyrazole-4-carboxylic acid (5-hydroxy-4,4-dimethyl-pentyl)-amide, having the structure:

(Compound 1)

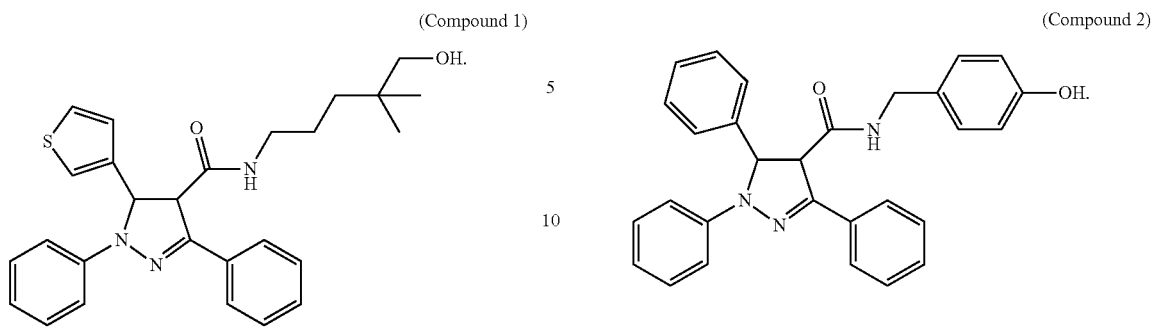

In some embodiments of the compound, the compound is 1,3-diphenyl-5-thiophen-3-yl-4,5-dihydro-1H-pyrazole-4-carboxylic acid (5-hydroxy-4,4-dimethyl-pentyl)-amide, having the structure:

(Compound 1)

In some embodiments of the compound, the compound is 3-(4-fluoro-phenyl)-1-phenyl-5-propyl-4,5-dihydro-1H-pyrazole-4-carboxylic acid (5-hydroxy-4,4-dimethyl-pentyl)-amide, having the structure:

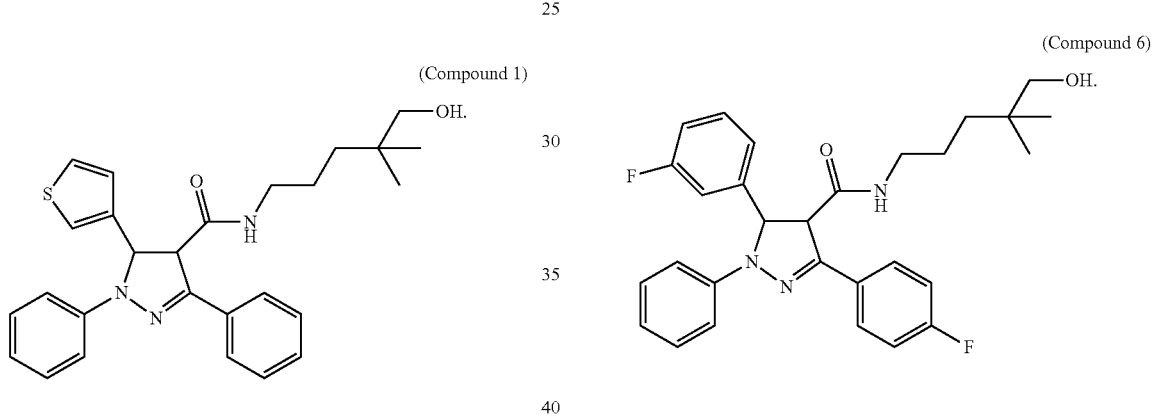

In some embodiments of the compound, the compound is 1,3,5-triphenyl-4,5-dihydro-1H-pyrazole-4-carboxylic acid 4-hydroxy-benzylamide, having a structure:

(Compound 2)

In some embodiments of the compound, the compound is 3-(4-fluoro-phenyl)-5-(3-fluoro-phenyl)-1-phenyl-4,5-dihydro-1H-pyrazole-4-carboxylic acid (5-hydroxy-4,4-dimethyl-pentyl)-amide, having the structure:

(Compound 6)

In some embodiments of the compound, the compound is selected from:

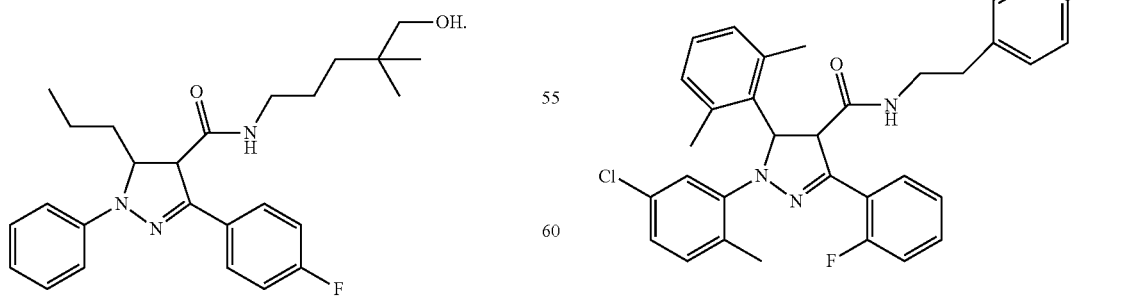

(1-(5-chloro-2-methyl-phenyl)-5-(2,6-dimethyl-phenyl)-3-(2-fluoro-phenyl)-4,5-dihydro-1H-pyrazole-4-carboxylic acid [2-(4-hydroxy-phenyl)-ethyl]-amide, Compound 3), and

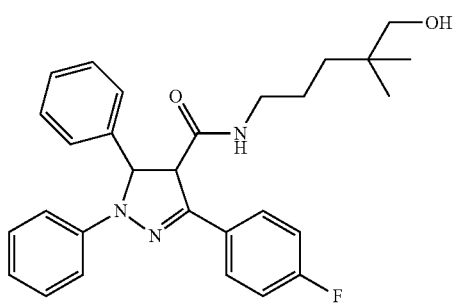 [SMILES: CC(C)(CO)CCCNC(=O)C1C(c2ccc(F)cc2)=NN(c2ccccc2)C1c1ccccc1]

(3-(4-fluoro-phenyl)-1,5-diphenyl-4,5-dihydro-1H-pyrazole-4-carboxylic acid (5-hydroxy-4,4-dimethyl-pentyl)-amide, Compound 5).

Aspects of the present disclosure include a pharmaceutical composition that includes a compound of formula (I) as described above and a pharmaceutically acceptable carrier.

Aspects of the present disclosure include a pharmaceutical composition that includes a compound of formula (I) as described above and a chemotherapeutic agent.

Aspects of the present disclosure include a pharmaceutical composition that includes a compound of formula (I) as described above and a therapeutic agent selected from erlotinib, pemetrexed, LY294002, SB431542, and cisplatin.

The embodiments also provide methods for using the compounds of formula (I). In a certain embodiment, a method for treating a subject suffering from a cancerous condition is provided. The method comprises the step of administering to the subject a therapeutically effective amount of a compound of formula (I) or a pharmaceutical composition that includes a compound of formula (I), where the cancerous condition is characterized by expressing a GLI polypeptide and where the step of administering results in the treatment of the subject.

Further, the embodiments provide for a compound of formula (I) or a pharmaceutical composition that includes a compound of formula (I) for use in medical therapy. Further, the embodiments provide for a compound of formula (I) or a pharmaceutical composition that includes a compound of formula (I) for use in the treatment of a cancer. Further, the embodiments provide for the use of a compound of formula (I) or a pharmaceutical composition that includes a compound of formula (I) in the manufacture of a medicament for treatment of a cancer.

BRIEF DESCRIPTION OF THE FIGURES

FIG. 18 shows cell toxicity $IC_{50}$ values (µM) for Gli inhibitor Compound 4 and each of its two purified enantiomers (P1 and P2) for various cancer cell lines, according to embodiments of the present disclosure.

DETAILED DESCRIPTION

Figure 1:
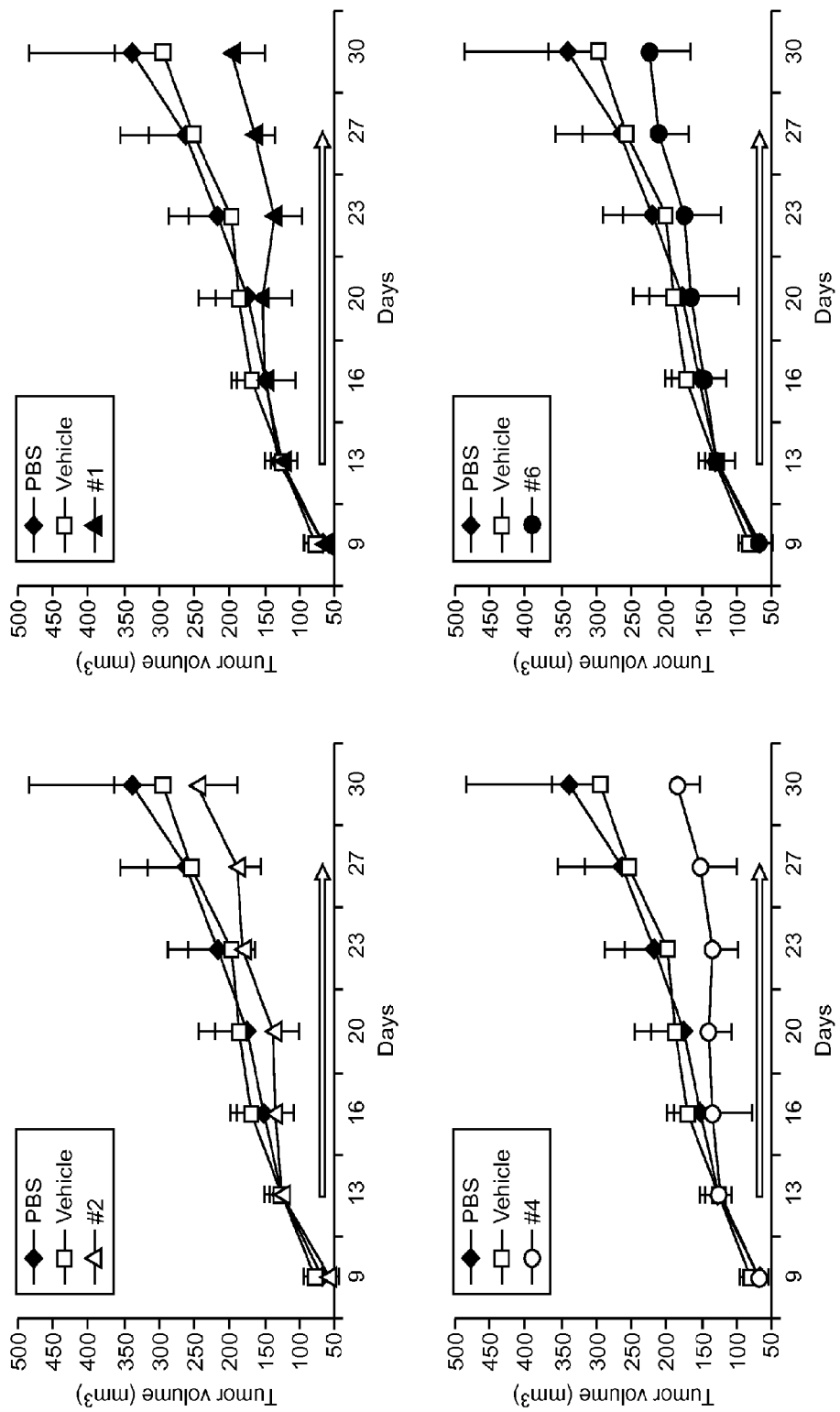
FIG. 1 shows an in vivo efficacy study of Compounds 1, 2, 4, and 6 using a Mouse Xenograft Model (melanoma MelJuso), according to embodiments of the present disclosure. Tumor weight significantly decreased after treatment with the administered compounds. Results are the means±SD (error bars). Arrow indicates the period of injection.

Aspects of the present disclosure include compounds, pharmaceutical compositions, kits and methods useful for the detection and treatment of a number of cancers wherein GLI protein is overexpressed. The compositions comprise small molecule compounds inhibiting Hedgehog and GLI signaling pathways.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "and", and "the" include plural referents unless the context clearly dictates otherwise. Thus, for example, reference to a "compound" includes a plurality of such compounds and equivalents thereof known to those skilled in the art, and so forth.

Terms

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "alkyl" refers to a straight or branched chain hydrocarbon radical, and can include di- and multivalent radicals, having the number of carbon atoms designated (i.e., $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

As used herein, the term "alkenyl" refers to an unsaturated alkyl group one having one or more double bonds. Examples of alkenyl groups include vinyl, 2-propenyl, crotyl, 2-isopentenyl, 2-(butadienyl), 2,4-pentadienyl and 3-(1,4-pentadienyl), and the higher homologs and isomers.

As used herein, the term "alkynyl" refers to an unsaturated alkyl group one having one or more triple bonds. Examples of alkynyl groups include ethynyl (acetylenyl), 1-propynyl, 1- and 2-butyryl, and the higher homologs and isomers.

As used herein, the term "aryl" refers to a polyunsaturated, aromatic, hydrocarbon substituent having 5-12 ring members, which can be a single ring or multiple rings (up to three rings) which are fused together or linked covalently. Non-limiting examples of aryl groups include phenyl, 1-naphthyl, 2-naphthyl, 4-biphenyl, and benzyl. Other aryl groups are also useful in the embodiments.

As used herein, the term "cycloalkyl" refers to a saturated cyclic hydrocarbon having 3 to 15 carbons, and 1 to 3 rings that can be fused or linked covalently. Cycloalkyl groups useful in the embodiments include, but are not limited to, cyclopentyl, cyclohexyl, cycloheptyl and cyclooctyl. Bicycloalkyl groups useful in the embodiments include, but are not limited to, [3.3.0]bicyclooctanyl, [2.2.2]bicyclooctanyl, [4.3.0]bicyclononane, [4.4.0]bicyclodecane (decalin), spiro [3.4]octanyl, spiro[2.5]octanyl, and so forth.

As used herein, the term "cycloalkenyl" refers to an unsaturated cyclic hydrocarbon having 3 to 15 carbons, and 1 to 3 rings that can be fused or linked covalently. Cycloalkenyl groups useful in the embodiments include, but are not limited to, cyclopentenyl, cyclohexenyl, cycloheptenyl and cyclooctenyl. Bicycloalkenyl groups are also useful in the embodiments.

As used herein, the term "halogen" refers to the elements including fluorine (F), chlorine (Cl), bromine (Br) and iodine (I).

As used herein, the term "heteroaryl" refers to a polyunsaturated, aromatic, hydrocarbon substituent having 5-12 ring members, which can be a single ring or multiple rings (up to three rings) which are fused together or linked covalently, and which has at least one heteroatom in the ring, such as N, O, or S. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Additional heteroaryl groups useful in the embodiments include pyridyl N-oxide, tetrazolyl, benzofuranyl, benzothienyl, indazolyl, or any of the radicals substituted, especially mono- or di-substituted.

As used herein, the term "heterocyclyl" refers to a saturated cyclic hydrocarbon having 3 to 15 ring members, and 1 to 3 rings that can be fused or linked covalently, and which has at least one heteroatom in the ring, such as N, O, or S. Additionally, a heteroatom can occupy the position at which the heterocycle is attached to the remainder of the molecule. Examples of heterocyclyl groups include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

As used herein, the term "stereoisomers" refers to compounds of the embodiments that possess asymmetric carbon atoms (optical centers) or double bonds. The racemates, diastereomers, enantiomers, geometric isomers (i.e., cis/trans isomers) and individual stereoisomers are all intended to be encompassed within the scope of the embodiments.

A "label" or a "detectable moiety" is a composition detectable by spectroscopic, photochemical, biochemical, immunochemical, chemical, or other physical means. For example, useful labels include $^3$H, $^{125}$I, $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a small molecule compound. The labels may be incorporated into a compound at any position.

The term "pharmaceutically acceptable" refers to compositions that are physiologically tolerable and do not typically produce an allergic or similar untoward reaction when administered to a subject, such as a human subject. For example, the term "pharmaceutically acceptable" also can mean approved by a regulatory agency of a Federal or state government or listed in the U.S. Pharmacopeia or other generally recognized pharmacopeia for use in animals, such as in humans.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

As used herein, the term "prodrug" refers to compounds that readily undergo chemical changes under physiological conditions to provide the compounds of the embodiments. Additionally, prodrugs can be converted to the compounds of the embodiments by chemical or biochemical methods in an ex vivo environment. For example, prodrugs can be slowly converted to the compounds of the embodiments when placed in a transdermal patch reservoir with a suitable enzyme or chemical reagent.

As used herein, the term "salts" refers to salts of compounds which are prepared with relatively nontoxic acids or bases, depending on the substituents found on the compounds described herein. When compounds of the embodiments contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the embodiments contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the embodiments contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the embodiments.

As used herein, the term "solvates" refers to compounds of the embodiments that are complexed to a solvent. Solvents that can form solvates with the compounds of the embodiments include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

"Substituted" refers to a group in which one or more hydrogen atoms are each independently replaced with the same or different substituent(s). Typical substituents include, but are not limited to, —X, —$R^{14}$, —O—, =O, —$OR^{14}$, —$SR^{14}$, —$S^-$, =S, —$NR^{14}R^{15}$, =NR, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{14}$, —$OS(O_2)O^-$, —$OS(O)_2R^{14}$, —$P(O)(O^-)_2$, —$P(O)(OR^{14})(O^-)$, —$OP(O)(OR^{14})(OR^{15})$, —$C(O)R^{14}$, —$C(S)R^{14}$, —$C(O)OR^{14}$, —$C(O)NR^{14}R^{15}$, —$C(O)O^-$, —$C(S)OR^{14}$, —$NR^{16}C(O)NR^{14}R^{15}$, —$NR^{16}C(S)NR^{14}R^{15}$, —$NR^{17}C(NR^{16})NR^{14}R^{15}$ and —$C(NR^{16})NR^{14}R^{15}$, where each X is independently a halogen, and where "$R^{14}$", "$R^{15}$", "$R^{16}$", and "$R^{17}$" are independently hydrogen, alkyl, substituted alkyl, aryl, arylalkyl, cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{18}R^{19}$, —$C(O)R^{18}$ or —$S(O)_2R^{18}$ or optionally $R^{18}$ and $R^{19}$ together with the atom to which they are both attached form a cycloheteroalkyl or substituted cycloheteroalkyl ring, and where "$R^{18}$", "$R^{19}$", and "$R^{22}$" are each independently selected from the group consisting of hydrogen, substituted or unsubstituted alkyl, substituted or unsubstituted aryl, substituted or unsubstituted arylalkyl, substituted or unsubstituted cycloalkyl, substituted or unsubstituted cycloheteroalkyl, substituted or unsubstituted heteroalkyl, substituted or unsubstituted heteroaryl, and substituted or unsubstituted heteroarylalkyl.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

"Biological sample" as used herein is a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the embodiments, including, but not limited to, a tissue biopsy, a blood sample, a buccal scrape, a saliva sample, or a nipple discharge. As used herein, a "tissue biopsy" refers to an amount of tissue removed from an animal, such as a human, for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

"Providing a biological sample" means to obtain a biological sample for use in methods described in the embodiments. Most often, this will be done by removing a sample of cells from a patient, but can also be accomplished by using previously isolated cells (e.g., isolated by another person, at another time, and/or for another purpose), or by performing the methods of the embodiments in vivo. Archival tissues, having treatment or outcome history, will be particularly useful.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of Basic Technique* (3rd ed. 1994)).

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 ($3^{rd}$ ed. 1994).

"Correlating the amount" means comparing an amount of a substance, molecule or marker (such as Gli or GLI) that has been determined in one sample to an amount of the same substance, molecule or marker determined in another sample. The amount of the same substance, molecule or marker determined in another sample may be specific for a given cancer.

Synonyms of the term "determining the amount" are contemplated within the scope of the embodiments and include, but are not limited to, detecting, measuring, testing or determining, the presence, absence, amount or concentration of a molecule, such as Gli or GLI.

Synonyms of the term, "determining" are contemplated within the scope of the embodiments and include, but are not limited to, detecting, measuring, assaying, testing or determining, the presence, absence, amount or concentration of a molecule, such as a GLI polypeptide, a label, a compound of the embodiments. The term refers to both qualitative and quantitative determinations.

The terms "down-regulate" or "inhibiting" in the context of Shh signaling, GLI signaling, or Wnt2 signaling refers to partially or totally block Shh signaling, GLI signaling, or Wnt2 signaling as measured by known assays for Shh signaling, GLI signaling, or Wnt2 signaling. Inhibitors, for example, are compounds of the embodiments.

An "effective amount", "effective dose", "sufficient amount" or grammatical equivalents thereof of a compound of the embodiments for treatment is an amount that is sufficient to ameliorate, or in some manner, reduce a symptom or stop or reverse progression of a condition. Amelioration of a symptom of a particular condition, e.g., cancer, by administration of a particular pharmaceutical composition refers to any lessening, whether permanent or temporary, lasting or transit that can be associated with the administration of the pharmaceutical composition. An "effective amount" can be administered in vivo and in vitro.

The term "GLI" refers to a family of GLI proteins. GLI proteins include GLI (also referred to as GLI1), GLI2, and GLI3. Examples of GLI proteins include GLI1, GLI2, and GLI3.

A "GLI" polypeptide includes both naturally occurring or recombinant forms. Therefore, in some embodiments, a GLI polypeptide and a GLI subdomain polypeptide as described herein can comprise a sequence that corresponds to a human GLI sequence. Thus, exemplary GLI are provided herein and are known in the art. For example, several vertebrate GLI1, GLI2, and GLI3 proteins have been characterized, for example, human GLI1 (GenBank Accession Nos. NM_005269, P08151), mouse GLI1 (GenBank Accession Nos. NM_010296, AB025922, AAC09169, P47806), zebrafish GLI1 (GenBank Accession No. NM_178296), human GLI2 (GenBank Accession Nos. NM_030381; NM_030380; NM-030379, DQ086814), mouse GLI2 (GenBank Accession No. XM_922107), human GLI3 (GenBank Accession Nos. NM_000168, AJ250408, M57609, P10071, AAY87165), chimpanzee GLI3 (GenBank Accession Nos. NM_001034190, AY665272, Q5IS56), mouse GLI3 (GenBank Accession Nos. X95255, NM_008130, NP 032156, Q61602), rat GLI3 (GenBank Accession No. XM_225411), zebrafish GLI3 (GenBank Accession Nos. NM_205728, AY377429).

A GLI protein may be a full-length GLI protein or it may be a partial GLI protein, such as a subdomain of a GLI protein. For example, a "GLI3" polypeptide refers to a polypeptide and polymorphic variants, alleles, mutants of human GLI3 that: (i) has an amino acid sequence that has greater than about 60% amino acid sequence identity, 65%, 70%, 75%, 80%, 85%, 90%, or 91%, 92%, 93%, 94%, 95%, 96%, 97%, 98% or 99% or greater amino acid sequence identity, over a region of at least about 100, 150, 200, 250, 300, 500 or more amino acids, to a human GLI3 selected from GenBank Accession Nos. NM_000168, AJ250408, M57609, P10071, and AAY87165), (ii) comprises the amino acid motif FXXΦΦ (F=phenylalanine; X=any residue; Φ=any hydrophobic residue), such as the amino acid sequence FDAII, (iii) comprises a transcription activation domain, (iv) binds to a GLI DNA binding site and/or (v) binds to a TAF.

The term "GLI protein activity" refers to GLI signaling and includes, for example, transcriptional activation of a down-stream gene by GLI, binding of GLI protein to a GLI DNA binding site, and binding of GLI protein to other proteins, e.g., a TAF or to co-activators, such as CBP (Creb Protein Binding Protein).

The term "Gli" refers to a gene encoding a GLI protein. Thus, Gli1, Gli2, and Gli3 are genes encoding a GLI1, GLI2 and GLI3 protein, respectively.

A "Gli nucleic acid" or "gli polynucleotide" refers to a vertebrate gene encoding a GLI, GLI2, or GLI3 protein. A "Gli nucleic acid" includes both naturally occurring or recombinant forms. A Gli polynucleotide or GLI polypeptide encoding sequence is typically from a human, but may be from other mammals, but not limited to, a non-human primate, a rodent, e.g., a rat, mouse, or hamster; a cow, a pig, a horse, a sheep, or other mammal. Gli nucleic acids useful for practicing the embodiments, have been cloned and characterized, for example, human Gli1 (GenBank Accession Nos. NM_005269), mouse Gli1 (GenBank Accession Nos. NM_010296, AB025922), zebrafish Gli1 (GenBank Accession No. NM_178296), human Gli2 (GenBank Accession Nos. NM_030381; NM_030380; NM-030379, DQ086814), mouse Gli2 (GenBank Accession No. XM_922107), human Gli3 (GenBank Accession Nos. NM_000168, AJ250408, M57609), chimpanzee Gli3 (GenBank Accession Nos. NM_001034190, AY665272), mouse Gli3 (GenBank Accession Nos. X95255, NM_008130), rat Gli3 (GenBank Accession No. XM_225411), zebrafish Gli3 (GenBank Accession Nos. NM_205728, AY377429). A Gli polynucleotide may be a full-length Gli polynucleotide, i.e., encoding a complete GLI protein or it may be a partial Gli polynucleotide encoding a subdomain of a GLI protein.

The terms "GLI pathway", "GLI signaling" or "GLI signaling pathway" are used interchangeably and refer to the signaling pathway initiated by a hedgehog protein binding to its receptor(s) leading to the expression and/or activity of a GLI protein.

The term "hedgehog" is used interchangeably with the term "Hh" and is a cytokine that binds to a Hh receptor thereby initiating the Hh signaling pathway leading to the expression or activation of GLI proteins. There are three Hh family genes in mammals, Sonic hedgehog (Shh), Indian hedgehog (Ihh), and Desert hedgehog (Dhh). Several vertebrate hedgehog proteins are known in the art, for example, human SHH, murine SHH, rat SHH, human IHH, and murine DHH.

The terms "level of Gli mRNA" or "level of Wnt2 mRNA" in a biological sample refer to the amount of mRNA transcribed from a Gli or Wnt gene, respectively, that is present in a cell or a biological sample. The mRNA generally encodes a functional GLI or WNT protein, although mutations may be present that alter or eliminate the function of the encoded protein. A "level of Gli mRNA" or "level of Wnt2 mRNA" need not be quantified, but can simply be detected, e.g., a subjective, visual detection by a human, with or without comparison to a level from a control sample or a level expected of a control sample.

The "level of GLI polypeptide" or "level of Wnt2 polypeptide" in a biological sample refers to the amount of polypeptide translated from a Gli or Wnt2 mRNA, respectively, which is present in a cell or biological sample. The polypeptide may or may not have GLI or WNT2 protein activity. A "level of GLI polypeptide" or "WNT2 polypeptide" need not be quantified, but can simply be detected, e.g., a subjective, visual detection by a human, with or without comparison to a level from a control sample or a level expected of a control sample.

As used herein a "modulator" of the level or activity of a polypeptide, such as a GLI includes an activator and/or inhibitor of that polypeptide and is used to refer to compounds that activate or inhibit the level of expression of the polypeptide or the activity of the polypeptide. In certain embodiments, polypeptides are GLI1, GLI2, or GLI3. Activators are compounds that, e.g., induce or activate the expression of a polypeptide of the embodiments or bind to, stimulate, increase, open, activate, facilitate, or enhance activation, sensitize or up regulate the activity of a polypeptide of the embodiments. Activators include naturally occurring and synthetic compounds, small chemical molecules and the like. Assays for activators include, e.g., applying candidate compounds to cells expressing a GLI polypeptide and then determining the functional effects. Samples or assays comprising a GLI polypeptide that are treated with a potential activator are compared to control samples without the activator to examine the extent of effect. Control samples (untreated with candidate compounds) are assigned a relative activity value of 100%. Activation of the polypeptide is achieved when the polypeptide activity value relative to the control is 110%, optionally 130%, 150%, optionally 200%, 300%, 400%, 500%, or 1000-3000% or more higher. Inhibitors are compounds that, e.g., repress or inactivate the expression of a polypeptide of the embodiments or bind to, decrease, close, inactivate, impede, or reduce activation, desensitize or down regulate the activity of a polypeptide of the embodiments. Inhibitors include nucleic acids such as siRNA and antisense RNA that interfere with the expression of a GLI protein, as well as naturally occurring and synthetic compounds, small chemical molecules and the like. Assays for inhibitors are described herein. Samples or assays comprising a GLI polypeptide that are treated with a potential inhibitor are compared to control samples without the inhibitor to examine the extent of effect. Control samples (untreated with candidate compounds) are assigned a relative activity value of 100% Inhibition of the polypeptide is achieved when the polypeptide activity value relative to the control is reduced by 10%, optionally 20%, optionally 30%, optionally 40%, optionally 50%, 60%, 70%, 80%, or 90-100%.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant. Similarly, a "recombinant protein" is a protein made using recombinant techniques, i.e., through the expression of a recombinant nucleic acid as depicted above.

By "resistant to chemotherapeutic agents" herein is meant a tumor that does not respond to treatment with a chemotherapeutic agent, i.e., is not killed by, or growth-inhibited by, such treatment.

The terms "subject" or "patient" refer to a mammal, such as a human, in need of treatment for a condition, such as cancer, disorder, or disease.

The term "TAF" refers to a TBP-associated factor. In certain embodiments, the TAF is a $TAF_{II}$, i.e., a TAF protein involved in mediating transcriptional activation of a eukaryotic gene transcribed by RNA polymerase II. A TAF protein interacts with other transcriptional activators or repressors (Goodrich and Tjian, *Curr Opin Cell Biol* 6(3):403-9 (1994); Albright and Tjian, *Gene* 242(1-2):1-13 (2000)). A TAF can be from human, mouse, *Drosophila* or yeast. An example of a TAF protein interacting with a GLI is a $TAF_{II}31$ protein. Klemm et al. cloned a human TFIID subunit, which they termed $hTAF_{II}32$ (Klemm et al. 1995, *Proc Natl Acad Sci USA*, 92(13):5788-92). The 32-kD protein was isolated from HeLa cell nuclear extracts and partially sequenced. The identified cDNA has a deduced amino acid sequence of 264 residues and is related to the *Drosophila* $TAF_{II}40$. Klemm et al. showed that $TAF_{II}32$ interacts with GTF2B and with the viral transcriptional transactivator VP16 (Klemm et al. 1995, *Proc Natl Acad Sci USA*, 92(13):5788-92). The authors showed that recombinantly expressed $TAF_{II}32$ was functional in a partial recombinant $TF_{II}D$ complex and that the recombinant complex mediated activation by a GAL4-VP16 fusion protein. $TAF_{II}32$ and $TAF_{II}31$ are two names for the same protein, which is nowadays also referred to as TAF9. Lu et al. cloned TAF9, which they called $TAF_{II}31$. TAF9 encodes a 264-amino acid protein. Immunoprecipitation and binding analyses showed interaction of TAF9 with the N-terminal domain of p53 at sites identical to those bound by MDM2, the major cellular negative regulator of p53 activity. (Lu et al., 1995, *Proc Natl Acad Sci USA*, 92(11): 5154-8). Human $TAF_{II}31$ nucleotide and protein sequences can be found, e.g., at GenBank accession numbers U25112, U21858, and NM_016283.

As used herein, the terms "treat", "treating", and "treatment" include: (1) preventing a disease, such as cancer, i.e. causing the clinical symptoms of the disease not to develop in a subject that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms. Treatment means any manner in which the symptoms or pathology of a condition, disorder, or disease are ameliorated or otherwise beneficially altered. In certain embodiments, the subject in need of such treatment is a mammal, such as a human.

"Tumor cell" refers to precancerous, cancerous, and normal cells in a tumor.

The terms "Wnt" refer to a family of mammalian genes and encoded proteins related to the *Drosophila* segment polarity gene, wingless. In humans, the Wnt family of genes typically encodes 38 to 43 kDa cysteine rich glycoproteins having hydrophobic signal sequence, and a conserved asparagine-linked oligosaccharide consensus sequence (Shimizu et al., *Cell Growth Differ* 8(12):1349-58 (1997)). The Wnt family contains at least 19 mammalian members. Exemplary Wnt proteins include Wnt1, Wnt2, Wnt3, Wnt3A, Wnt4, Wnt5A, Wnt5B, Wnt6, Wnt7A, Wnt7B, Wnt8A, Wnt8B, WNT10A, Wnt10B, Wnt11, Wnt12, Wnt13, Wnt14, Wnt1S, and Wnt16. In certain embodiments, a Wnt protein is Wnt2, such as a human Wnt2 protein.

In describing the embodiments, the structure of the compounds will be discussed. Then, pharmaceutical formulations containing the compounds will be discussed, followed by a description of their methods of use, and kits.

Small Molecule Compounds

The compositions of the present disclosure include compounds of Formulae I-III, shown below. Pharmaceutical compositions and methods of the present disclosure also include compounds of Formulae I-III.

Formula I

The present disclosure provides a compound of Formula (I):

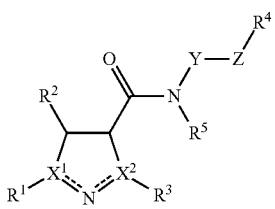

(I)

wherein each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C;

$R^1$ is aryl or substituted aryl;

$R^2$ is selected from aryl, substituted aryl, heteroaryl, substituted heteroaryl, and alkyl;

$R^3$ is aryl or substituted aryl;

Y is a direct bond or $C_1$-$C_4$ alkyl;

Z is $C_1$-$C_4$ alkyl or aryl;

$R^4$ is —OH; and $R^5$ is hydrogen or $C_1$-$C_6$ alkyl;

and salts, hydrates, solvates, stereoisomers and prodrugs thereof.

Formula II

The present disclosure provides a compound of Formula (II):

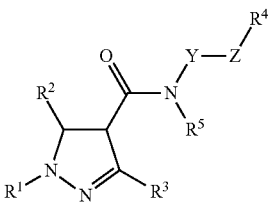

(II)

wherein $R^1$ is aryl or substituted aryl;

$R^2$ is selected from aryl, substituted aryl, heteroaryl, substituted heteroaryl, and alkyl;

$R^3$ is aryl or substituted aryl;

Y is a direct bond or $C_1$-$C_4$ alkyl;

Z is $C_1$-$C_4$ alkyl or aryl;

$R^4$ is —OH; and $R^5$ is hydrogen or $C_1$-$C_6$ alkyl;

and salts, hydrates, solvates, stereoisomers and prodrugs thereof.

Formula III

The present disclosure provides a compound of Formula (III):

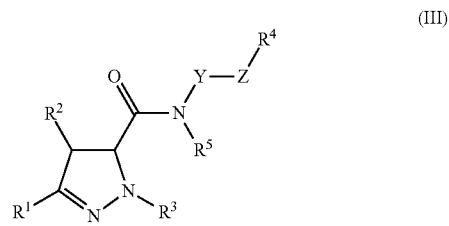

(III)

wherein $R^1$ is aryl or substituted aryl;

$R^2$ is selected from aryl, substituted aryl, heteroaryl, substituted heteroaryl, and alkyl;

$R^3$ is aryl or substituted aryl;

Y is a direct bond or $C_1$-$C_4$ alkyl;

Z is $C_1$-$C_4$ alkyl or aryl;

$R^4$ is —OH; and $R^5$ is hydrogen or $C_1$-$C_6$ alkyl;

and salts, hydrates, solvates, stereoisomers and prodrugs thereof.

In Formula (I), each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C. In certain embodiments, $X^1$ is N and $X^2$ is C. In certain embodiments, $X^1$ is C and $X^2$ is N.

In Formulae (I)-(III), $R^1$ is aryl or substituted aryl. In certain embodiments, $R^1$ is aryl. In certain embodiments, $R^1$ is substituted aryl. In certain embodiments, $R^1$ is substituted aryl, where the substituent is alkyl or halogen.

In Formulae (I)-(III), $R^2$ is selected from aryl, substituted aryl, heteroaryl, substituted heteroaryl, and alkyl. In certain embodiments, $R^2$ is aryl or substituted aryl. In certain embodiments, $R^2$ is aryl. In certain embodiments, $R^2$ is substituted aryl. In certain embodiments, $R^2$ is heteroaryl or substituted heteroaryl. In certain embodiments, $R^2$ is heteroaryl. In certain embodiments, $R^2$ is substituted heteroaryl. In certain embodiments, $R^2$ is alkyl.

In certain embodiments, $R^2$ is selected from aryl, substituted aryl, heteroaryl, and alkyl. In certain embodiments, $R^2$ is selected from heteroaryl, and alkyl. In certain embodiments, $R^2$ is substituted aryl, where the substituent is alkyl or halogen.

In Formulae (I)-(III), $R^3$ is aryl or substituted aryl. In certain embodiments, $R^3$ is aryl. In certain embodiments, $R^3$ is substituted aryl. In certain embodiments, $R^3$ is substituted aryl, where the substituent is alkyl or halogen.

In Formulae (I)-(III), $R^5$ is hydrogen or $C_1$-$C_6$ alkyl. In certain embodiments, $R^5$ is hydrogen. In certain embodiments, $R^5$ is $C_1$-$C_6$ alkyl.

In Formulae (I)-(III), Y is a direct bond or $C_1$-$C_4$ alkyl. In certain embodiments, Y is a direct bond. In certain embodiments, Y is $C_1$-$C_4$ alkyl.

In Formulae (I)-(III), Z is $C_1$-$C_4$ alkyl or aryl. In certain embodiments, Z is $C_1$-$C_4$ alkyl. In certain embodiments, Z is aryl.

In certain embodiments, Y is a direct bond and Z is $C_1$-$C_4$ alkyl. In certain embodiments, Y is a direct bond and Z is aryl. In certain embodiments, Y is $C_1$-$C_4$ alkyl and Z is $C_1$-$C_4$ alkyl. In certain embodiments, Y is $C_1$-$C_4$ alkyl and Z is aryl.

In certain embodiments, Y is a direct bond and Z is $C_1$-$C_4$ alkyl and $R^5$ is hydrogen. In certain embodiments, Y is a direct bond and Z is aryl and $R^5$ is hydrogen. In certain embodiments, Y is $C_1$-$C_4$ alkyl and Z is $C_1$-$C_4$ alkyl and $R^5$ is hydrogen. In certain embodiments, Y is $C_1$-$C_4$ alkyl and Z is aryl and $R^5$ is hydrogen.

In certain embodiments, $R^1$ is aryl, $R^2$ is heteroaryl, and $R^3$ is aryl.

In certain embodiments, $R^1$ is aryl, $R^2$ is alkyl, and $R^3$ is substituted aryl.

In certain embodiments, $R^1$ is aryl, $R^2$ is aryl, and $R^3$ is aryl.

In certain embodiments, $R^1$ is aryl, $R^2$ is substituted aryl, and $R^3$ is substituted aryl.

In certain embodiments, Y is $C_1$-$C_4$ alkyl and Z is $C_1$-$C_4$ alkyl, such that Y and Z form —$(CH_2)_3$—$C(CH_3)_2$—$CH_2$—.

In certain embodiments, Y is $C_1$-$C_4$ alkyl and Z is aryl, such that Y and Z form

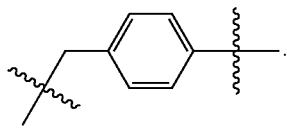 [SMILES: *Cc1ccc(*)cc1]

Certain embodiments of the compounds are illustrated in the following table.

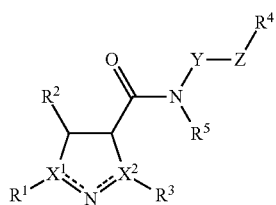

| Compound | $X^1$ | $X^2$ | $R^1$ | $R^2$ | $R^3$ | $R^5$ | —Y—Z—$R^4$ |
|---|---|---|---|---|---|---|---|
| 1 | N | C | phenyl | thiophenyl | phenyl | H | —CH₂CH₂CH₂C(CH₃)₂CH₂OH |
| 2 | C | N | phenyl | phenyl | phenyl | H | —CH₂-C₆H₄-OH |
| 3 | N | C | chlorophenyl | dimethylphenyl | fluorophenyl | H | —CH₂CH₂-C₆H₄-OH |
| 4 | N | C | phenyl | propyl | fluorophenyl | H | —CH₂CH₂CH₂C(CH₃)₂CH₂OH |
| 5 | N | C | phenyl | phenyl | fluorophenyl | H | —CH₂CH₂CH₂C(CH₃)₂CH₂OH |
| 6 | N | C | phenyl | fluorophenyl | fluorophenyl | H | —CH₂CH₂CH₂C(CH₃)₂CH₂OH |

Embodiments of the compounds, and salts or solvates or stereoisomers thereof, include 1,3-diphenyl-5-thiophen-3-yl-4,5-dihydro-1H-pyrazole-4-carboxylic acid (5-hydroxy-4,4-dimethyl-pentyl)-amide (Compound 1), shown below.

(Compound 1)

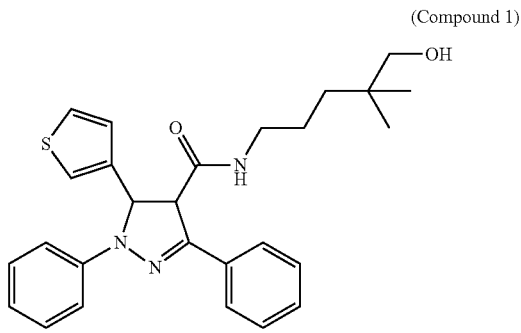 [SMILES: CC(C)(CO)CCCNC(=O)C1C(c2ccccc2)=NN(c2ccccc2)C1c1ccsc1]

Embodiments of the compounds, and salts or solvates or stereoisomers thereof, include 3-(4-fluoro-phenyl)-1-phenyl-5-propyl-4,5-dihydro-1H-pyrazole-4-carboxylic acid (5-hydroxy-4,4-dimethyl-pentyl)-amide, shown below.

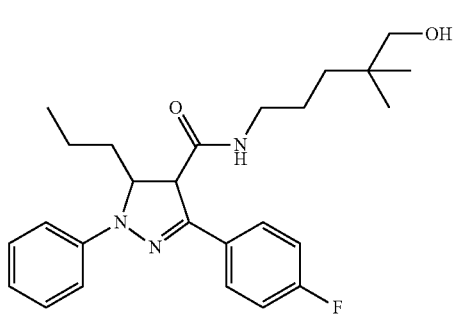 [SMILES: CCCC1C(C(=O)NCCCC(C)(C)CO)C(c2ccc(F)cc2)=NN1c1ccccc1]

Embodiments of the compounds, and salts or solvates or stereoisomers thereof, include 1,3,5-triphenyl-4,5-dihydro-1H-pyrazole-4-carboxylic acid 4-hydroxy-benzylamide (Compound 2), shown below.

(Compound 2)

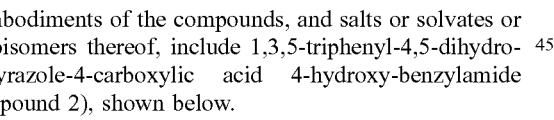

Embodiments of the compounds, and salts or solvates or stereoisomers thereof, include 3-(4-fluoro-phenyl)-5-(3-fluoro-phenyl)-1-phenyl-4,5-dihydro-1H-pyrazole-4-carboxylic acid (5-hydroxy-4,4-dimethyl-pentyl)-amide (Compound 6), shown below.

(Compound 6)

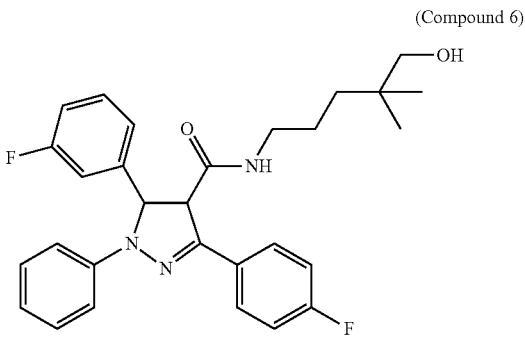 [SMILES: CC(C)(CO)CCCNC(=O)C1C(c2ccc(F)cc2)=NN(c2ccccc2)C1c1cccc(F)c1]

Embodiments of the compounds, and salts or solvates or stereoisomers thereof, include 1-(5-chloro-2-methyl-phenyl)-5-(2,6-dimethyl-phenyl)-3-(2-fluoro-phenyl)-4,5-dihydro-1H-pyrazole-4-carboxylic acid [2-(4-hydroxy-phenyl)-ethyl]-amide (Compound 3), shown below.

(Compound 3)

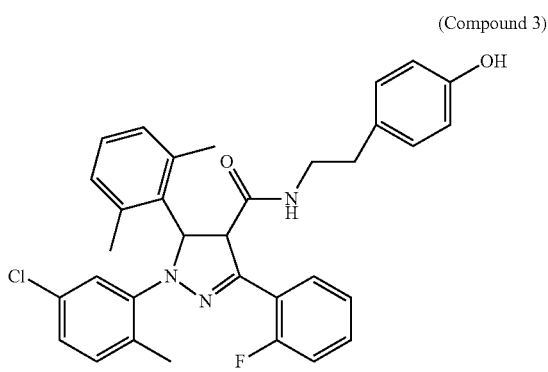 [SMILES: Cc1ccc(Cl)cc1N1N=C(c2ccccc2F)C(C(=O)NCCc2ccc(O)cc2)C1c1c(C)cccc1C]

Embodiments of the compounds, and salts or solvates or stereoisomers thereof, include 3-(4-fluoro-phenyl)-1,5-diphenyl-4,5-dihydro-1H-pyrazole-4-carboxylic acid (5-hydroxy-4,4-dimethyl-pentyl)-amide (Compound 5), shown below.

(Compound 5)

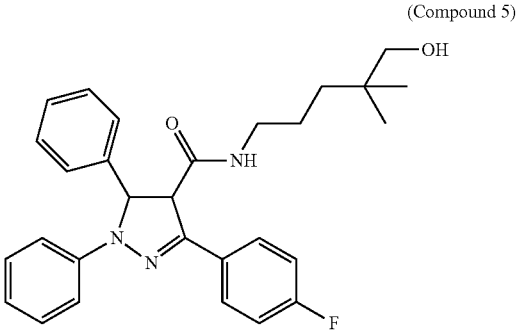 [SMILES: CC(C)(CO)CCCNC(=O)C1C(c2ccc(F)cc2)=NN(c2ccccc2)C1c1ccccc1]

Preparation of Small Molecule Compounds

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds of the embodiments can be prepared according to the synthetic scheme below. In Synthetic Scheme 1, for illustrative purposes, $R^1$ and $R^3$ are phenyl; $R^x$ is a leaving group; and $X^1$, $X^2$, $R^2$, $R^5$, Y, Z, and $R^4$ are as previously defined.

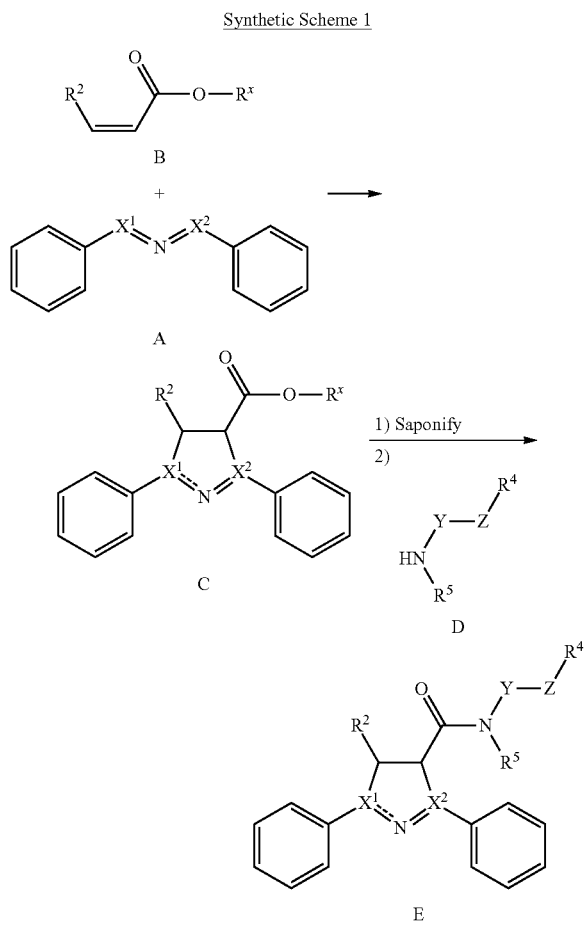

Synthetic Scheme 1

Pyrazole derivatives can be formed with reaction between a hydrazone and an unsaturated compound. In Synthetic Scheme 1, Compound A is condensed with Compound B to form Compound C. The reaction can be run neatly or with a suitable solvent. The reaction can be run at various temperatures, including with cooling, at room temperature, or with heating. In certain embodiments, Compound A is refluxed with Compound B in a suitable solvent. A suitable solvent, for example, is methanol, methylene chloride, DMF, or THF. One skilled in the art would be able to determine suitable reaction conditions according to the specific reactants.

With further reference to Synthetic Scheme 1, Compound C is saponified. In certain embodiments, Compound C comprises an ester, wherein $R^x$ is an alkyl group. Conditions for saponification of Compound C include reaction in a suitable solvent with a base. Suitable solvents for saponification include, but are not limited to, water, an alcohol, such as methanol and ethanol, THF, and mixtures thereof. Suitable bases include, but are not limited to, lithium hydroxide, sodium hydroxide, and potassium hydroxide.

Then, saponified Compound C is reacted with Amine D to form Compound E in a peptide coupling reaction. A peptide coupling reaction typically employs a conventional peptide coupling reagent and is conducted under conventional coupling reaction conditions. Suitable coupling reagents for use include, by way of example, carbodiimides, such as ethyl-3-(3-dimethylamino)propylcarbodiimide (EDC or EDCI), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), 0-(7-azabenzotriazol-1-yl)-N,N,N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as methylene chloride, THF or DMF.

In an illustrative example, the compounds of the embodiments can be prepared via condensation of ethyl cinnamate or an unsaturated ester with benzaldehyde phenylhydrazone, followed by saponification of the ethyl ester and reaction with an amine to afford the desired amide end-product, as shown in the Examples. Alternatively, the compounds of the embodiments can be prepared by first reacting cinnamic acid or an unsaturated ester with the amine to prepare the amide, then condensation with the benzaldehyde phenylhydrazone. One of skill in the art will recognize that additional methods exist for the preparation of the compounds of the embodiments.

In a certain embodiment, a compound of Formula (I) comprises a label. This is useful for detecting and testing the distribution of the compound after administration in vivo. For example, tritium ($^3H$) can be used as a label in conventional pharmacokinetic/dynamic studies. A compound comprising a label can be detected by, for example, spectroscopic, photochemical, biochemical, immunochemical, chemical, or other physical means.

A compound of the embodiments may also contain unnatural proportions of atomic isotopes at one or more of the atoms that constitute such compounds. For example, the compounds may be radiolabeled with radioactive isotopes, such as for example tritium ($^3H$) or carbon-14 ($^{14}C$). All isotopic variations of the compounds of the embodiments, whether radioactive or not, are intended to be encompassed within the scope of the embodiments.

Enantiomer-Specific Activity

In certain embodiments, the compounds described herein may include two or more stereoisomers. As used herein, the term "stereoisomers" refers to compounds of the embodiments that possess asymmetric carbon atoms (optical centers) or double bonds. For example, the compounds described herein may include two enantiomers. As used herein, an "enantiomer" is one of two stereoisomers that are non-superimposable mirror images of each other. In some instances, a racemic mixture of enantiomers of a compound may be separated into individual enantiomers. For instance, enantiomers may be separated using separation techniques, such as, but not limited to high-performance liquid chromatography (HPLC) (e.g., chiral HPLC), crystallization, and the like. In other embodiments, individual enantiomers may be synthesized separately, for example by using chiral starting materials and asymmetric synthetic techniques.

In certain embodiments, individual enantiomers may be separated using chiral separation techniques (e.g., chiral HPLC), as described above. In some cases, the chiral separation technique is configured to provide substantially pure individual enantiomers. For example, an individual enantiomer may have a purity of 90% or more, such as 95% or more, or 96% or more, or 97% or more, or 98% or more, or 99% or more, or 99.5% or more, or 99.9% or more, or even 100% purity. In certain instances, an individual enantiomer has a purity of 98%, or 99%, or 99.9%. In some cases, the separated enantiomer has an enantiomeric excess of 90% or more, such as 95% or more, or 96% or more, or 97% or more, or 98% or more, or 99% or more, or 99.5% or more, or 99.9% or more.

In embodiments where chiral separation techniques (e.g., chiral HPLC) are used to separate the individual enantiomers, the different enantiomers may have significantly different retention times under the separation conditions used (see e.g., Example 16 below). For example, a first enantiomer may have a significantly shorter retention time than a second enantiomer. In these cases, the first enantiomer may be described as the "faster eluting" enantiomer, and the second enantiomer may be described as the "slower eluting" enantiomer. In some instances, the first and second enantiomers may have a difference in elution times of 0.1 min or more, including 0.2 min or more, such as 0.3 min or more, or 0.4 min or more, or 0.5 min or more, or 0.6 min or more, or 0.7 min or more, or 0.8 min or more, or 0.9 min or more, or 1 min or more, or 1.1 min or more, or 1.2 min or more, or 1.3 min or more, or 1.4 min or more, or 1.5 min or more, or 1.6 min or more, or 1.7 min or more, or 1.8 min or more, or 1.9 min or more, or 2 min or more or 2.5 min or more, or 3 min or more, or 3.5 min or more, or 4 min or more, or 4.5 min or more, or 5 min or more. In some embodiments, the first and second enantiomers have a difference in elution times ranging from 0.5 min to 2 min, such as 0.5 min to 1.5 min, or from 0.7 min to 1.2 min. For example, the first and second enantiomers may have a difference in elution times of 1 min.

In certain embodiments, one enantiomer may have an activity greater than the activity of the other enantiomer. For example, a first enantiomer may have an activity greater than the activity of a second enantiomer. Alternatively, the second enantiomer may have an activity greater than the activity of the first enantiomer. In some cases, as described above, the enantiomers may be distinguished from each other based on their retention times in a chiral separation technique (e.g., chiral HPLC). In these instances, the first enantiomer (e.g., the faster eluting enantiomer) may have an activity significantly different from the second enantiomer (e.g., the slower eluting enantiomer). For instance, the faster eluting enantiomer may have an activity greater than the slower eluting enantiomer. In other embodiments, the slower eluting enantiomer has an activity greater than the faster eluting enantiomer.

In some cases, the activity of a compound may be measured by its half-maximal inhibitor concentration ($IC_{50}$). The $IC_{50}$ is a measure of the effectiveness of a compound in inhibiting a biological process (or component of a process, e.g., an enzyme, cell, cell receptor, microorganism, etc.). This quantitative measure indicates how much of a compound is needed to inhibit the biological process by half. In certain embodiments, as described above, enantiomers of a compound may have significantly different activities. For example, a second enantiomer (e.g., the slower eluting enantiomer) may have an $IC_{50}$ less than a first enantiomer (e.g., the faster eluting enantiomer); i.e., the second enantiomer is more active than the first enantiomer. In some cases, the $IC_{50}$ of the second enantiomer is 75% or less of the $IC_{50}$ of the first enantiomer, such as 70% or less, including 65% or less, or 60% or less, or 55% or less, or 50% or less, or 45% or less, or 40% or less, or 35% or less, or 30% or less, or 25% or less, or 20% or less, or 15% or less, or 10% or less, or 5% or less, or 3% or less, or the $IC_{50}$ of the second enantiomer is 1% or less of the $IC_{50}$ of the first enantiomer.

In other embodiments, the first enantiomer (e.g., the faster eluting enantiomer) has an $IC_{50}$ less than the second enantiomer (e.g., the slower eluting enantiomer); i.e., the first enantiomer is more active than the second enantiomer. In certain instances, the $IC_{50}$ of the first enantiomer is 75% or less of the $IC_{50}$ of the second enantiomer, such as 70% or less, including 65% or less, or 60% or less, or 55% or less, or 50% or less, or 45% or less, or 40% or less, or 35% or less, or 30% or less, or 25% or less, or 20% or less, or 15% or less, or 10% or less, or 5% or less, or 3% or less, or the $IC_{50}$ of the first enantiomer is 1% or less of the $IC_{50}$ of the second enantiomer.

Testing of Small Molecule Compounds in Cell-based Assays

A compound of the embodiments can be screened for activity in vitro and in vivo. For in vitro assays, the disclosure provides cell-based cytotoxicity assays, as described herein. For in vivo assays, the disclosure provides mouse xenograft assays as described herein.

Pharmaceutical Compositions

The disclosure provides a pharmaceutical composition or a medicament comprising at least one compound of Formula (I) and optionally a pharmaceutically acceptable carrier. A pharmaceutical composition or medicament can be administered to a patient for the treatment of, for example, a condition, such as cancer.

Formulation and Administration

The compounds of the embodiments are useful in the manufacture of a pharmaceutical composition or a medicament comprising an effective amount thereof in conjunction or mixture with excipients or carriers suitable for either enteral or parenteral application.

Pharmaceutical compositions or medicaments for use in the embodiments can be formulated by standard techniques using one or more physiologically acceptable carriers or excipients. Suitable pharmaceutical carriers are described herein and in "Remington's Pharmaceutical Sciences" by E. W. Martin. The compounds of embodiments and their physiologically acceptable salts and solvates can be formulated for administration by any suitable route, including via inhalation, topically, nasally, orally, parenterally, or rectally.

Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablets or a capsule prepared by conventional means with a pharmaceutically acceptable excipient. In certain embodiments, tablets and gelatin capsules comprise the active ingredient, i.e., a compound of the embodiments, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds of the embodiments can be formulated for parenteral administration by injection, for example by bolus injection or continuous infusion. Formulations for injection can be presented in unit dosage form, for example, in ampoules or in multi-dose containers, with an added preservative. In certain embodiments, injectable compositions are aqueous isotonic solutions or suspensions, and suppositories are prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, or about 1 to 50%, of the active ingredient.

Suitable formulations for transdermal application include an effective amount of a compound of the embodiments with carrier. In certain embodiments, carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and optionally an adhesive overlay to secure the device to the skin. Matrix transdermal formulations may also be used.

In certain embodiments, suitable formulations for topical application, e.g., to the skin and eyes, are aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Combination Formulations

In certain embodiments, a pharmaceutical composition or medicament comprises an effective amount of a compound of the embodiments as defined herein, and another therapeutic agent, such as a chemotherapeutic agent.

Examples of chemotherapeutic agents include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin diethylstilbestrol (DES), vismodegib (GDC-0449), erlotinib (Tarceva®), pemetrexed (Alimta®), PI3K inhibitor LY294002, TGFβ inhibitor SB431542, and cisplatin. See, generally, The Merck Manual of Diagnosis and Therapy, 15th Ed. 1987, pp. 1206-1228, Berkow et al., eds., Rahway, N.J.

In certain embodiments, a pharmaceutical composition or medicament comprises a compound of the embodiments and another therapeutic agent selected from vismodegib (GDC-0449), erlotinib (Tarceva®), pemetrexed (Alimta®), LY294002, SB431542, and cisplatin. In certain embodiments, a pharmaceutical composition or medicament comprises a compound of the embodiments and vismodegib (GDC-0449). In certain embodiments, a pharmaceutical composition or medicament comprises a compound of the embodiments and erlotinib (Tarceva®). In certain embodiments, a pharmaceutical composition or medicament comprises a compound of the embodiments and pemetrexed (Alimta®). In certain embodiments, a pharmaceutical composition or medicament comprises a compound of the embodiments and LY294002. In certain embodiments, a pharmaceutical composition or medicament comprises a compound of the embodiments and SB431542. In certain embodiments, a pharmaceutical composition or medicament comprises a compound of the embodiments and cisplatin.

Certain embodiments provide for a combination of one or more of Compounds 1-6 and another therapeutic agent, for example as shown in the following table.

| \multicolumn{6}{c|}{Examples of Combinations of Compounds 1-6 and another therapeutic agent} |
|---|---|---|---|---|---|
| Compound 1 and vismodegib (GDC-0449) | Compound 1 and erlotinib (Tarceva ®) | Compound 1 and pemetrexed (Alimta ®) | Compound 1 and LY294002 | Compound 1 and SB431542 | Compound 1 and cisplatin |
| Compound 2 and vismodegib (GDC-0449) | Compound 2 and erlotinib (Tarceva ®) | Compound 2 and pemetrexed (Alimta ®) | Compound 2 and LY294002 | Compound 2 and SB431542 | Compound 2 and cisplatin |
| Compound 3 and vismodegib (GDC-0449) | Compound 3 and erlotinib (Tarceva ®) | Compound 3 and pemetrexed (Alimta ®) | Compound 3 and LY294002 | Compound 3 and SB431542 | Compound 3 and cisplatin |
| Compound 4 and vismodegib (GDC-0449) | Compound 4 and erlotinib (Tarceva ®) | Compound 4 and pemetrexed (Alimta ®) | Compound 4 and LY294002 | Compound 4 and SB431542 | Compound 4 and cisplatin |
| Compound 5 and vismodegib (GDC-0449) | Compound 5 and erlotinib (Tarceva ®) | Compound 5 and pemetrexed (Alimta ®) | Compound 5 and LY294002 | Compound 5 and SB431542 | Compound 5 and cisplatin |
| Compound 6 and vismodegib (GDC-0449) | Compound 6 and erlotinib (Tarceva ®) | Compound 6 and pemetrexed (Alimta ®) | Compound 6 and LY294002 | Compound 6 and SB431542 | Compound 6 and cisplatin |

When used with a compound of the embodiments, such chemotherapeutic agent may be used individually (e.g., 5-FU and compound of the embodiments), sequentially (e.g., 5-FU and compound of the embodiments for a period of time followed by e.g., MTX and compound of the embodiments), or in combination with one or more other such chemotherapeutic agents (e.g., 5-FU, MTX and compound of the embodiments, or 5-FU, radiotherapy and compound of the embodiments). Administration may be by the same or different route of administration or together in the same pharmaceutical formulation.

In certain embodiments, a therapeutically effective amount of a compound of the embodiments is administered in combination with surgery, and optionally administration of another chemotherapeutic agent.

Therapeutically Effective Amount and Dosing

In certain embodiments, a pharmaceutical composition or medicament is administered to a patient at a therapeutically effective dose to prevent, treat, or control cancer. The pharmaceutical composition or medicament is administered to a patient in an amount sufficient to elicit an effective therapeutic response in the patient. An effective therapeutic response is a response that at least partially arrests or slows the symptoms or complications of the disease. An amount adequate to accomplish this is defined as "therapeutically effective dose."

The dosage of compound administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for oral administration to a mammal of about 50 to 70 kg may contain between about 5 and 500 mg of the active ingredient. Typically, a dosage of the compound of the embodiments, is a dosage that is sufficient to achieve the desired effect.

Optimal dosing schedules can be calculated from measurements of compound accumulation in the body of a subject. In general, dosage is from 1 ng to 1,000 mg per kg of body weight and may be given once or more daily, weekly, monthly, or yearly. Persons of ordinary skill in the art can determine optimum dosages, dosing methodologies and repetition rates.

In certain embodiments, a pharmaceutical composition or medicament that includes a compound of the embodiments is administered in a daily dose in the range from about 1 mg of compound per kg of subject weight (1 mg/kg) to about 1 g/kg for multiple days. In certain embodiments, the daily dose is a dose in the range of about 5 mg/kg to about 500 mg/kg. In certain embodiments, the daily dose is about 10 mg/kg to about 250 mg/kg. In certain embodiments, the daily dose is about 25 mg/kg to about 150 mg/kg. The daily dose can be administered once per day or divided into sub-doses and administered in multiple doses, e.g., twice, three times, or four times per day.

To achieve the desired therapeutic effect, a compound can be administered for multiple days at the therapeutically effective daily dose. Thus, therapeutically effective administration of a compound to treat cancer in a subject requires periodic (e.g., daily) administration that continues for a period ranging from three days to two weeks or longer. Typically, a compound will be administered for at least three consecutive days, often for at least five consecutive days, more often for at least ten, and sometimes for 20, 30, 40 or more consecutive days. While consecutive daily doses are a one route to achieve a therapeutically effective dose, a therapeutically beneficial effect can be achieved even if the compound is not administered daily, so long as the administration is repeated frequently enough to maintain a therapeutically effective concentration of the compound in the subject. For example, one can administer the compound every other day, every third day, or, if higher dose ranges are employed and tolerated by the subject, once a week.

Optimum dosages, toxicity, and therapeutic efficacy of such compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. In certain embodiments, the disclosure provides compounds that exhibit large therapeutic indices. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. In certain embodiments, the dosage of such compounds lies within a range of circulating concentrations that include the $ED_{50}$ with little or no toxicity. The dosage can vary within this range depending upon the dosage form employed and the route of administration. For any compound used in the methods of the embodiments, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a small molecule compound is from about 1 ng/kg to 100 mg/kg for a typical subject.

Following successful treatment, it may be desirable to have the subject undergo maintenance therapy to prevent the recurrence of the condition treated, e.g., a cancer.

Treating Cancer Using Small Molecule Compounds

The embodiments provide methods for using the compounds of formula (I) to, for example, treat a condition, such as a cancer, expressing a GLI polypeptide. Any cell or tumor cell expressing a GLI polypeptide can be used to practice a method of the embodiments.

In certain embodiments, a method for treating a subject suffering from a cancerous condition is provided. This method comprises the step of administering to the subject a therapeutically effective amount of a compound of the embodiments, wherein the cancerous condition is characterized by expressing a GLI polypeptide and wherein the step of administering results in the treatment of the subject.

Further, the embodiments provide for a compound of formula (I) for use in medical therapy. Further, the embodiments provide for a compound of formula (I) for use in the treatment of a cancer. Further, the embodiments provide for the use of a compound of formula (I) in the manufacture of a medicament treatment of a cancer.

Certain cancers express a GLI polypeptide. Thus, most cancerous conditions or cancers in a subject can be treated using a compound of the embodiments. In certain embodiments, a cancerous condition or cancer is selected from colon cancer, melanoma, mesothelioma, lung cancer, renal cell carcinoma, breast cancer, prostate cancer, sarcoma, ovarian cancer, esophageal cancer, gastric cancer, hepatocellular cancer, nasopharyngeal cancer, pancreatic cancer, and glioma.

In certain embodiments, a compound is used to treat a subject suffering from a colon cancer expressing a GLI polypeptide, such as a GLI1, GLI2, or GLI3 polypeptide.

In certain embodiments, a compound is used to treat a subject suffering from a breast cancer expressing a GLI polypeptide, such as a GLI1, GLI2, or GLI3 polypeptide.

In certain embodiments, a compound is used to treat a subject suffering from a nasopharyngeal cancer expressing a GLI polypeptide, such as a GLI1, GLI2, or GLI3 polypeptide.

In certain embodiments, a compound is used to treat a subject suffering from a lung cancer expressing a GLI polypeptide, such as a GLI1, GLI2, or GLI3 polypeptide. A lung cancer includes, but is not limited to, bronchogenic carcinoma [squamous cell, undifferentiated small cell, undifferentiated large cell, adenocarcinoma], alveolar [bronchiolar] carcinoma, bronchial adenoma, sarcoma, lymphoma, chondromatous hamartoma, mesothelioma, SCLC, and NSCLC.

In certain embodiments, a compound is used to treat a subject suffering from a sarcoma expressing a GLI polypeptide, such as a GLI1, GLI2, or GLI3 polypeptide. A sarcoma includes, but is not limited to, cancers such as angiosarcoma, fibrosarcoma, rhabdomyosarcoma, liposarcoma, myxoma, rhabdomyoma, fibroma, lipoma and teratoma.

In certain embodiments, a compound is used to treat a subject suffering from a gastrointestinal cancer expressing a GLI polypeptide, such as a GLI1, GLI2, or GLI3 polypeptide. A gastrointestinal cancer includes, but is not limited to cancers of esophagus [squamous cell carcinoma, adenocarcinoma, leiomyosarcoma, lymphoma], stomach [carcinoma, lymphoma, leiomyosarcoma], pancreas [ductal adenocarcinoma, insulinoma, glucagonoma, gastrinoma, carcinoid tumors, VIPoma], small bowel [adenocarcinoma, lymphoma, carcinoid tumors, Kaposi's sarcoma, leiomyoma, hemangioma, lipoma, neurofibroma, fibroma], and large bowel [adenocarcinoma, tubular adenoma, villous adenoma, hamartoma, leiomyoma].

In certain embodiments, a compound is used to treat a subject suffering from a cancer of the genitourinary tract expressing a GLI polypeptide, such as a GLI1, GLI2, or GLI3 polypeptide. Cancers of the genitourinary tract include, but are not limited to cancers of kidney [adenocarcinoma, Wilms tumor (nephroblastoma), lymphoma, leukemia, renal cell carcinoma], bladder and urethra [squamous cell carcinoma, transitional cell carcinoma, adenocarcinoma], prostate [adenocarcinoma, sarcoma], and testis [seminoma, teratoma, embryonal carcinoma, teratocarcinoma, choriocarcinoma, sarcoma, Leydig cell tumor, fibroma, fibroadenoma, adenomatoid tumors, lipoma].

In certain embodiments, a compound is used to treat a subject suffering from a liver cancer expressing a GLI polypeptide, such as a GLI1, GLI2, or GLI3 polypeptide. A liver cancer includes, but is not limited to, hepatocellular carcinoma, cholangiocarcinoma, hepatoblastoma, angiosarcoma, hepatocellular adenoma, and hemangioma.

In certain embodiments, a compound is used to treat a subject suffering from a skin cancer expressing a GLI polypeptide, such as a GLI1, GLI2, or GLI3 polypeptide. Skin cancer includes, but is not limited to, malignant melanoma, basal cell carcinoma, squamous cell carcinoma, Kaposi's sarcoma, nevi, dysplastic nevi, lipoma, angioma, dermatofibroma, keloids, and psoriasis.

In certain embodiments, a compound is used to treat a subject suffering from a gynecological cancer expressing a GLI polypeptide, such as a GLI1, GLI2, or GLI3 polypeptide. Gynecological cancers include, but are not limited to, cancer of uterus [endometrial carcinoma], cervix [cervical carcinoma, pre-invasive cervical dysplasia], ovaries [ovarian carcinoma (serous cystadenocarcinoma, mucinous cystadenocarcinoma, endometrioid carcinoma, clear cell adenocarcinoma, unclassified carcinoma), granulosa-theca cell tumors, Sertoli-Leydig cell tumors, dysgerminoma, malignant teratoma and other germ cell tumors], vulva [squamous cell carcinoma, intraepithelial carcinoma, adenocarcinoma, fibrosarcoma, melanoma], vagina [clear cell carcinoma, squamous cell carcinoma, sarcoma botryoides (embryonal rhabdomyosarcoma), and fallopian tubes [carcinoma].

In certain embodiments, a compound is used to treat a subject suffering from a bone cancer expressing a GLI polypeptide, such as a GLI1, GLI2, or GLI3 polypeptide. Bone cancer includes, but is not limited to, osteogenic sarcoma [osteosarcoma], fibrosarcoma, malignant fibrous histiocytoma, chondrosarcoma, Ewing's sarcoma, malignant lymphoma [reticulum cell sarcoma], multiple myeloma, malignant giant cell tumor, chordoma, osteochondroma [osteocartilaginous exostoses], benign chondroma, chondroblastoma, chondromyxoid fibroma, osteoid osteoma, and giant cell tumors.

In certain embodiments, a compound is used to treat a subject suffering from a cancer of the nervous system expressing a GLI polypeptide, such as a GLI1, GLI2, or GLI3 polypeptide. Cancers of the nervous system include, but are not limited to cancers of skull [osteoma, hemangioma, granuloma, xanthoma, Paget's disease of bone], meninges [meningioma, meningiosarcoma, gliomatosis], brain [astrocytoma, medulloblastoma, glioma, ependymoma, germinoma (pinealoma), glioblastoma multiforme, oligodendroglioma, schwannoma, retinoblastoma, congenital tumors], and spinal cord [neurofibroma, meningioma, glioma, sarcoma].

In certain embodiments, a compound is used to treat a subject suffering from a hematologic cancer expressing a GLI polypeptide, such as a GLI1, GLI2, or GLI3 polypeptide. Hematologic cancers include, but are not limited to cancer of blood [myeloid leukemia (acute and chronic), acute lymphoblastic leukemia, chronic lymphocytic leukemia, myeloproliferative diseases, multiple myeloma, myelodysplastic syndrome], Hodgkin's disease, and non-Hodgkin's lymphoma (malignant lymphoma).

In certain embodiments, a compound is used to treat a subject suffering from a cancer of adrenal glands expressing a GLI polypeptide, such as a GLI1, GLI2, or GLI3 polypeptide. A cancer of adrenal glands includes, but is not limited to, neuroblastoma.

The disclosure provides a method for treatment or prevention of a cancer wherein a GLI polypeptide, such as a GLI1, GLI2, or GLI3 polypeptide is expressed. In certain embodiments, this method comprises the step of administering to a patient a pharmaceutical composition. Such pharmaceutical composition comprises, for example, a compound of formula (I). In certain embodiments, the compound is Compound 1. In certain embodiments, the compound is Compound 4. In certain embodiments, the compound is Compound 2. In certain embodiments, the compound is Compound 6. In certain embodiments, the compound is Compound 3. In certain embodiments, the compound is Compound 5.

Pharmaceutical compositions of the embodiments are administered alone or in combination with one or more additional therapeutic compound or treatments. Examples of such therapeutic compounds or treatments include, but are not limited to, taxol, cyclophosphamide, tamoxifen, fluorouracil and doxorubicin. In certain embodiments, a pharmaceutical composition or medicament comprises a compound of the embodiments and another therapeutic agent selected from erlotinib (Tarceva®), pemetrexed (Alimta®), LY294002, SB431542, and cisplatin. In addition, other chemotherapeutic agents are described herein.

Methods for treating cancer may optionally comprise one or more of the following steps: obtaining a biological sample of tissue or fluid from an individual; screening the biological sample for the expression of a GLI polypeptide, such as a GLI1, GLI2, or GLI3 polypeptide, for example by contacting the biological sample with an antibody directed to GLI1, GLI2, or GLI3; or screening the biological sample for expression of a Gli1, Gli2, or Gli3 polynucleotide, for example by detecting a Gli1, Gli2, or Gli3 mRNA.

Many cancers are initially treated using chemotherapeutic agents as described herein. However, very often, cancers develop resistance against such chemotherapeutic agents which then are not longer effective. Thus, in one embodiment, the cancer is a multi-drug resistant cancer or a cancer that is otherwise refractory to treatment. Therefore, in certain embodiments, a compound of the embodiments is used to overcome resistance to chemotherapeutic agents in tumor cells. This method comprises the step of administering to a tumor cell resistant to at least one chemotherapeutic agent, a compound of the embodiments, wherein the administering results in subsequent tumor cell death. In certain embodiments, the compound is Compound 1. In certain embodiments, the compound is Compound 4. In certain embodiments, the compound is Compound 2. In certain embodiments, the compound is Compound 6. In certain embodiments, the compound is Compound 3. In certain embodiments, the compound is Compound 5.

In a certain embodiment, a compound of the embodiments for use in the treatment of a cancer is provided. In certain embodiments, the disclosure provides the use of a compound of the embodiments in the manufacture of a pharmaceutical composition or a medicament for the therapeutic and/or prophylactic treatment of a condition, e.g., cancer wherein a GLI polypeptide is expressed.

In certain embodiments, the disclosure provides for the use of a compound in the manufacture of a pharmaceutical composition or medicament for use in combination with another chemotherapeutic anticancer agent for the treatment of a cancer expressing a GLI polypeptide. Pharmaceutical composition and medicaments provided by the disclosure are described herein.

Kits

For use in diagnostic, research, and therapeutic applications suggested above, kits are also provided by the disclosure. In the diagnostic and research applications such kits may include any or all of the following: assay reagents, buffers, a compound of the embodiments, a GLI polypeptide, a Gli nucleic acid, an anti-GLI antibody, hybridization probes and/or primers, Gli expression constructs, etc. A therapeutic product may include sterile saline or another pharmaceutically acceptable emulsion and suspension base.

In addition, the kits may include instructional materials containing directions (i.e., protocols) for the practice of the methods of the embodiments. The instructions may be present in the subject kits in a variety of forms, one or more of which may be present in the kit. While the instructional materials typically comprise written or printed materials they are not limited to such. Any medium capable of storing such instructions and communicating them to an end user is contemplated. Such media include, but are not limited to electronic storage media (e.g., magnetic discs, tapes, cartridges, chips, flash memory), optical media (e.g., CD-ROM, DVD, Blu-ray), and the like. Such media may include addresses to internet sites that provide such instructional materials.

A wide variety of kits and components can be prepared according to the embodiments, depending upon the intended user of the kit and the particular needs of the user.

In certain embodiments, the kit is a pharmaceutical kit and comprises a pharmaceutical composition comprising (i) a small molecule compound of the embodiments and (ii) a pharmaceutical acceptable carrier. Pharmaceutical kits optionally comprise an instruction stating that the pharmaceutical composition can or should be used for treating a cancer expressing a GLI polypeptide or Gli nucleic acid.

Additional kit embodiments include optional functional components that would allow one of ordinary skill in the art to perform any of the method variations described herein.

Additional aspects of embodiments of the subject compositions, pharmaceutical preparations and methods are found in PCT/US12/47689, filed Jul. 20, 2012, which claims priority to U.S. Provisional Patent Application No. 61/510,176, filed Jul. 21, 2011, the disclosures of each of which are incorporated herein by reference in their entirety.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1: General Methods

A. Cell Lines

Most human cell lines were obtained from the American Type Culture Collection (A.T.C.C.; Manassas, Va.). These cell lines include: non-small cell lung cancer (NSCLC) cells A549, H1703, H460, H358, H322, H838, H1299, H1650, H1975, H522, H441, H1666, H2170, H820, HCC2935, HCC4006, and A427; mesothelioma cells 211H, H513, H2052, H28, and H2452; colon cancer cells SW480, HCT116, HT29, Lovo, DLD-1, COLO-205, COLO-201, and CaCO2; breast cancer cells MCF7, HuL100, HCC1569, SKBR-3 and BT474; pancreatic cancer cells Panc-1, Panc 02.13, HPAF-II, SW1990, Ypac, 8902-1, and 8988-1; melanoma cells LOX, A375, A2058, Calu, Calv6, HA-A, AS2504, Mel202, MaMel144, SK-Mel-2, SK-Mel-5, SK-Mel-28, SK-Mel-3, SK-Mel-24, SK-Mel-30, and MelJuso; multiple myeloma cells PRMI-8226, H929, MM1.R, and U266; prostate cancer cell line LnCAP and DU145; normal lung fibroblast cell MRCS. Other human mesothelioma cancer cell lines H290 and MS-1 were obtained from the National Institute of Health (NIH, Frederick, Md.), and REN was kindly provided by Dr. Steven Albelda's laboratory at the University of Pennsylvania (Philadelphia, Pa.). Human pancreatic cancer cell lines BxPC3, Panc4.21, and CFPAC-1 were kindly provided by Dr. Matthias Hebrok's laboratory at the University of California, San Francisco (San Francisco, Calif.). Human gastric cancer cell lines, MNK28, and AGS were kindly provided by Dr. Xin Chen at the University of California, San Francisco (San Francisco, Calif.); esophageal cancer cell lines OE19, TE-7, OE31, and OE21 were kindly provided by Dr. Michael Korn at the University of California, San Francisco, (San Francisco, Calif.).

B. Tissue Samples

Fresh cancer tissue and adjacent normal tissue from patients undergoing curative primary resection of their tumors were collected at the time of surgery (IRB approval H8714-15319-040), and immediately snap-frozen in liquid nitrogen. These tissue samples were kept at −170° C. in a liquid nitrogen freezer until further use. Primary tissue cultures were prepared as follows: Fresh cancer tissue was obtained with consent from patients undergoing resection, cut into small pieces (1-2 mm in diameter), and then digested with Collagenase A (Roche Applied Science, Indianapolis, Ind.) at room temperature for 2 hours according to manufacturer's protocol. Single cells from the digestion were spun down and the cell pellets were washed twice using RPMI 1640 supplemented with 10% fetal bovine serum, penicillin (100 IU/ml) and streptomycin (100 µg/ml). Then, the cells were resuspended in the same medium and cultured in 6-well plates at 37° C. in a humid incubator with 5% $CO_2$ until they were ready for further treatments.

C. Cell Survival Assay (Cell-Based Cytotoxicity Assay)

Typically, the compounds of the embodiments were dissolved in DMSO at a concentration of 30 mM. The compounds were then tested under cell culture conditions at different concentrations ranging from 0, 10, 30, 50, to 100 µM. To determine cell survival after treatment, the cells were incubated with the compounds in 6-well plates for about 3 days. After removal of the cell culture medium, 1-ml of 0.5% crystal violet solution (prepared in 20% ethanol and 20% methanol) was added to stain the cells for 5 min. Then the crystal violet solution was rinsed clean with tap water. Cell survival was estimated based on the density of crystal stained plates.

Another assay for determining the number of viable cells in proliferation or cytotoxicity assays is the MTS assay, a colorimetric method. MTS assay reagents are commercially available (Promega Corp., Madison, Wis.). The reagent contains a tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine ethosulfate; PES). PES has enhanced chemical stability, which allows it to be combined with MTS to form a stable solution. The MTS tetrazolium compound (Owen's reagent) is bioreduced by cells into a colored formazan product that is soluble in tissue culture medium. This conversion may be accomplished by NADPH or NADH produced by dehydrogenase enzymes in metabolically active cells. The quantity of formazan product as measured by the absorbance at 490 nm is directly proportional to the number of living cells in culture. Because the MTS formazan product is soluble in tissue culture medium, this assay requires fewer steps than procedures that use tetrazolium compounds such as MTT. The formazan product of MTT reduction is a crystalline precipitate that requires an additional step in the procedure to dissolve the crystals before recording absorbance readings at 570 nm.

D. Quantitative RT-PCR

Total RNA was isolated using Qiagen RNeasy Mini Kit (Valencia, Calif.). Hybridization probes and primers (Table 1) were purchased from Applied Biosystems (ABI, Foster City, Calif.). cDNA synthesis and Taqman® PCR were performed according to the manufactures' protocols. The gene expression was assayed in triplicate in ABI 7300 Real-time PCR System. Samples were normalized to their housekeeping gene GAPDH and then calculated by using $2^{-dct}$ method.

TABLE 1

Hybridization probes and primers for quantitative RT-PCR

| Gene | Hybridization probes and primers (Product numbers from Applied Biosystems, referring to Taqman ® PCR assay mixtures for the listed gene.) |
| --- | --- |
| Gli1 | Hs01110776_g1 |
| Gli2 | Hs01119974_m1 |
| Gli3 | Hs00609233_m1 |
| Axin2 | Hs00610344_m1 |
| EGFR | Hs01076078_m1 |
| Wnt-2 | Hs00608224_m1 |
| HHIP | Hs01011015_m1 |
| Cyclin D1 | Hs99999004_m1 |

E. In Vivo Anti-Tumorigenicity Studies

The administered compounds were tested in vivo in the mouse xenograft model bearing human cancer cells. Briefly, female athymic nude mice strain NCRNU-M (5-10 weeks old, 20-25 grams in weight; Taconic, Germantown, N.Y.) was maintained in pathogen-free conditions. Three human cancer cell lines: NSCLC A549, melanoma MelJuso, and mesothelioma MS-1 were used. Five or ten mice were used in each group and injected s.c. with $3 \times 10^6$ cancer cells in the dorsal area in a volume of 100 µl. After inoculation, human cancer cells were allowed to grow in mice for 10-13 days to become visible tumor nodules. Animals were then injected with a compound of the embodiments at a dose of 50 mg/kg body weight (1 mg/mouse per day). Vehicle alone was used as control. The compounds and controls were adjusted in 40 ul volume for i.p. injection in the abdomens of the mice. Injections were performed daily around the same time for 14 days. Tumors were allowed to grow for 1-2 additional weeks after completion of the compound treatments. Tumor size was measured every three to four days, and tumor volumes were calculated using width (x) and length (y) ($x^2y/2$, where x<y). Throughout this period, general toxicity of the treatments was also monitored by measuring body weight of the mice. Data was presented as mean values (±S.D.).

F. Pharmacokinetics (PK) Study of Compounds in Mice

Mice (three per group) were either i.v. injected or orally administered with each of the compounds at a dose of 10 mg/kg body weight. Then plasma was collected from the tail-vein of each mouse at 20 min, 1 hour, 3 hours, 10 hours and 24 hours after injection or oral administration (PO). The compound concentrations in each plasma sample were determined by Mass Spec to confirm the compound absorption into the blood stream of the mice.

G. Histological Examination for Toxicity Evaluation

After the in vivo studies were completed, different organs were resected from mice. These organs included liver, lung, heart, kidney, intestines, ovary, brain, spleen, skin, and muscle. The specimens were fixed in 4% buffered formaldehyde, embedded in paraffin, sectioned, and histologically analyzed by hematoxylin and eosin (HE) staining. The HE stained slides were examined by a mouse pathologist for toxicity evidence from all the organs as compared with vehicle controls. In addition, leukocytes (WBC: white blood cell, NE: neutrophil, LY: lymphocyte, MO: monocyte, EO: eosinophil, BA: basophil) from each animal from all treatment groups were collected and leukocyte population was counted through a blood cell counter.

H. Statistical Analysis

Data shown represent mean values (+S.D.). Unpaired T-Test in the Excel was used for comparing different treatments and cell lines.

I. Preparation of Small Molecule Compounds

Unless otherwise noted, reagents and solvents were used as received from commercial suppliers. Proton and carbon nuclear magnetic resonance spectra were obtained on a on a Bruker AVANCE spectrometer at 400 MHz for proton. Spectra are given in ppm (δ) and coupling constants, J, are reported in Hertz. The solvent peak was used as the reference peak for proton spectra. LC-MS spectra were obtained on Agilent 1100 HPLC LC-MS ion trap electrospray ionization (ESI) mass spectrometer.

Example 2: Synthesis of Compound 1

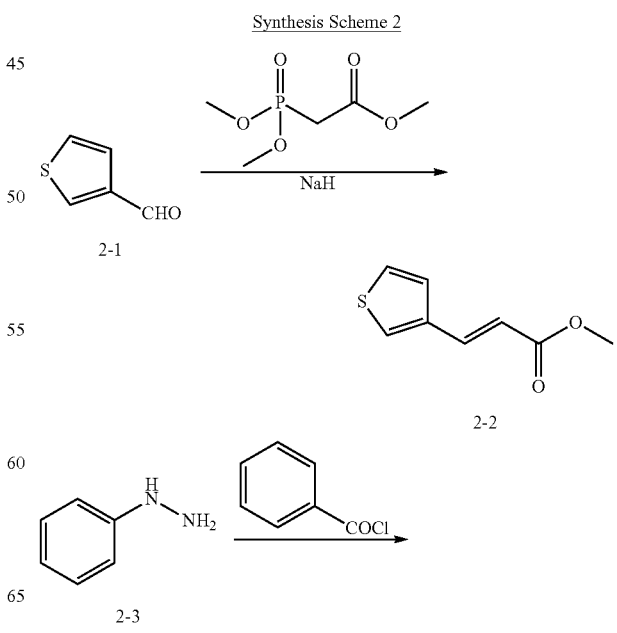

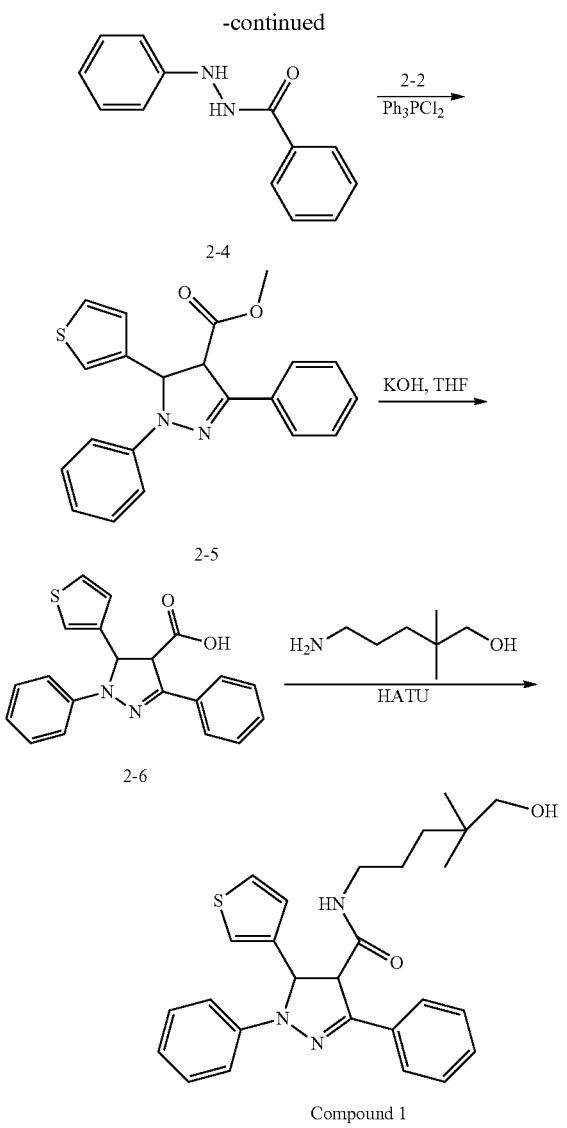

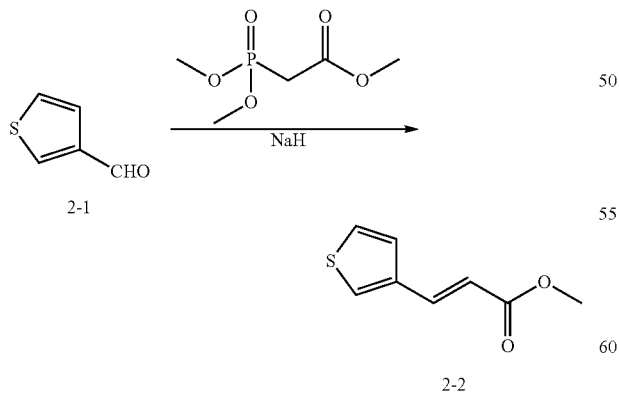

A. Preparation of Compound 2-2

To a mixture of 60% NaH (37 g, 0.93 mol) in 500 mL dry THF was added methyl 2-(dimethoxyphosphoryl)acetate (102 g, 0.56 mol). Then a solution of Compound 2-1 (41 g, 0.37 mol) in 100 mL dry THF was added to this mixture. The reaction mixture was stirred for 12 hours at room temperature. To the reaction mixture was added saturated aqueous NH₄Cl. The resulting mixture was concentrated and extracted with ethyl acetate (3×50 mL). The organic phase was washed with water (3×25 mL), brine (3×25 mL), dried with anhydrous Na₂SO₄ and dried in vacuo to give a crude product. The residue was purified with column chromatography (ethyl acetate in petroleum ether 10% v/v) to give Compound 2-2 (30 g, Yield: 48%) as a clear liquid. m/z: 169 [M+H]

B. Preparation of Compound 2-4

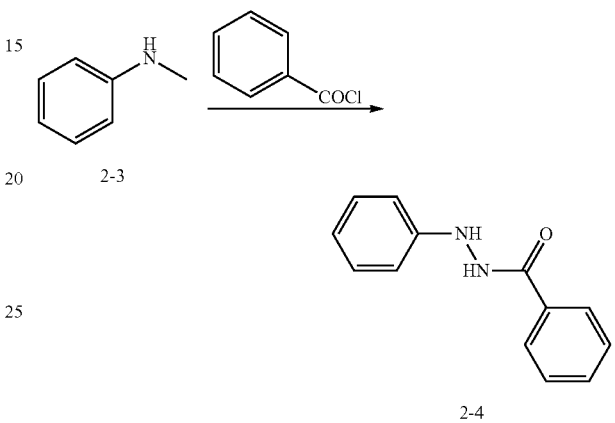

To a mixture of Compound 2-3 (121 g, 0.64 mol), pyridine (101 g, 1.28 mol) in 400 mL CH₂Cl₂ was added a solution of benzoyl chloride (90 g, 0.64 mol) in 100 ml CH₂Cl₂ at room temperature. The reaction mixture was stirred for 12 hours. The reaction mixture was washed with water (4×50 mL), dried with anhydrous Na₂SO₄ and dried in vacuo. The residue was recrystallized with ethyl acetate to give Compound 2-4 (72 g, Yield 52%) as a white solid. m/z: 213[M+H]⁺.

C. Preparation of Compound 2-5

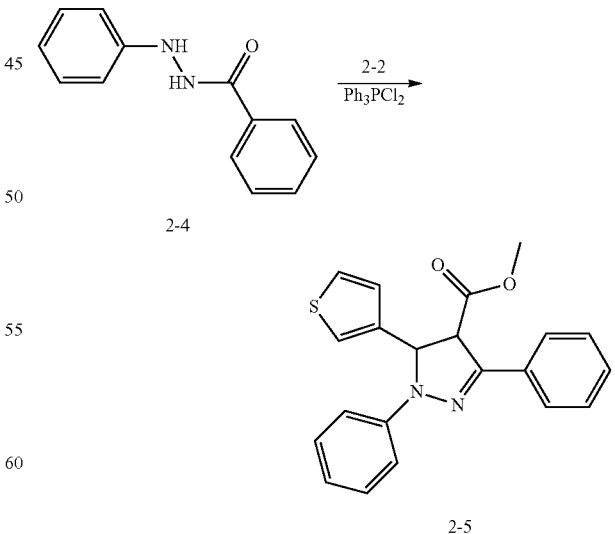

To a solution of Compound 2-4(15 g, 72 mmol) and Compound 2-2 (13 g, 79 mmol) and Ph₃PCl₂ (48 g, 144 mmol) in CH₂Cl₂ (250 mL) was added Et₃N (36 g, 360 mmol) at room temperature. The reaction mixture was stirred for 12 hours at room temperature. The reaction mixture was washed with water (3×30 mL), brine (3×30 mL), dried with anhydrous Na$_2$SO$_4$ and dried in vacuo. The residue was purified with column chromatography (ethyl acetate in petroleum ether 1% v/v) to give Compound 2-5 (10 g, Yield: 38%) as a yellow solid. m/z: 363 [M+H]$^+$.

D. Preparation of Compound 2-6

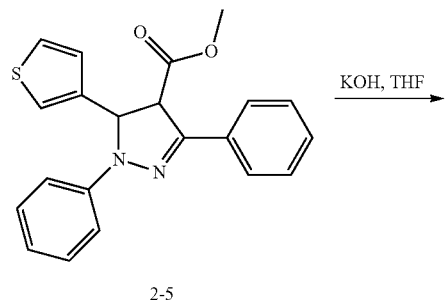

To a solution of Compound 2-5 (10 g 28 mmol) in THF (150 mL) was added KOH (4.7 g, 84 mmol) in water (80 mL) and the reaction mixture was stirred for 12 hours at room temperature. The reaction mixture was adjusted pH value to 6 with 1N HCl and concentrated, extracted with ethyl acetate (4×30 mL). The organic phase was washed with water (2×20 mL), brine (2×20 mL) dried with anhydrous Na$_2$SO$_4$ and dried in vacuo to give crude Compound 2-6 (9.0 g, Yield: 92%) as a yellow solid. m/z: 349[M+H]$^+$.

E. Preparation of Compound 1

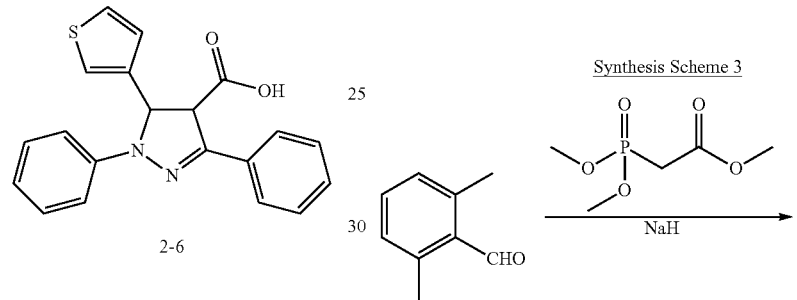

A mixture of Compound 2-6 (9.0 g, 26 mmol), 5-amino-2,2-dimethylpentan-1-ol (5.1 g, 39 mmol), Et$_3$N (5.2 g, 52 mmol), and O-(7-Aza-1H-benzotriazol-1-yl)-N,N,N',N'-tetramethyluronium hexafluorophosphate (HATU, 14.8 g, 39 mmol), in CH$_2$Cl$_2$ was stirred for 12 hours at room temperature. The reaction mixture was washed with water (3×20 mL), brine (2×20 mL), dried with anhydrous Na$_2$SO$_4$ and dried in vacuo. The residue was purified by column chromatography (ethyl acetate in petroleum ether 25% v/v) to give Compound 1 (6.0 g, Yield: 50%) as a white solid.

$^1$H NMR (400 MHz, CDCl$_3$-d$_1$) δ 7.71 (m, 2H), 7.35~7.30 (m, 5H), 7.23 (q, J=3.2, 1H), 7.14 (d, J=8.0, 2H), 7.09 (dd, J$_1$=2.8 J$_2$=0.8, 1H), 6.94 (m, 2H), 6.38 (t, J=5.6, 1H), 4.96 (d, J=4.8, 1H), 4.49 (d, J=4.4, 1H), 3.33 (m, 1H), 3.10 (s, 2H), 3.15 (m, 1H), 1.42~1.35 (m, 2H), 1.1~11.06 (m, 2H), 0.74 (d, J=2.4, 6H). m/z: 462 [M+H]$^+$

Example 3: Synthesis of Compound 3

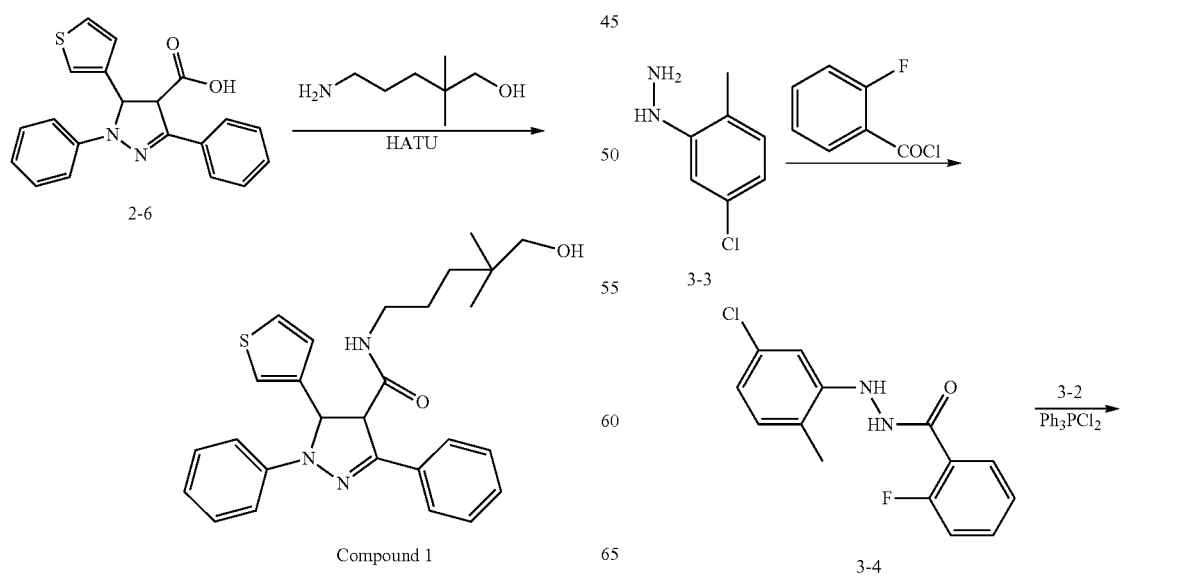

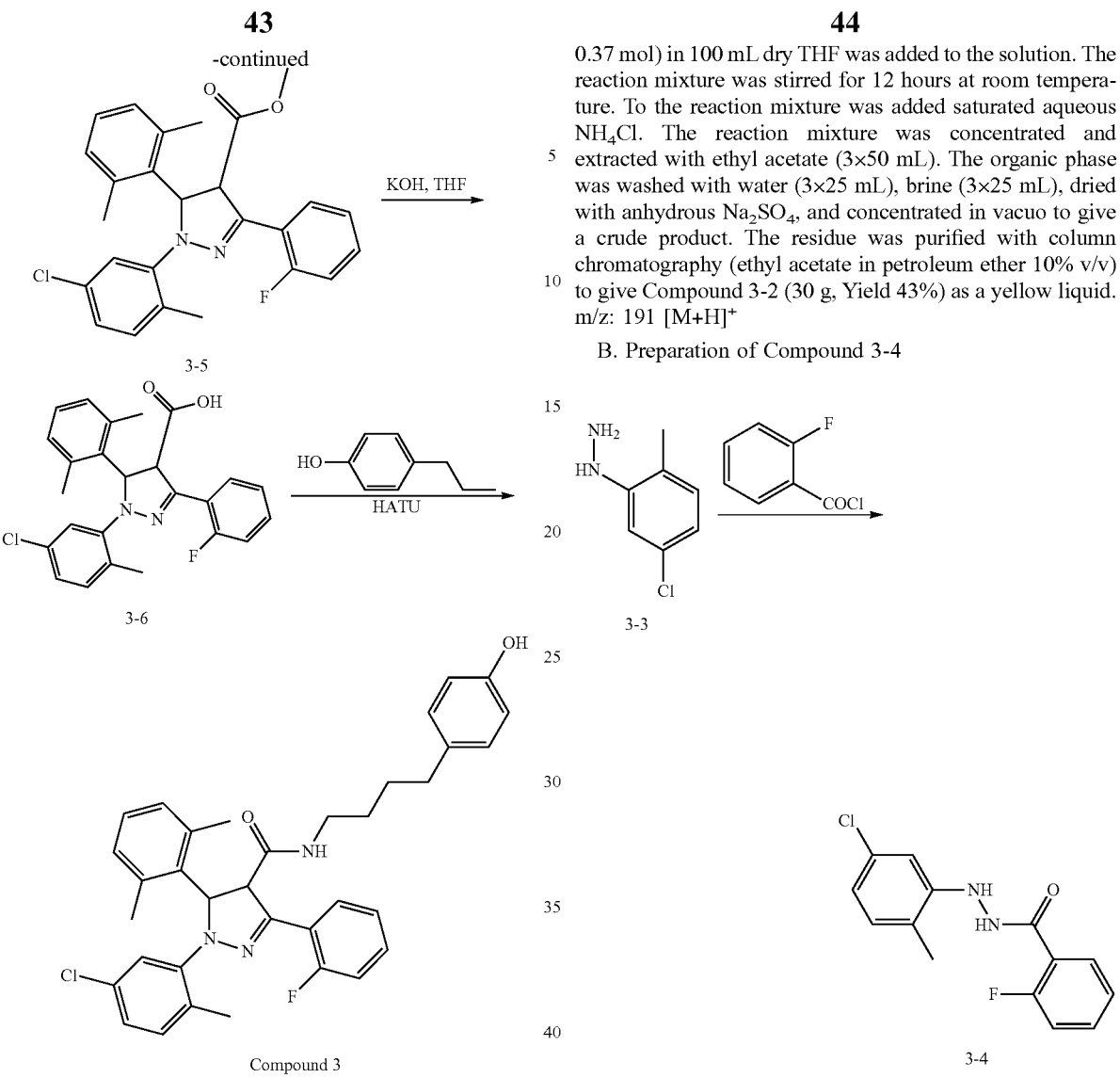

0.37 mol) in 100 mL dry THF was added to the solution. The reaction mixture was stirred for 12 hours at room temperature. To the reaction mixture was added saturated aqueous NH₄Cl. The reaction mixture was concentrated and extracted with ethyl acetate (3×50 mL). The organic phase was washed with water (3×25 mL), brine (3×25 mL), dried with anhydrous Na₂SO₄, and concentrated in vacuo to give a crude product. The residue was purified with column chromatography (ethyl acetate in petroleum ether 10% v/v) to give Compound 3-2 (30 g, Yield 43%) as a yellow liquid. m/z: 191 [M+H]⁺

B. Preparation of Compound 3-4

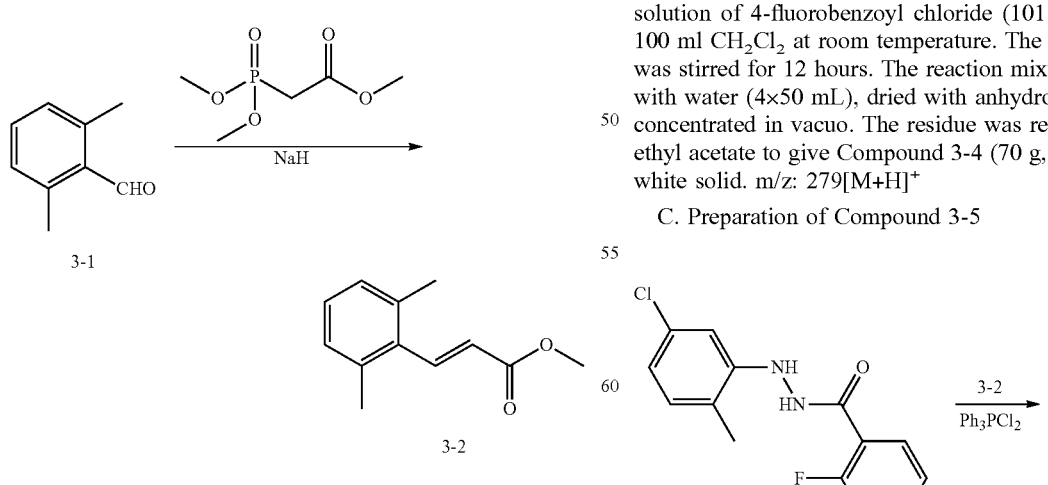

To a mixture of Compound 3-3 (100 g, 0.64 mol) and pyridine (101 g, 1.28 mol) in 400 mL CH₂Cl₂ was added a solution of 4-fluorobenzoyl chloride (101 g, 0.64 mol) in 100 ml CH₂Cl₂ at room temperature. The reaction mixture was stirred for 12 hours. The reaction mixture was washed with water (4×50 mL), dried with anhydrous Na₂SO₄, and concentrated in vacuo. The residue was recrystallized with ethyl acetate to give Compound 3-4 (70 g, Yield 39%) as a white solid. m/z: 279[M+H]⁺

C. Preparation of Compound 3-5

A. Preparation of Compound 3-2

To a solution of 60% NaH (37 g, 0.93 mol) in 500 mL dry THF was added methyl 2-(dimethoxyphosphoryl)acetate (102 g, 0.56 mol). Then a solution of Compound 3-1 (50 g, -continued

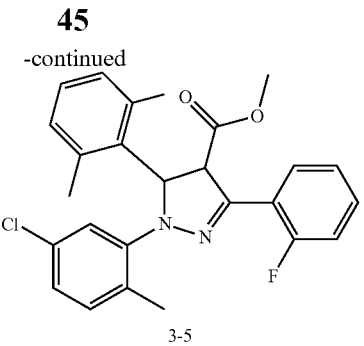

3-5

To a solution of Compound 3-4 (20 g, 72 mmol) and Compound 3-2 (15 g, 79 mmol) and Ph₃PCl₂ (48 g, 144 mmol) in CH₂Cl₂ (250 mL) was added Et₃N (36 g, 360 mmol) at room temperature. This reaction mixture was stirred for 12 hours at room temperature. The reaction mixture was washed with water (3×30 mL), brine (3×30 mL), dried with anhydrous Na₂SO₄, and concentrated in vacuo. The residue was purified with column chromatography (ethyl acetate in petroleum ether 1% v/v) to give Compound 3-5 (10 g, Yield 31%) as a yellow solid. m/z: 451 [M+H]⁺

D. Preparation of Compound 3-6

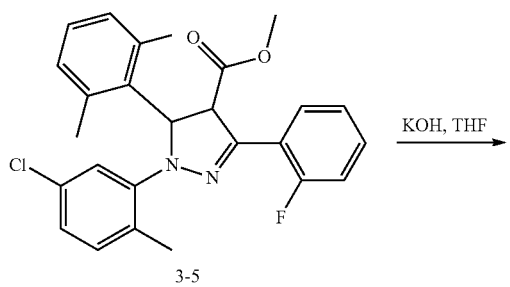

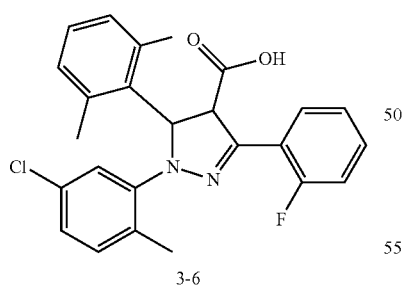

3-6

To a solution of Compound 3-5 (10.0 g 22 mmol) in THF (150 mL) was added KOH (3.7 g, 67 mmol) in water (60 mL). The reaction mixture was stirred for 12 hours at room temperature. The reaction mixture was adjusted pH value to 6 with 1N HCl and concentrated, and extracted with ethyl acetate (4×30 mL). The organic phase was washed with water (2×20 mL), brine (2×20 mL), dried with anhydrous Na₂SO₄, and concentrated in vacuo to give crude Compound 3-6 (8.0 g, Yield: 83%) as a yellow solid. m/z: 437[M+H]⁺

E. Preparation of Compound 3

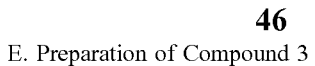

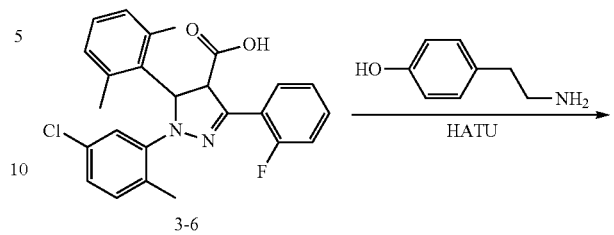

3-6

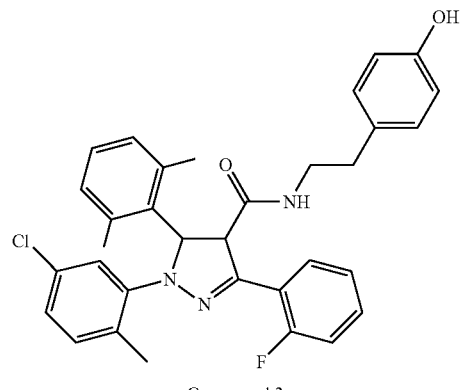

Compound 3

A mixture of Compound 3-6 (8.0 g, 18 mmol), 4-(2-aminoethyl)phenol (3.7 g, 27 mmol), Et₃N (3.6 g, 36 mmol) 0-(7-Aza-1H-benzotriazol-1-yl)-N,N,N',N'-tetramethyluronium hexafluorophosphate (10.3 g, 27 mmol), in CH₂Cl₂ was stirred for 12 hours at room temperature. The reaction mixture was washed with water (3×20 mL), brine (2×20 mL), dried with anhydrous Na₂SO₄, and concentrated in vacuo. The residue was purified by column chromatography (ethyl acetate in petroleum ether 25% v/v) to give Compound 3 (5.0 g, Yield: 50%) as a white solid.

¹H NMR (400 MHz, CDCl₃-d₁) δ 7.56 (td, J₁=7 0.6, J₂=2 0.0, 1H), 7.26~7.20 (m, 1H), 7.14 (d, J=7.6, 1H), 7.07~6.90 (m, 6H), 6.83 (d, J=6.8, 1H), 6.79 (d, J=8.8, 2H), 6.12 (t, J=5.6, 1H), 5.34 (dd, J1=10.4, J2=1.6, 1H), 4.98 (s, 1H), 4.77 (d, J=10.4, 1H), 3.55 (m, 1H), 3.43 (m, 1H), 2.70~2.54 (m, 2H), 2.43 (s, 3H), 2.40 (s, 3H), 2.10 (s, 3H). m/z: 556 [M+H]⁺

Example 4: Synthesis of Compound 4

Synthesis Scheme 4

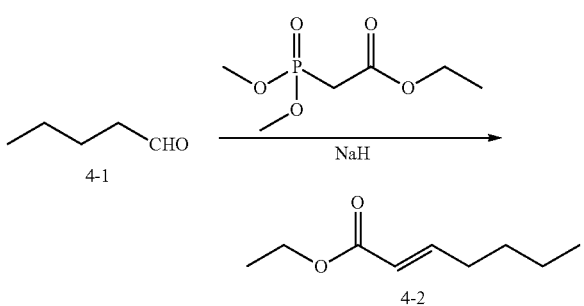

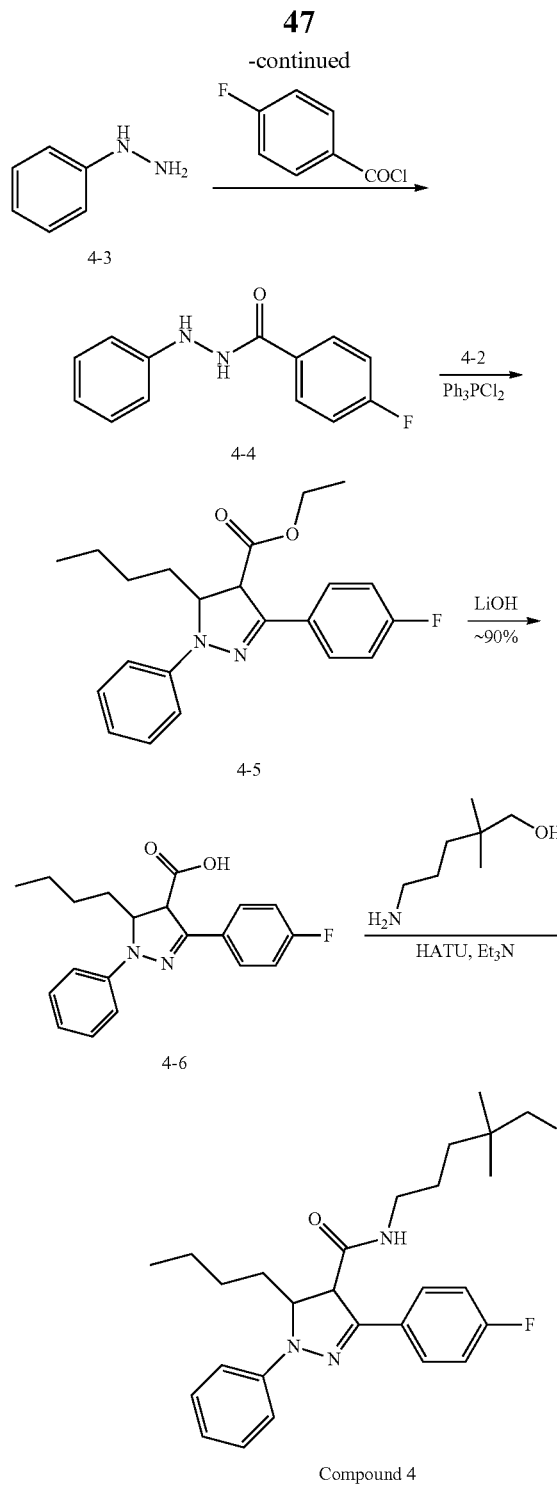

Compound 4

A. Preparation of Compound 4-2

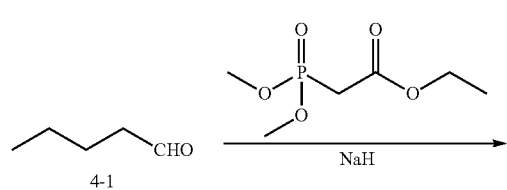

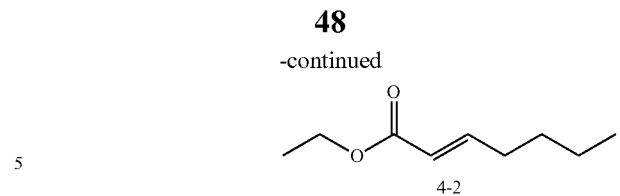

To a solution of 60% NaH (34.8 g, 870 mmol) in 500 mL dry THF was added ethyl 2-(dimethoxyphosphoryl)acetate (102 g, 522 mmol). Then a solution of Compound 4-1 (30 g, 348 mmol) in 100 mL dry THF was added to the mixture. The reaction mixture was stirred for 12 hours at room temperature. To the reaction mixture was added saturated aqueous $NH_4Cl$. The reaction mixture was concentrated and extracted with ethyl acetate (3×50 mL). The organic phase was washed with water (3×25 mL), brine (3×25 mL), dried with anhydrous $Na_2SO_4$, and concentrated in vacuo to give a crude product. The residue was purified with column chromatography (ethyl acetate in petroleum ether 10% v/v) to give Compound 4-2 (20 g, Yield 37%) as a yellow liquid. m/z: 157 [M+H]$^+$ B. Preparation of Compound 4-4

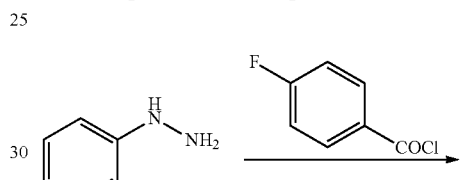

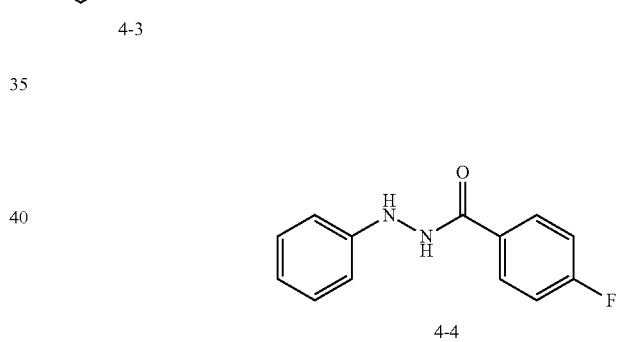

To a mixture of Compound 4-3 (100 g, 0.9 mol) and pyridine (146 g, 1.9 mol) in 400 mL $CH_2Cl_2$ was added a solution of 4-fluorobenzoyl chloride (147 g, 0.9 mol) in 100 ml $CH_2Cl_2$ at room temperature. The reaction mixture was stirred for 12 hours. The reaction mixture was washed with water (4×50 mL), dried with anhydrous $Na_2SO_4$, and concentrated in vacuo. The residue was recrystallized with ethyl acetate to give Compound 4-4 (200 g, Yield 94%) as a white solid. m/z: 231[M+H]$^+$ C. Preparation of Compound 4-5

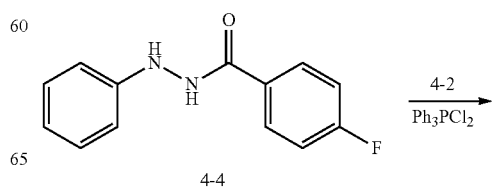

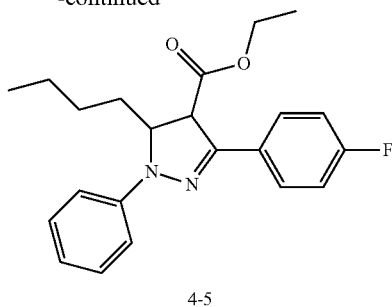

4-5

To a solution of Compound 4-4 (20 g, 87 mmol) and Compound 4-2 (15 g, 96 mmol) and Et₃N (44 g, 435 mmol) in CH₂Cl₂ (250 mL) was added Ph₃PCl₂ (58 g, 174 mmol) at room temperature. The reaction mixture was stirred for 12 hours at room temperature. The reaction mixture was washed with water (3×30 mL), brine (3×30 mL), dried with anhydrous Na₂SO₄, and concentrated in vacuo. The residue was purified with column chromatography (ethyl acetate in petroleum ether 1% v/v) to give Compound 4-5 (9 g, Yield 28%) as a yellow solid. m/z: 369[M+H]⁺

D. Preparation of Compound 4-6

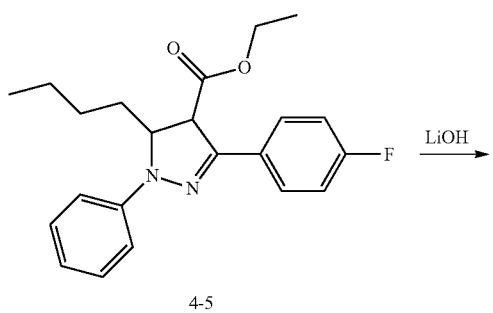

4-5

4-6

To a solution of Compound 4-5 (9.0 g 24 mmol) in THF (150 mL) was added LiOH (4.1 g, 72 mmol) in water (60 mL). The reaction mixture was stirred for 12 hours at room temperature. The reaction mixture was adjusted pH value to 6 with 1N HCl and concentrated, and extracted with ethyl acetate (4×30 mL). The organic phase was washed with water (2×20 mL), brine (2×20 mL), dried with anhydrous Na₂SO₄, and concentrated in vacuo to give crude Compound 4-6 (8.0 g, Yield: 98%) as a yellow solid. m/z: 341[M+H]⁺

E. Preparation of Compound 4

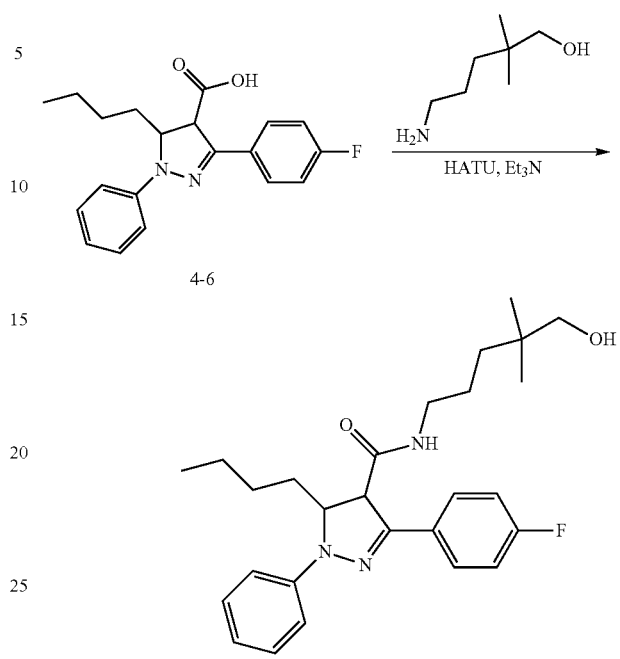

4-6

Compound 4

A mixture of Compound 4-6 (8.0 g, 24 mmol), 5-amino-2,2-dimethylpentan-1-ol (5.3 g, 41 mmol), Et3N (5.4 g, 54 mmol) 0-(7-Aza-1H-benzotriazol-1-yl)-N,N,N',N'-tetramethyluronium hexafluorophosphate (15.4 g, 40.5 mmol), in CH₂Cl₂ was stirred for 12 hours at room temperature. The reaction mixture was washed with water (3×20 mL), brine (2×20 mL), dried with anhydrous Na₂SO₄, and concentrated in vacuo. The residue was purified by column chromatography (ethyl acetate in petroleum ether 25% v/v) to give Compound 4 (6.0 g, Yield: 55%) as a white solid.

¹H NMR (400 MHz, CDCl₃-d₁/D₂O-d₂) δ 7.73 (td, J₁=5.6, J₂=2.4, 2H), 7.32 (t, J=7.6, 2H), 7.11 (t, J=7.8, 4H), 6.93 (t, J=7.2, 1H), 6.35 (m, 1H), 4.34 (d, J=4.4, 1H), 3.70 (m, 1H), 3.30 (m, 1H), 3.17 (s, 2H), 3.08 (m, 1H), 1.81 (m, 1H), 1.54 (m, 1H), 1.39~1.25 (m, 6H), 1.06 (m, 2H), 0.84 (t, J=6.8, 3H), 1.05 (s, 6H). m/z: 454 [M+H]⁺

Example 5: Synthesis of Compound 5

Synthesis Scheme 5

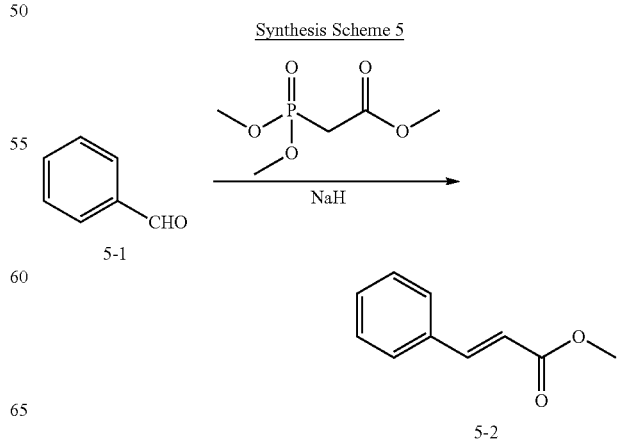

5-1

5-2

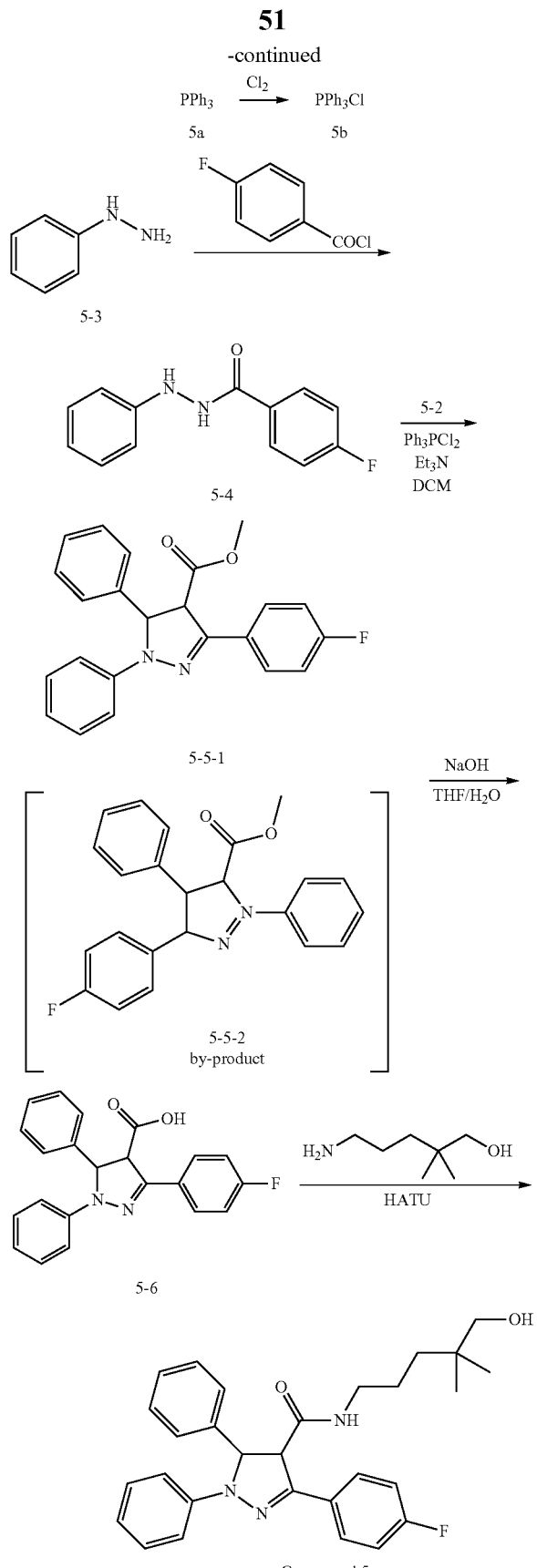

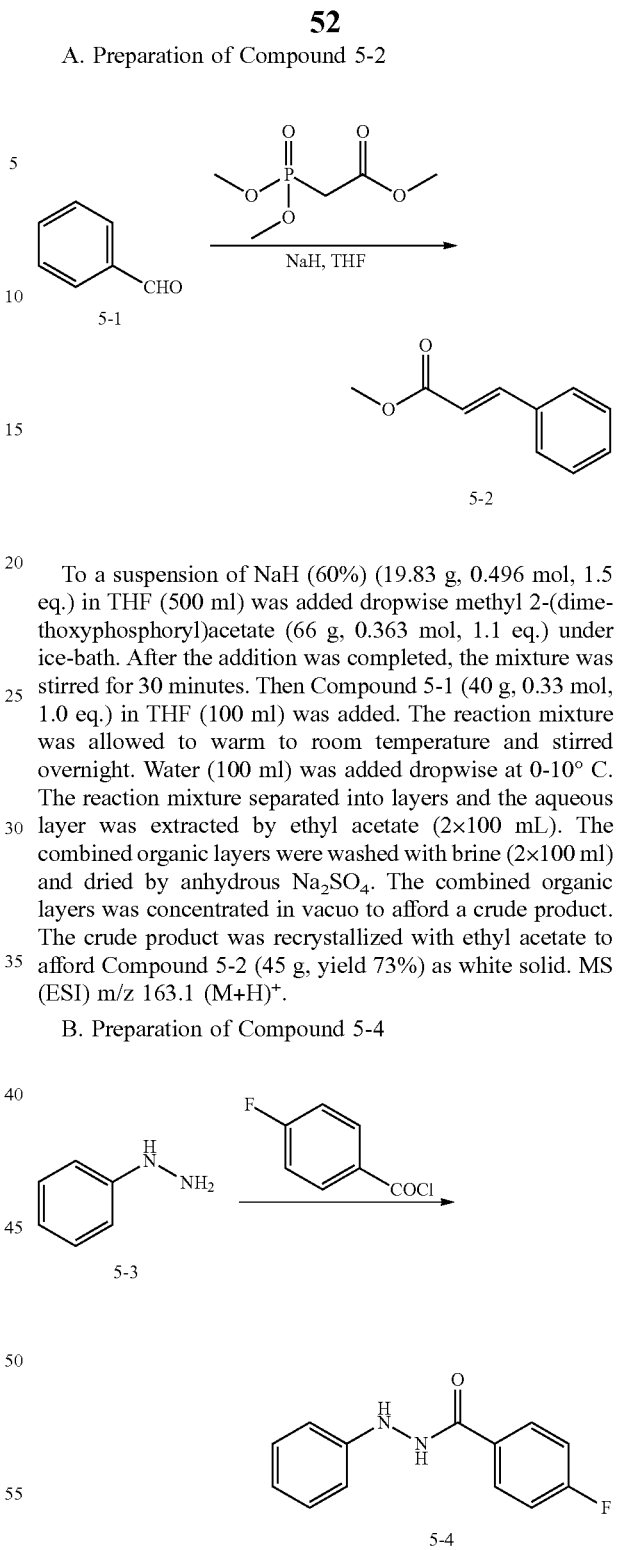

A. Preparation of Compound 5-2

To a suspension of NaH (60%) (19.83 g, 0.496 mol, 1.5 eq.) in THF (500 ml) was added dropwise methyl 2-(dimethoxyphosphoryl)acetate (66 g, 0.363 mol, 1.1 eq.) under ice-bath. After the addition was completed, the mixture was stirred for 30 minutes. Then Compound 5-1 (40 g, 0.33 mol, 1.0 eq.) in THF (100 ml) was added. The reaction mixture was allowed to warm to room temperature and stirred overnight. Water (100 ml) was added dropwise at 0-10° C. The reaction mixture separated into layers and the aqueous layer was extracted by ethyl acetate (2×100 mL). The combined organic layers were washed with brine (2×100 ml) and dried by anhydrous $Na_2SO_4$. The combined organic layers was concentrated in vacuo to afford a crude product. The crude product was recrystallized with ethyl acetate to afford Compound 5-2 (45 g, yield 73%) as white solid. MS (ESI) m/z 163.1 $(M+H)^+$.

B. Preparation of Compound 5-4

Compound 5-3 (100 g, 0.926 mol, 1.0 eq.) and pyridine (110 g, 1.39 mol, 1.5 eq.) in $CH_2Cl_2$ (500 ml) was added 4-fluorobenzoyl chloride (146.3 g, 0.926 mol, 1.0 eq.) in $CH_2Cl_2$ (100 mL). The reaction mixture was stirred for 12 hours. The reaction mixture was washed with water (4×100 ml) and concentrated in vacuo. The residue was recrystallized with ethyl acetate to give Compound 5-4 (150 g, Yield 70%) as a white solid. MS (ESI) m/z 231 $(M+H)^+$.

C. Preparation of Compound 5-5-1

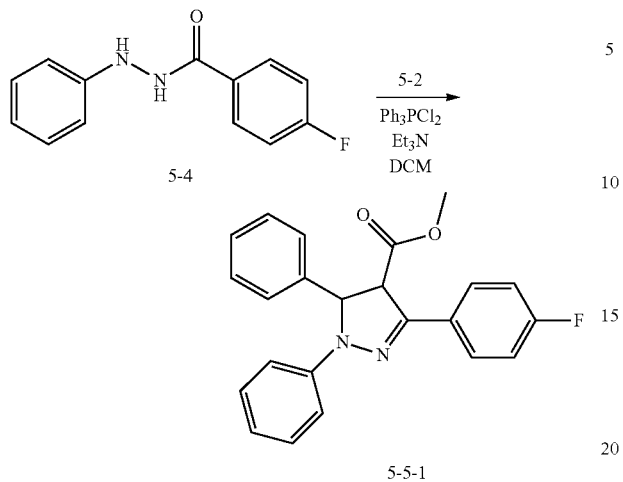

5-5-1

To a solution of Compound 5-4 (20.82 g, 0.091 mol, 1.0 eq.) and Compound 5-2 (16.2 g, 0.10 mol, 1.1 eq.), and Et$_3$N (46.0 g, 0.455 mol, 5.0 eq.) in CH$_2$Cl$_2$ was added Ph$_3$PCl$_2$ (60.4 g, 0.182 mol, 2.0 eq.) at room temperature. The reaction mixture was stirred for 12 hours at room temperature. The reaction mixture was washed with water (3×50 ml), brine (2×50 ml), dried with anhydrous Na$_2$SO$_4$ and concentrated in vacuo. The residue was purified with column chromatography (MeOH:DCM=1:100) to afford Compound 5-5-1 (9 g, yield 26%) as white solid. MS (ESI) m/z 375 (M+H)$^+$.

D. Preparation of Compound 5-6

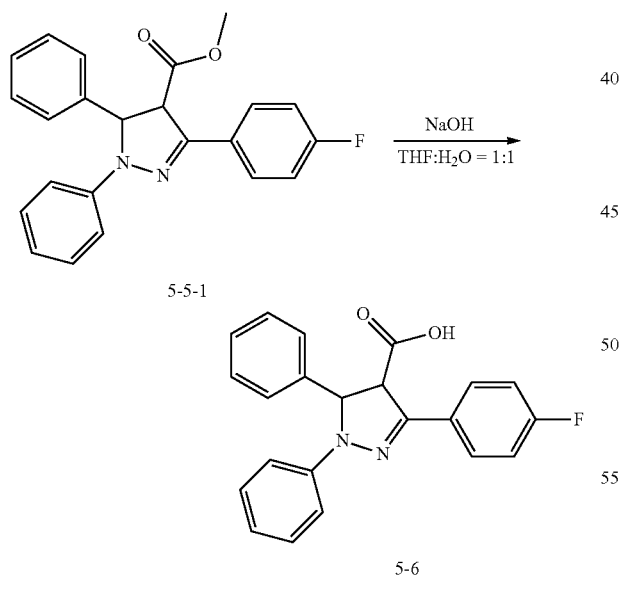

5-6

A mixture of Compound 5-5-1 (9 g, 0.024 mmol, 1.0 eq.) and NaOH (1.93 g, 0.048 mmol, 2.0 eq) in THF (50 ml) and H$_2$O (50 ml) was stirred at room temperature for 4 hours. The reaction mixture was concentrated in vacuo and adjusted pH to 1-2. The reaction mixture was filtered to separate a white solid. The solid was dissolved into CH$_2$Cl$_2$. The solution was washed with brine (2×100 ml) and dried with anhydrous Na$_2$SO$_4$. The solution was concentrated in vacuo to afford Compound 5-6 (7.65 g, yield 88%) as white solid. MS (ESI) m/z 361 (M+H)$^+$.

E. Preparation of Compound 5

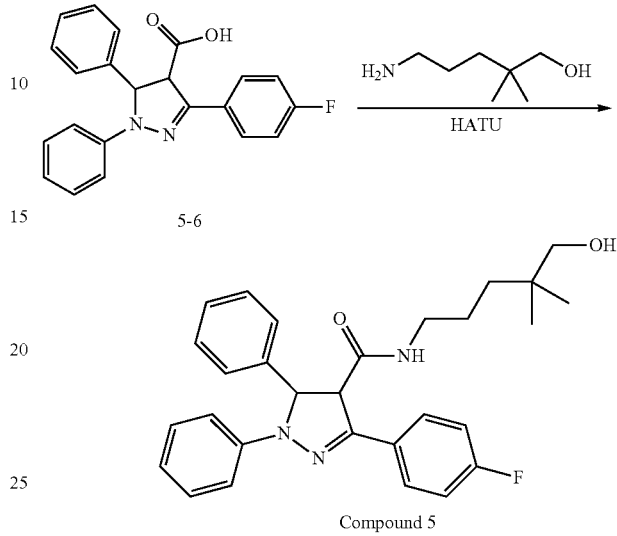

Compound 5

To a solution of Compound 5-6 (9 g, 0.025 mol, 1.0 eq.), o-(7-Azabenzotriazol-1-yl)-N,N,N\N'-tetramethyluronium hexafluorophosphate (HATU) (14.25 g, 0.038 mol, 1.5 eq.), Et$_3$N (5.06 g, 0.050 mol, 2.0 eq.) in CH$_2$Cl$_2$ was stirred at room temperature for 2 hours. To the reaction mixture, water (100 ml) was added and the organic phase was separated. The organic layer was washed with brine (2×50 mL) and dried with anhydrous sodium sulfate. The solution was concentrated in vacuo and the residue was purified with chromatography on silica gel to afford Compound 5 (5.6 g, yield 47%) as white solid.

$^1$H NMR (400 MHz, CDCl$_3$) δ 7.63-7.67 (m, 2H), 7.33 (m, 2H), 7.28 (m, 1H), 7.20 (m, 3H), 7.15 (m, 2H), 6.95-6.99 (m, 3H), 6.40 (m, 1H), 4.78 (d, J=4.4, 1H), 4.47 (d, J=5.2, 1H), 3.40 (m, 1H), 3.20 (s, 2H), 3.19 (m, 1H), 1.44 (m, 2H), 1.12 (m, 2H), 0.76 (s, 6H). MS (ESI) m/z 474.2 (M+H)$^+$.

Example 6: Synthesis of Compound 2

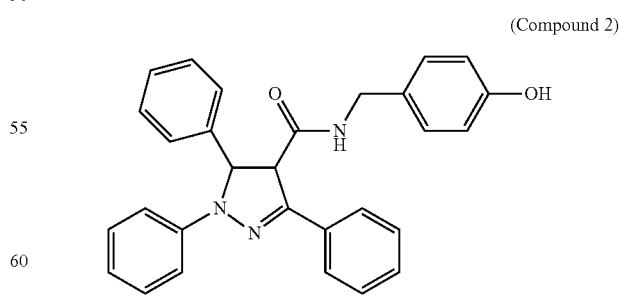

(Compound 2)

Using a similar synthetic procedure as in Examples 2-5, Compound 2 was synthesized.

1H NMR (400 MHz, DMSO-d$_6$) δ 9.31 (s, 1H), 8.92 (t, J=5.6, 1H), 7.72 (m, 2H), 7.37 (m, 5H), 7.30 (m, 3H), 7.16

(m, 2H), 7.00 (m, 4H), 6.74 (m, 1H), 6.73 (m, 2H), 5.47 (d, J=6.4, 1H), 4.31 (d, J=6.4, 1H), 4.20 (m, 2H). MS (ESI) m/z 448.2 (M+H)+

Example 7: Synthesis of Compound 6

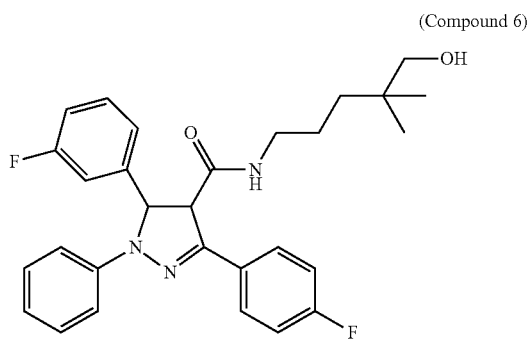 [SMILES: CC(C)(CO)CCCNC(=O)C1C(c2ccc(F)cc2)=NN(c2ccccc2)C1c1cccc(F)c1]

(Compound 6)

Using a similar synthetic procedure as in Examples 2-5, Compound 6 was synthesized.
$^1$H NMR (400 MHz, CDCl$_3$) δ 7.62-7.64 (m, 2H), 7.33 (m, 2H), 7.26 (m, 1H), 7.12-7.15 (m, 2H), 6.97-7.01 (m, 5H), 6.40 (m, 1H), 4.78 (d, J=5.2, 1H), 4.46 (d, J=5.2, 1H), 3.38 (m, 1H), 3.20 (s, 2H), 3.19 (m, 1H), 1.38 (m, 2H), 1.13 (m, 2H), 0.76 (d, J=3.2, 1H). MS (ESI) m/z 492.2 (M+H)+.

Example 8: Compounds of the Embodiments Suppress Tumor Growth In Vivo (Mouse Xenograft Model: Melanoma MelJuso)

In vivo efficacy study of Compounds 1, 2, 4, and 6 were performed using a Mouse Xenograft Model (Melanoma MelJuso). Mice were injected s.c. with 3×10$^6$ cells in the dorsal area in a volume of 100 μl. 13 days after inoculation, the mice started receiving treatments with the administered compound at a dose of 50 mg/kg body weight daily for 14 days (n=10). Vehicle alone was used as control (n=10). The administered compounds and vehicle were adjusted in a volume of 40 μl for i.p. injection in the abdomens of the mice. Tumor size and tumor volumes were calculated as described above. As can be seen in FIG. 1, tumor growth was dramatically suppressed after treatment with the administered compounds.

Example 9: Compounds of the Embodiments Suppress Tumor Growth In Vivo (Mouse Xenograft Model: Mesothelioma MS-1)

Figure 2:
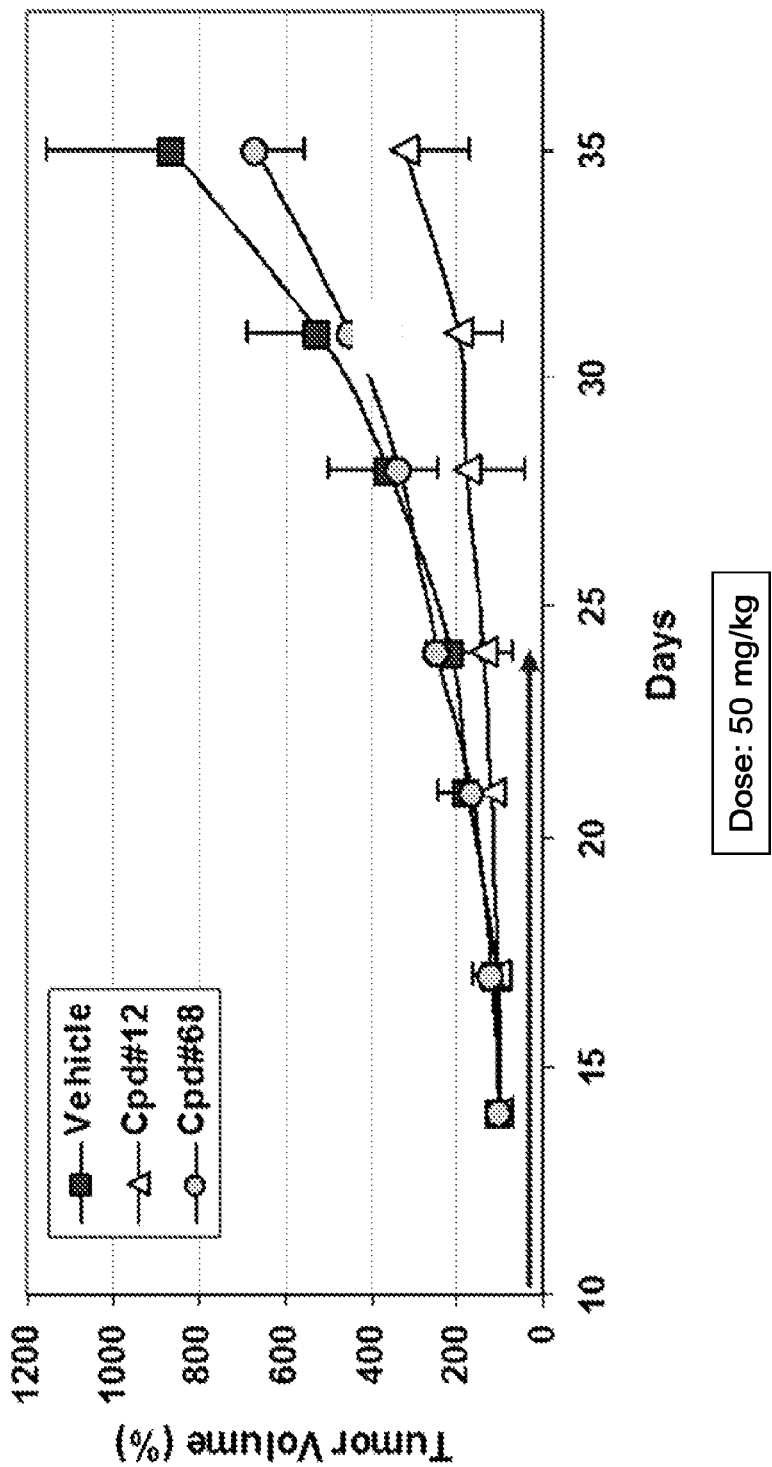
FIG. 2 shows an in vivo efficacy study of Compounds 1 and 4 using a Mouse Xenograft Model (mesothelioma MS-1), according to embodiments of the present disclosure. Tumor weight significantly decreased after treatment with the administered compounds. Results are the means±SD (error bars). Arrow indicates the period of injection.

In vivo efficacy study of Compounds 1 and 4 were performed using a Mouse Xenograft Model (Mesothelioma MS-1). Five female athymic nude mice per group were injected s.c. with 3×10$^6$ cells in the dorsal area in a volume of 100 μl. Ten days after inoculation, we commenced i.p. injection of the compounds at 50 mg/kg body weight daily for 14 days (n=5). Vehicle alone was used as control (n=5). Tumors were allowed to grow an additional two weeks after completion of the treatments. Tumor sizes was measured twice weekly until the completion of the experiments. Tumor weight decreased after treatment with the administered compounds compared to the control group (FIG. 2).

Example 10: Compounds of the Embodiments Suppress Tumor Growth In Vivo (Mouse Xenograft Model: Lung cancer A549)

Figure 3:
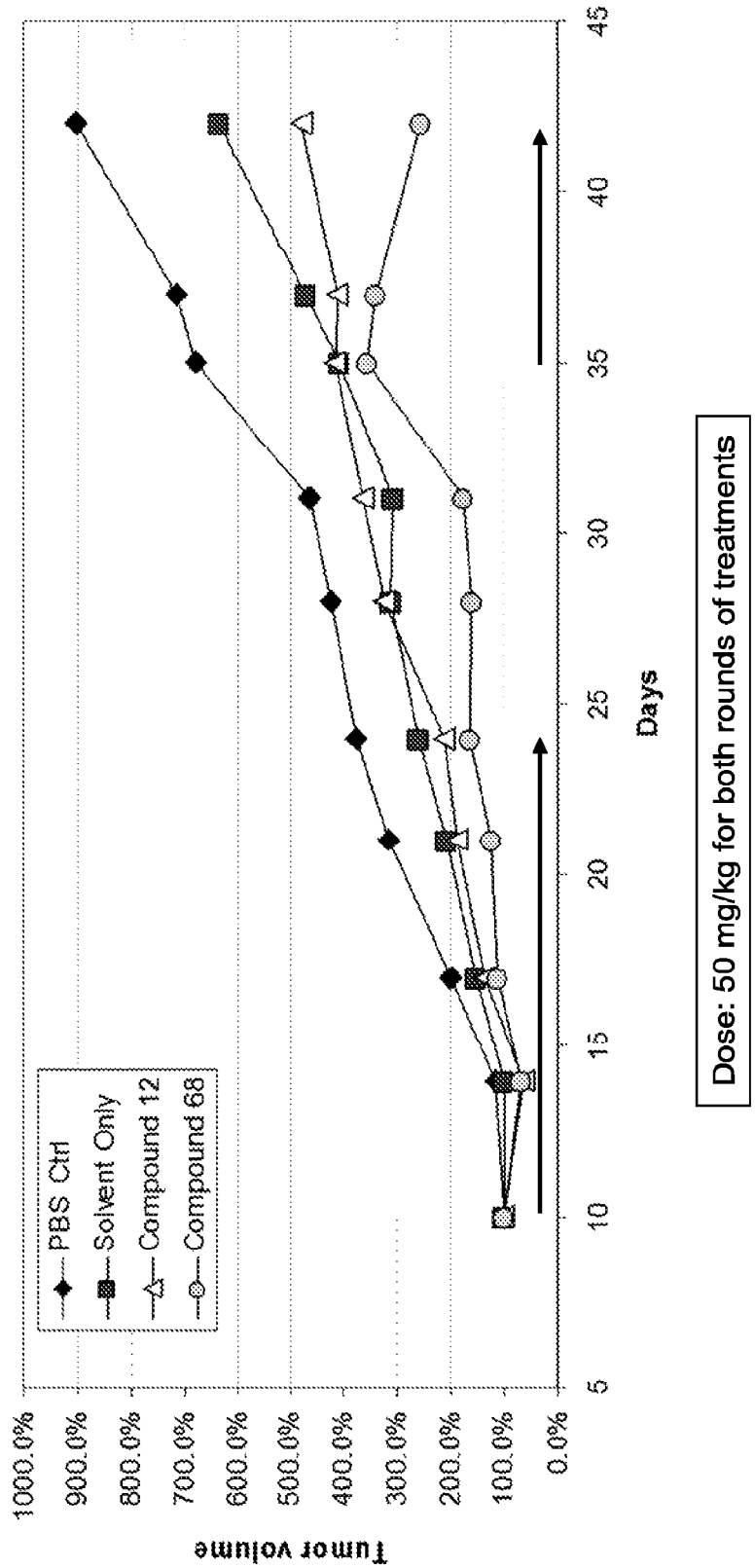
FIG. 3 shows an in vivo efficacy study of Compounds 1 and 4 using a Mouse Xenograft Model (lung cancer A549), according to embodiments of the present disclosure. Tumor weight significantly decreased after treatment with the administered compounds. Results are the means±SD (error bars). Arrow indicates the period of injection.

In vivo efficacy study of Compounds 1 and 4 in Mouse Xenograft Model (NSCLC A549) was examined. Mice were injected s.c. with 3×10$^6$ cells in the dorsal area in a volume of 100 μl. 10 days after inoculation, the mice started receiving treatments with Compounds 1 or 4 at a dose of 50 mg/kg body weight daily for 14 days (n=5), then another round of treatment at 50 mg/kg body weight daily for 1×7 days. Vehicle alone was used as control (n=5). The administered compounds and DMSO were adjusted in a volume of 50 μl for i.p. injection in the abdomens of the mice. 43 days after the initial tumor inoculation, tumors were dissected from the mice of each group and their weights were measured using a scale. Tumor weight decreased after treatment with the administered compounds compared to the control group (FIG. 3). This low dose in vivo result is consistent with in vitro data presented herein.

Figure 4:
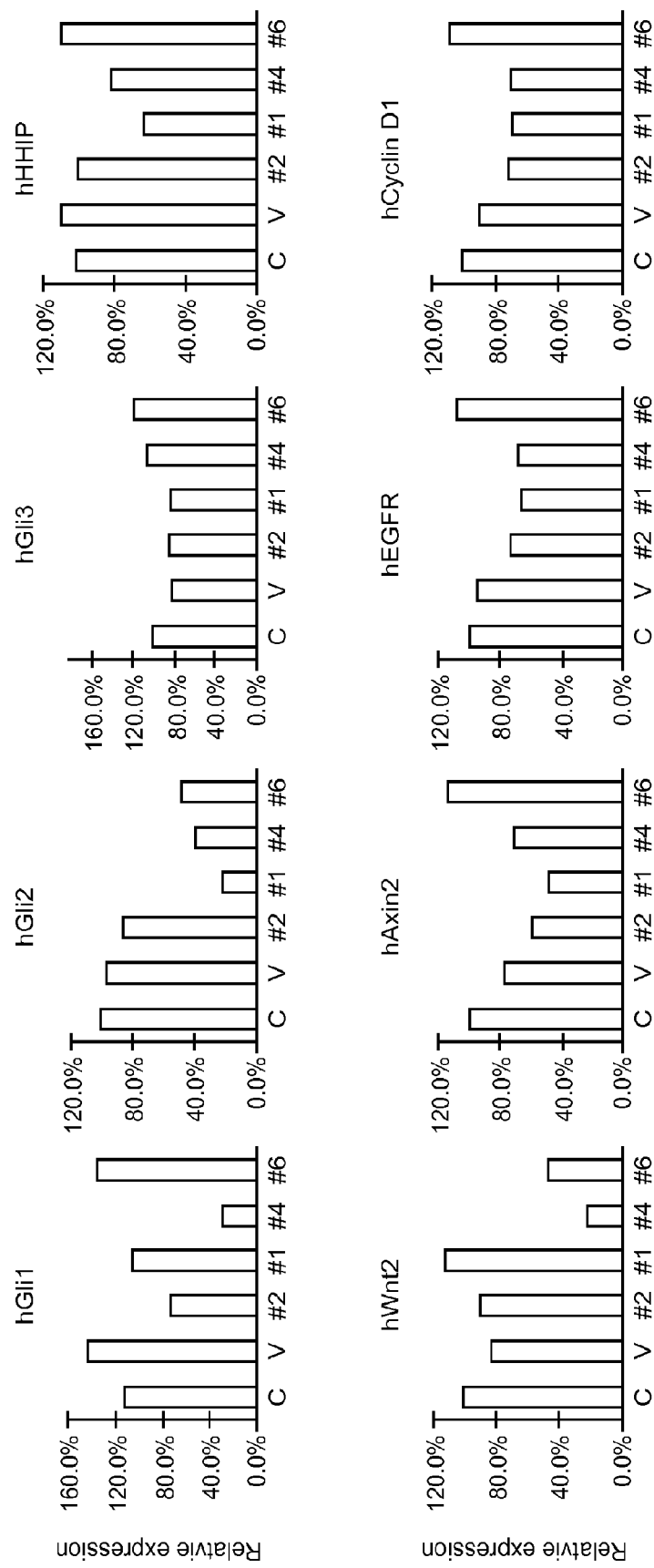
FIG. 4 shows regulation in the hGli1, hGli2, hGli3, hHHIP, hWnt2, hAxin2, hEGFR, and hCyclin D1 activity by Compounds 1, 2, 4, and 6, according to embodiments of the present disclosure.

Example 11: Effect of Compounds of the Embodiments on the Hedgehog Pathway in Tumors In Vivo To examine whether Compounds 1, 2, 4, and 6 suppressed tumor growth through inhibition of the Hedgehog signaling pathway in vivo, expression of the key components and direct target genes of the Hh pathway (e.g. Gli1, Gli2, Gli3, HHIP and Cyclin D1) were analyzed by quantitative real-time RT-PCR using total RNA isolated from the xenograft tumors. GAPDH served as a control. This RT-PCR analysis was performed using a "pooled" tumor from two randomly selected mice of each group with reasonable size tumors. It was found that Hh signaling was inhibited by Compounds 1, 2, 4, and 6 in Melanoma tumor (MelJuso) (FIG. 4). The results are shown in FIG. 4, where C is control and V is vehicle.

Example 12: Effect of Compounds of the Embodiments on the Canonical Wnt Pathway in Tumors In Vivo To examine whether Compounds 1, 2, 4, and 6 suppressed tumor growth through inhibition of the Wnt signaling pathway in vivo, expression of the key components and direct target genes of the Wnt pathway (e.g. Wnt2, Axin2, EGFR, and Cyclin D1) were analyzed by quantitative real-time RT-PCR using total RNA isolated from the xenograft tumors. GAPDH served as a control. This RT-PCR analysis was performed using a "pooled" tumor from two randomly selected mice of each group with reasonable size tumors. It was found that expression of the key indicator of the canonical Wnt activation was significantly down-regulated in Compounds 1, 2, and 4 treated Melanoma tumor compared to controls (FIG. 4). The results are shown in FIG. 4, where C is control and V is vehicle.

Figure 5:
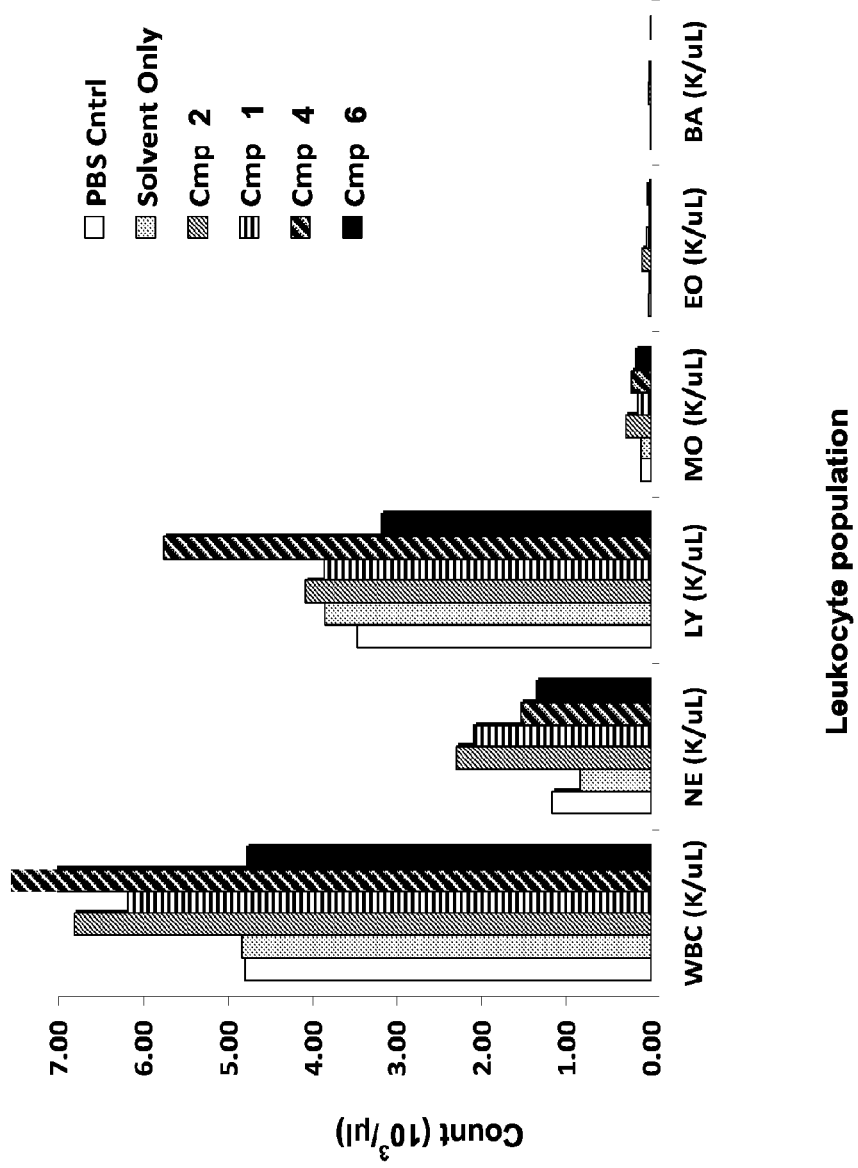
FIG. 5 shows effect of Compounds 1, 2, 4, and 6 on leukocyte population of mice after in vivo treatment, according to embodiments of the present disclosure. At the completion of the in vivo studies, leukocytes (WBC: white blood cell, NE: neutrophil, LY: lymphocyte, MO: monocyte, EO: eosinophil, BA: basophil) from each animal from all treatment groups were collected and leukocyte population was counted through a blood cell counter. Results are the means±SD (error bars).
Figure 6:
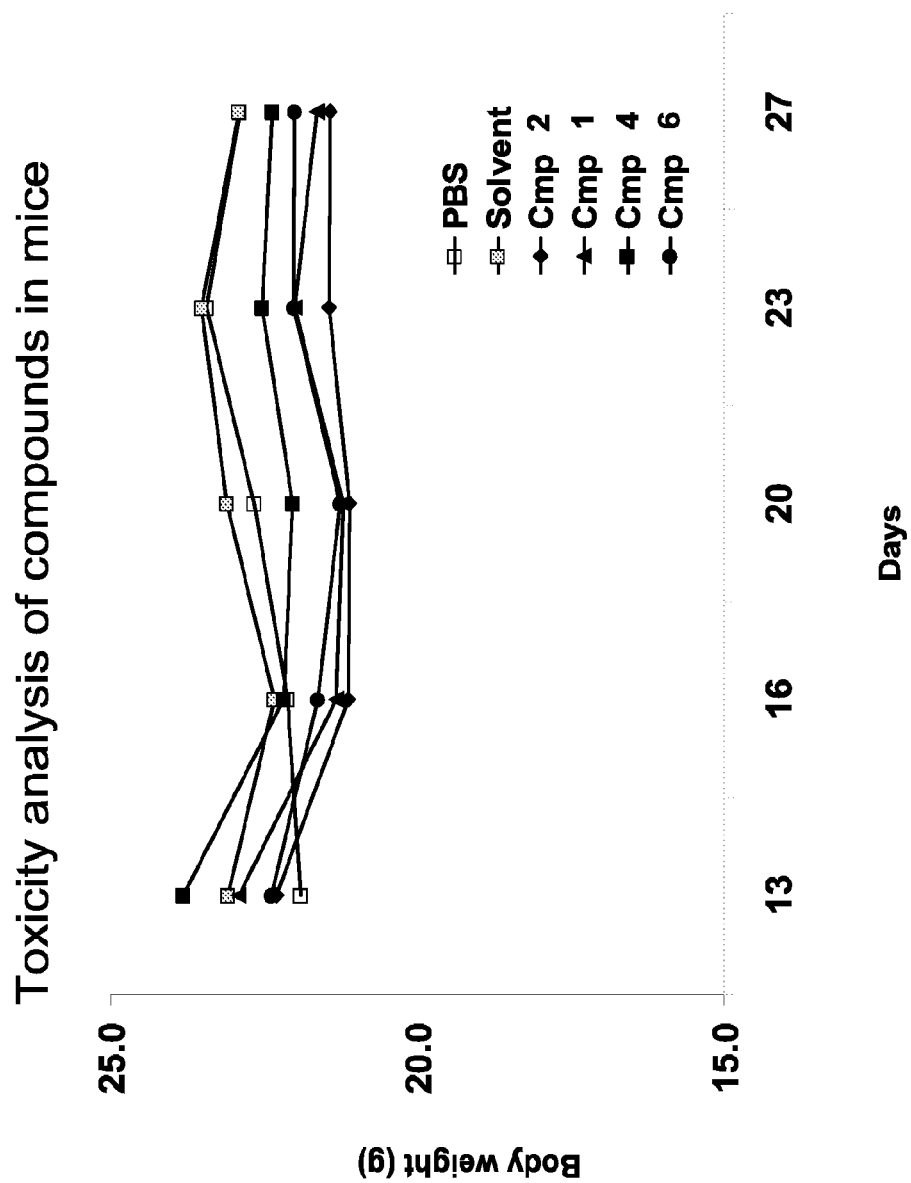
FIG. 6 shows effect of Compounds 1, 2, 4, and 6 on the body weight of mice during the period of drug administration of the in vivo studies, according to embodiments of the present disclosure.
Figure 7:
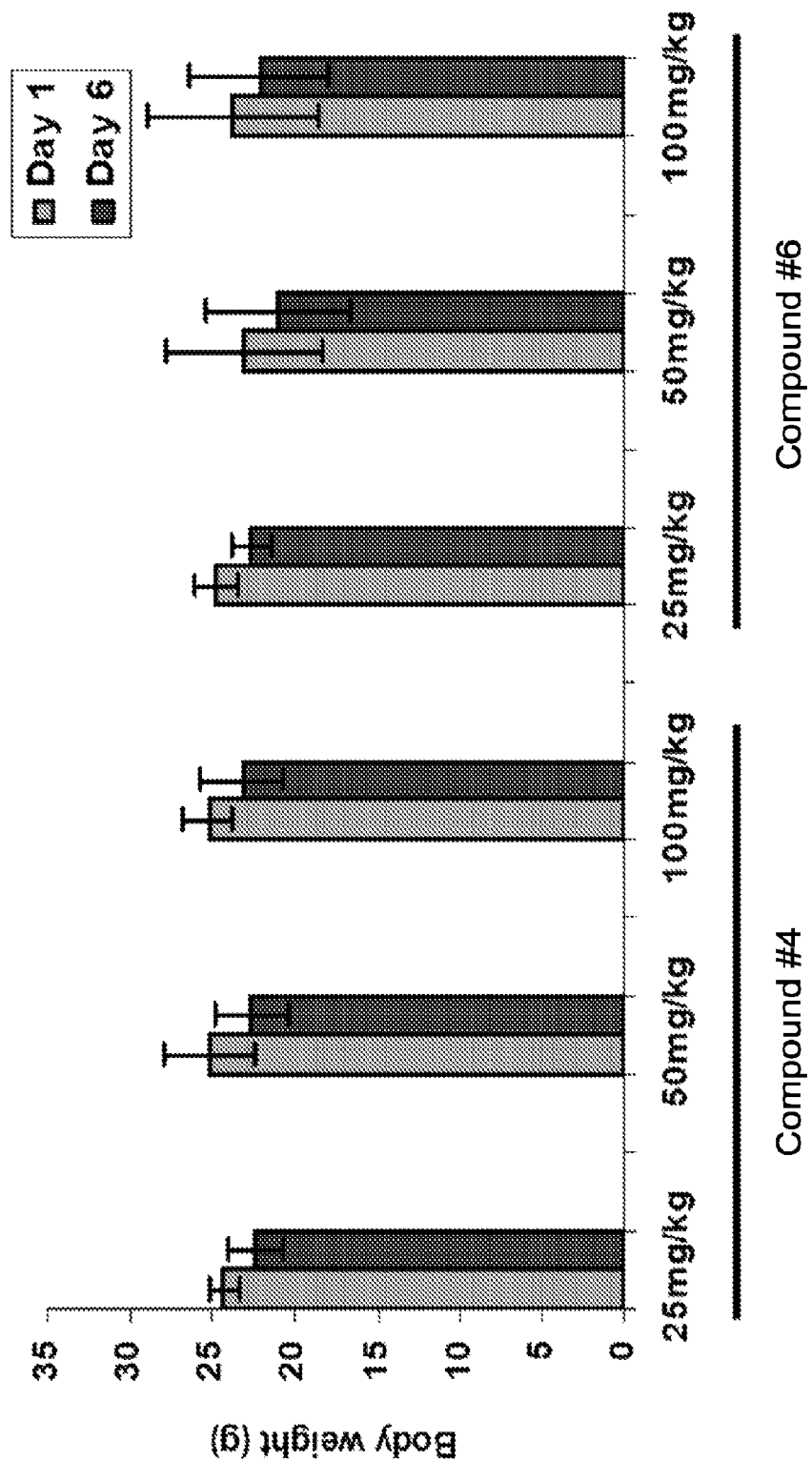
FIG. 7 shows effect of different doses of compounds 4 and 6 on the body weight of mice in a toxicity study, according to embodiments of the present disclosure The compounds were i.p. injected in the abdomens at 3 different doses: 25, 50, and 100 mg/kg body weight to the animals for 6 consecutive days. Each dosing group contained 3 mice. The body weight of mice was measured using a scale. Results are the means±SD (error bars).
Figure 8:
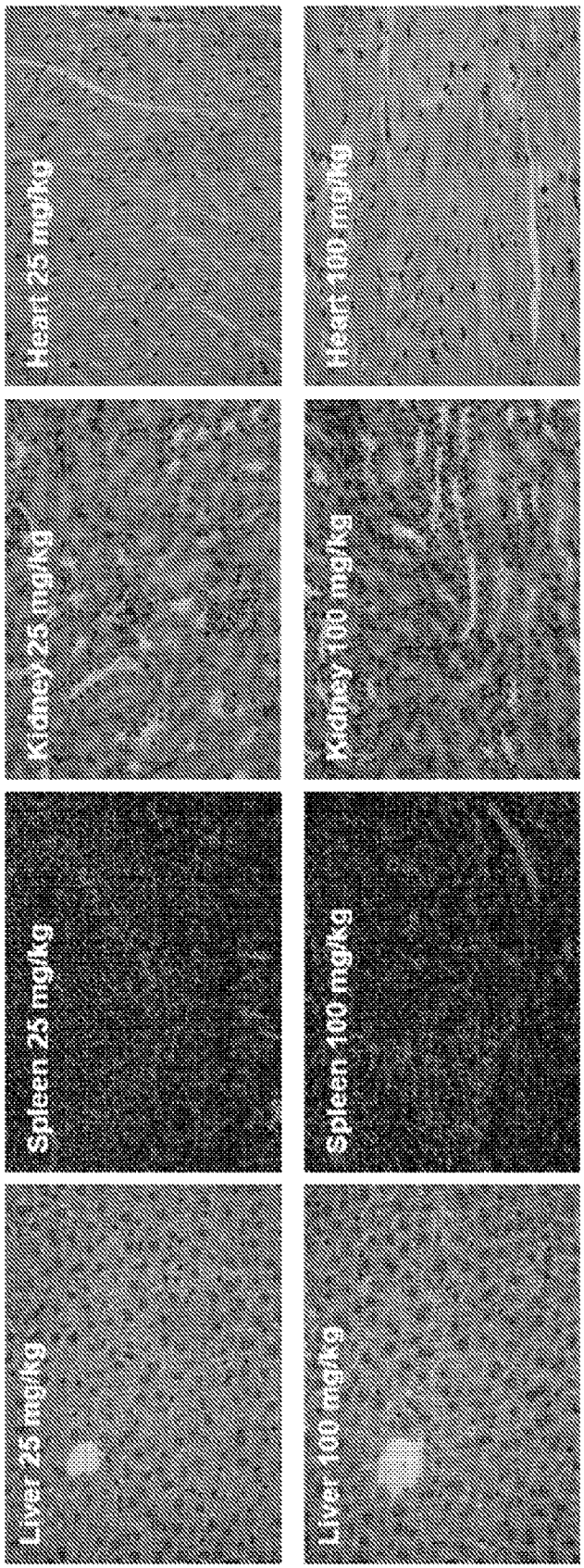
FIG. 8 shows the screening of Compound 2 using a cytotoxicity assay and liver cells, spleen cells, kidney cells, and heart cells from mice, according to embodiments of the present disclosure.
Figure 9:
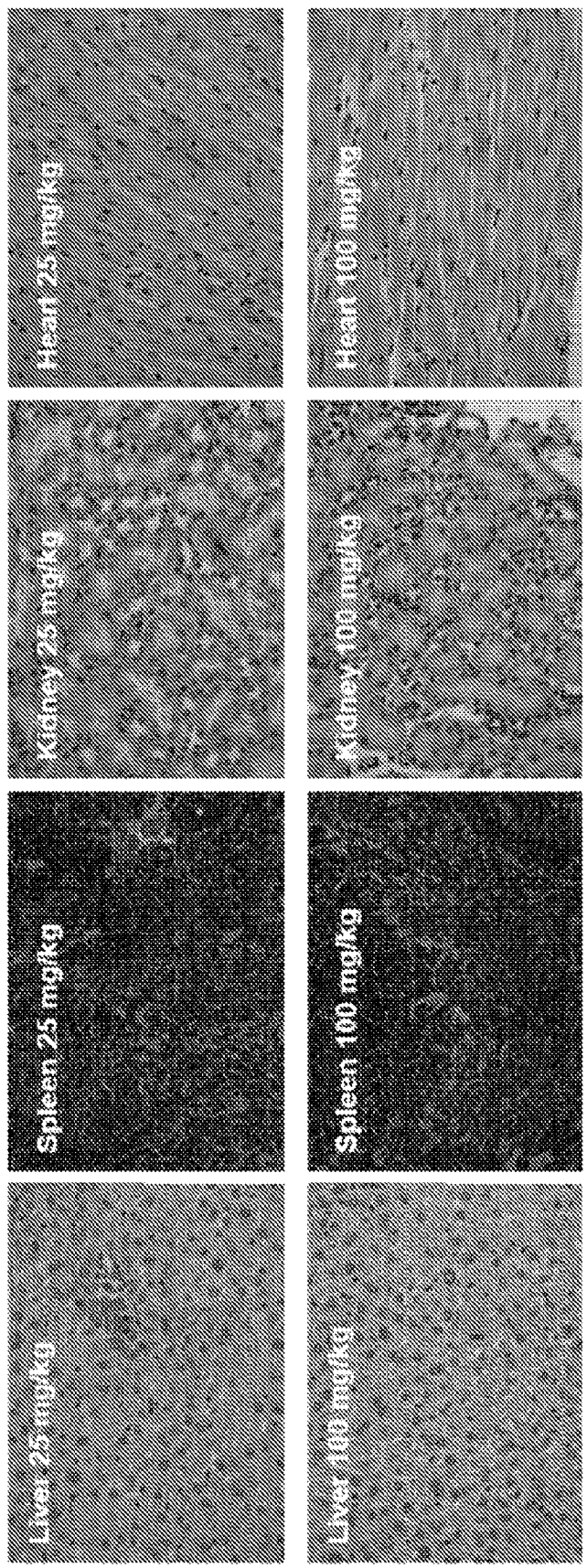
FIG. 9 shows the screening of Compound 1 using a cytotoxicity assay and liver cells, spleen cells, kidney cells, and heart cells from mice, according to embodiments of the present disclosure.
Figure 10:
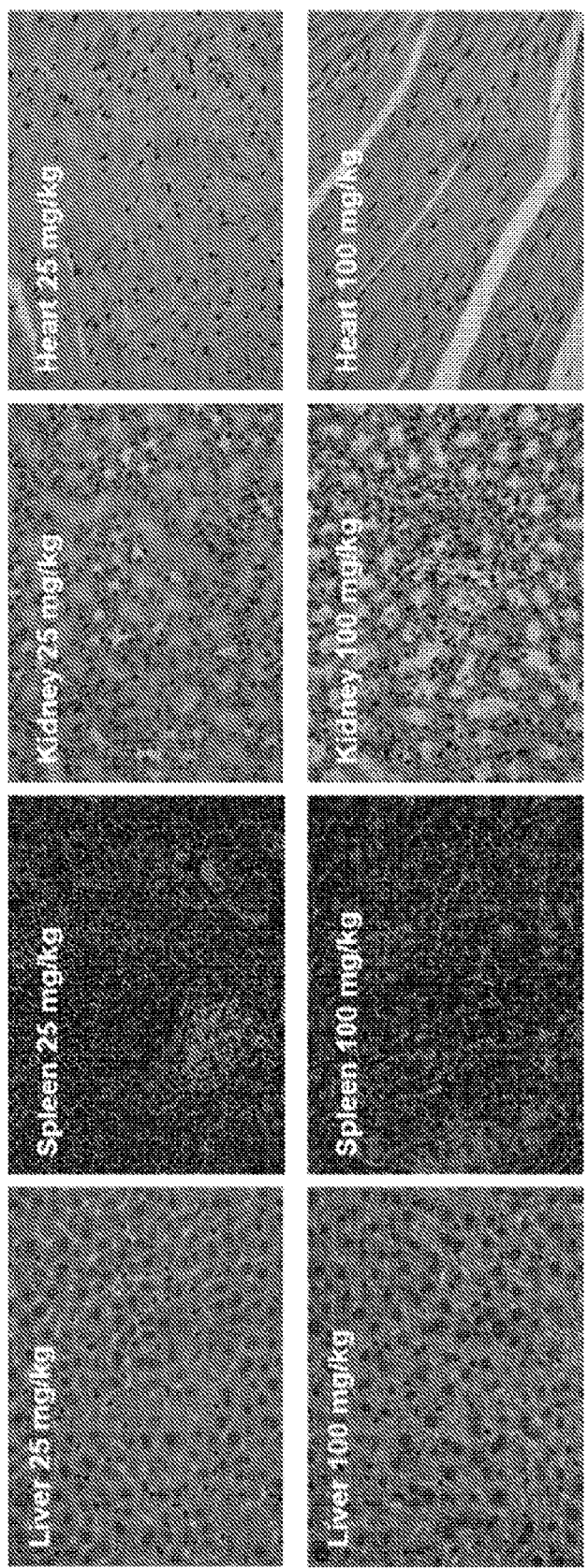
FIG. 10 shows the screening of Compound 4 using a cytotoxicity assay and liver cells, spleen cells, kidney cells, and heart cells from mice, according to embodiments of the present disclosure.
Figure 11:
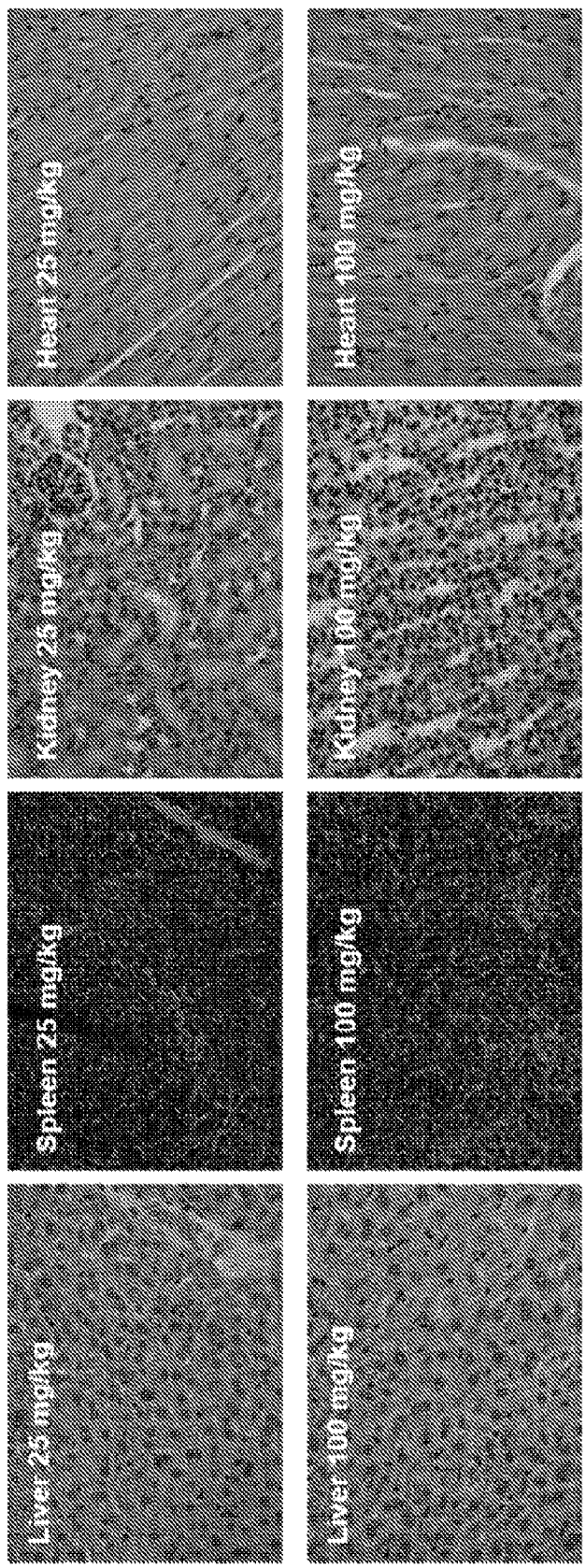
FIG. 11 shows the screening of Compound 6 using a cytotoxicity assay and liver cells, spleen cells, kidney cells, and heart cells from mice, according to embodiments of the present disclosure.
Figure 12:
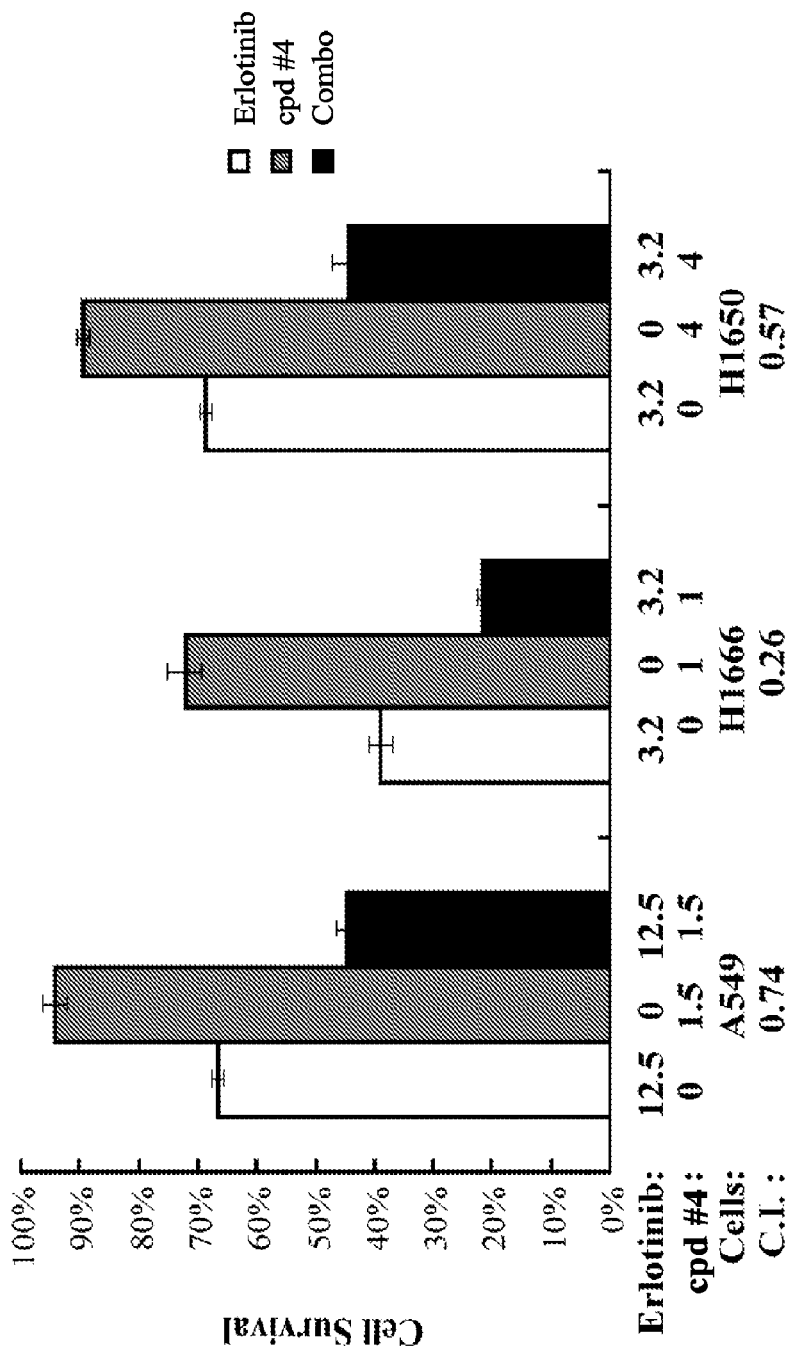
FIG. 12 shows synergy of erlotinib (Tarceva) and Compound 4 in lung cancer cells, according to embodiments of the present disclosure.
Figure 13:
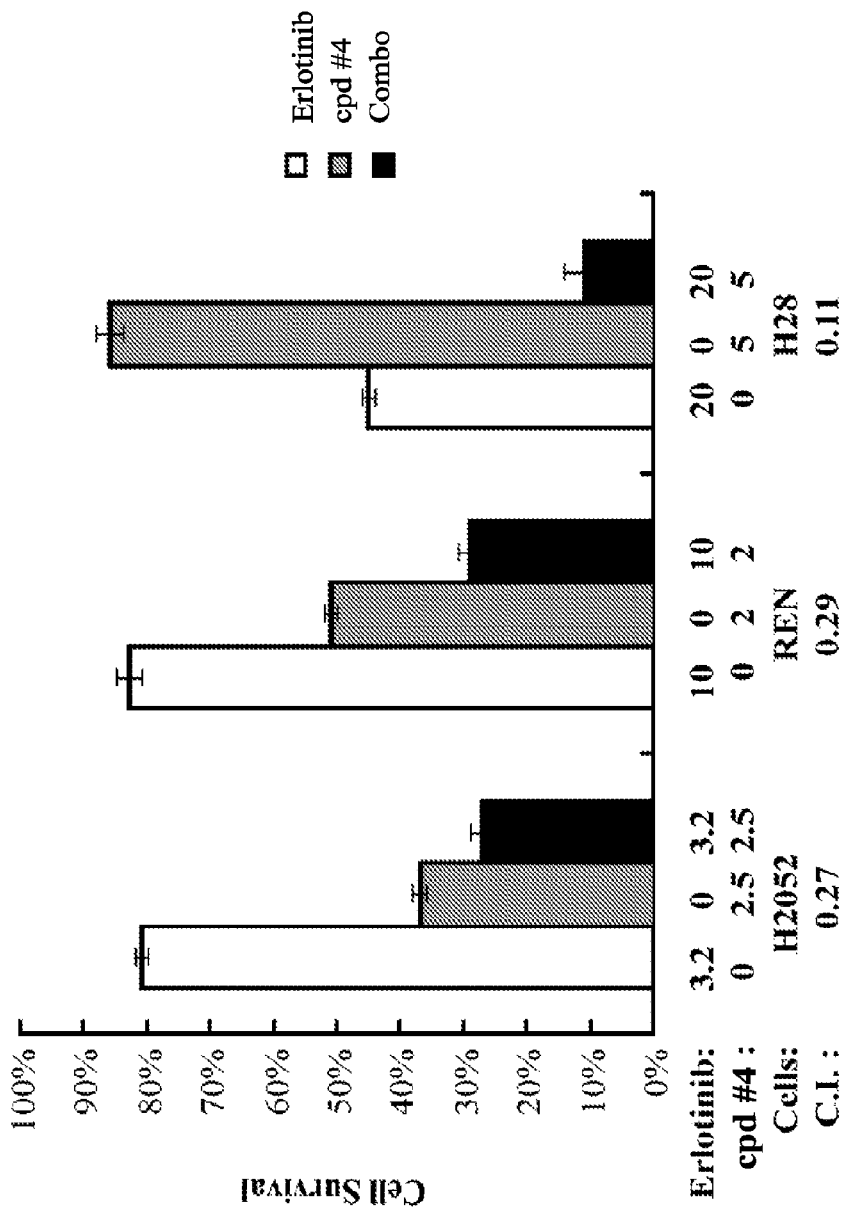
FIG. 13 shows synergy of erlotinib (Tarceva) and Compound 4 in mesothelioma cells, according to embodiments of the present disclosure.
Figure 14:
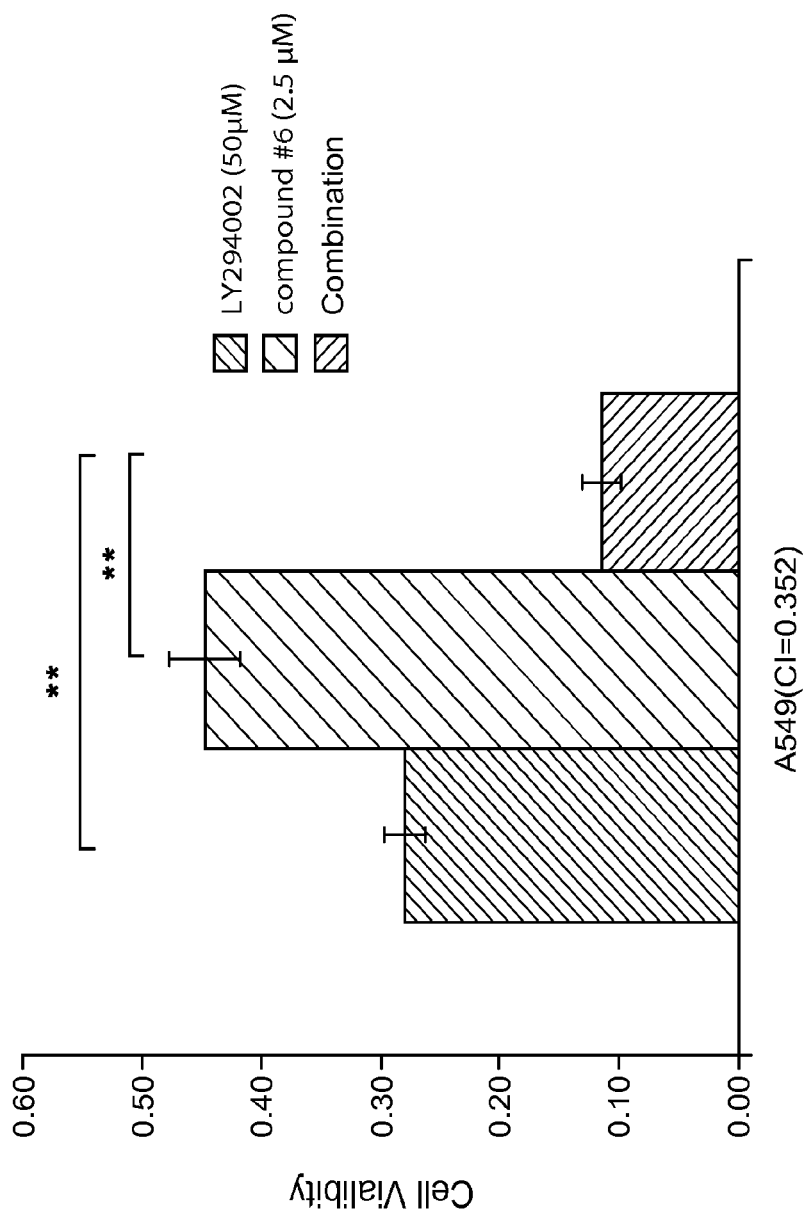
FIG. 14 shows synergy of PI3K inhibitor LY294002 and Compound 6 in lung cancer cells, according to embodiments of the present disclosure.
Figure 15:
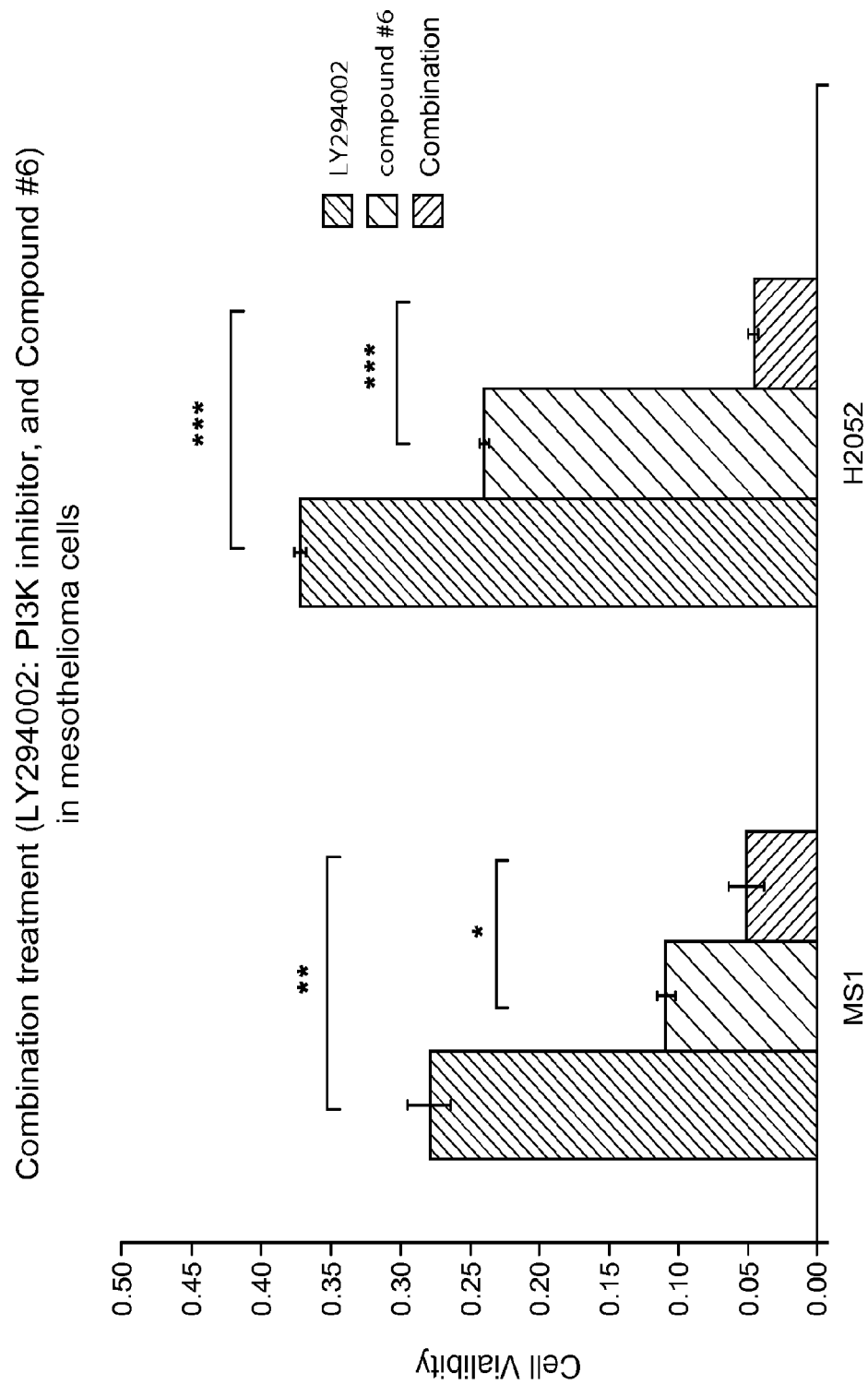
FIG. 15 shows synergy of PI3K inhibitor LY294002 and Compound 6 in mesothelioma cells, according to embodiments of the present disclosure.
Figure 16:
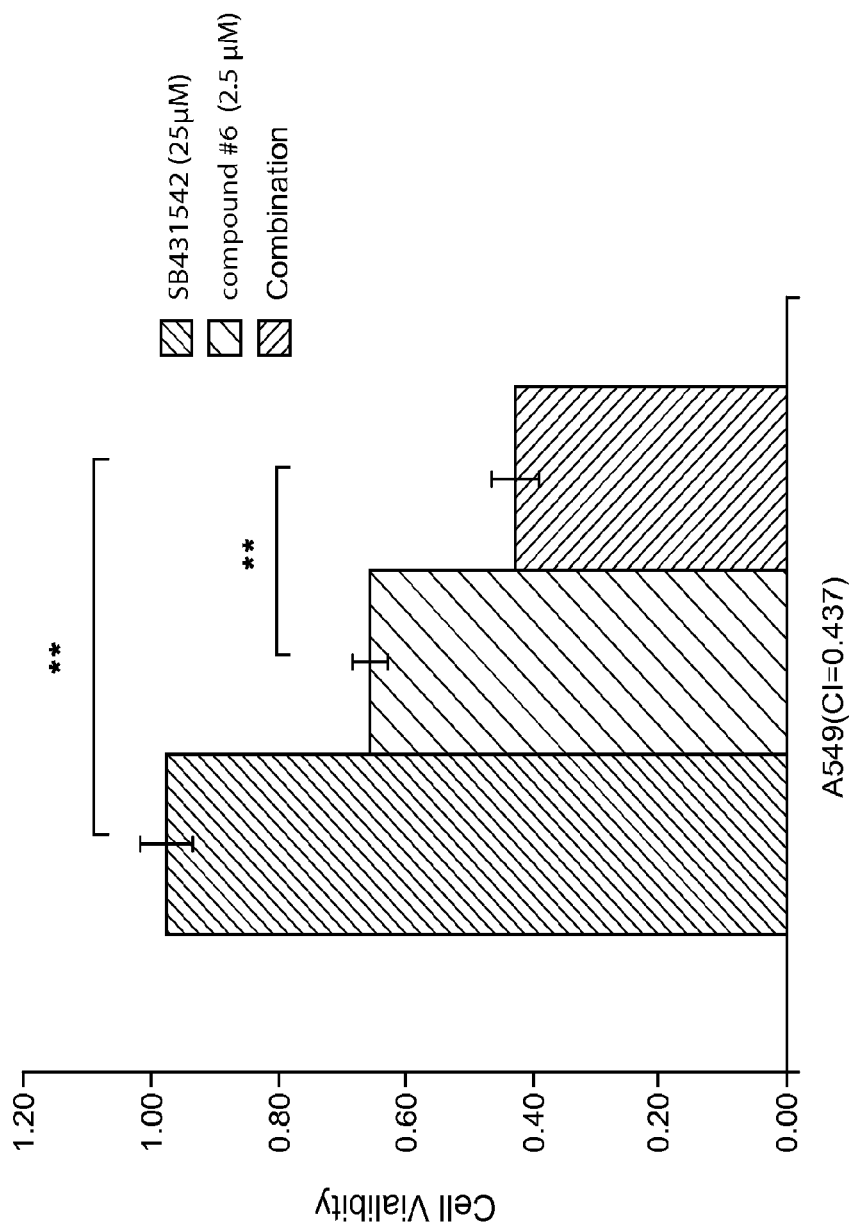
FIG. 16 shows synergy of TGFβ inhibitor SB431542 and Compound 6 in lung cancer cells, according to embodiments of the present disclosure.
Figure 17:
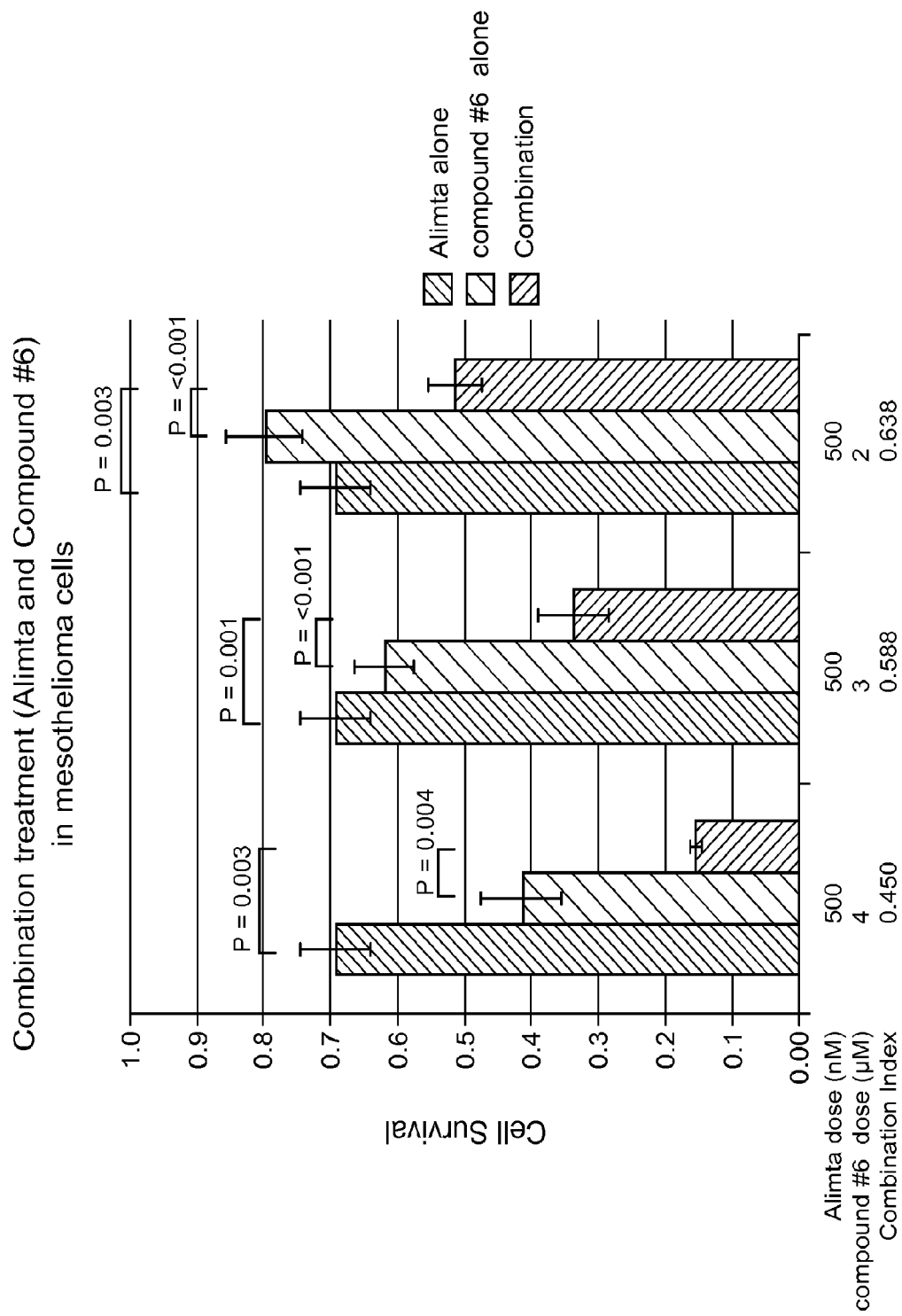
FIG. 17 shows synergy of pemetrexed (Alimta) and Compound 6 in mesothelioma cells, according to embodiments of the present disclosure.

Example 13: Toxicity Analysis of Compounds of the Embodiments in Mice after In Vivo Treatment As preliminary in vivo toxicity study of Compounds 1, 2, 4, and 6, it was examined if there were changes of leukocyte population and loss of body weight in the mice after the treatment. At the completion of the in vivo studies as described herein, leukocytes (WBC: white blood cell, NE: neutrophil, LY: lymphocyte, MO: monocyte, EO: eosinophil, BA: basophil) from each animal from all treatment groups were collected and leukocyte population was counted through a blood cell counter. Body weights of control groups (n=10) and the treated group (n=10) were measured using a scale during the course of drug administration. No noticeable changes of leukocyte population or loss of the body weight was observed after the treatment with the administered compounds (FIGS. 5 and 6). In an additional toxicity study, effect of different doses of compounds 4 and 6 on the body weight of mice was examined. The compounds were i.p. injected in the abdomens at 3 different doses: 25, 50, and 100 mg/kg body weight to mice (3 mice per dosing group) for 6 consecutive days. Consistently, no noticeable loss of the body weight was observed after the treatments with the administered compounds (FIG. 7).

Example 14: Effects of Compounds of the Embodiments on Various Cells in Mice To analyze toxicity of the Compounds 1, 2, 4, and 6 in vivo, each group (three mice) was i.p. injected with two doses of each Compound daily for 6 days, and then major mouse organs, such as liver, spleen, kidney, and heart were resected from the mice. The specimens will be fixed in 4% buffered formaldehyde, embedded in paraffin, sectioned and histologically analyzed by hematoxylin and eosin (H&E) staining No noticeable toxicity in organs from the Compound treated mice was observed. Results are shown in FIGS. 8-11.

Example 15: Synergistic Effect of Compounds of the Embodiments and Chemotherapies in the Treatment of Cancer Cells Combination treatments of the Compounds with several chemotherapies: erlotinib (Tarceva®), PI3K inhibitor LY294002, TGFβ inhibitor SB431542, and pemetrexed (Alimta®) were performed in human NSCLC and MM cell lines (FIGS. 12-17). In all experiments, NSCLC and MM cell lines were treated with different doses of each compound or combination for 72 hours, and MTS assays were performed to determine the cell proliferations. Combination Index (CI), calculated by CalcuSyn software (Biosoft, Cambridge, UK), was applied to describe the effect of the combination effects of two compounds, where CI<1 indicates Synergism, CI=1 indicates Additive effects, and CI>1 indicates Antagonism. Student's t-tests were applied for statistical analysis. It was found that the combination treatments could synergistically suppress the proliferation of NSCLC and MM cells.

Example 16: Chiral HPLC Column Separation of Enantiomers P1 and P2 of Compound 4

Experiments were performed to separate two enantiomers (P1 and P2) of compound 4. A Chiralpak AD-H column (Chiral Technologies, Exton, Pa.) was used. Column size was 25 cm×4.6 mm i.d., with a CSP particle size of 5 microns. HPLC-grade methanol was used as a co-solvent entrained in carbon dioxide at 15% (v/v). Column temperature was 39.7° C. The $CO_2$ flow rate was 2.55 ml/min and the co-solvent flow rate was 0.45 ml/min, yielding a total flow rate of 3 ml/min. Front and back pressures were 186 and 150 bar, respectively, yielding a pressure drop of 36 bar. Photodiode array start and stop wavelengths were 214 and 359 nm, respectively.

Under the conditions described, enantiomer P1 of compound 4 was found to have a retention time of 3.27 min, while enantiomer P2 of compound 4 had a retention time of 4.14 min. The percentage area under the curve for each enantiomer was 49.1% (enantiomer P1) and 47.7% (enantiomer P2), respectively. Subsequent repeat chromatography of enantiomer P1 and enantiomer P2 separately (with HPLC conditions identical as described above, except for a temperature of 39.1° C. and pressure drop of 45 bar for enantiomer P1 and a temperature of 41.1° C. and pressure drop of 33 bar for enantiomer P2) indicated purities of 99.9% (enantiomer P1) and 98.8% (enantiomer P2), respectively, with a retention time of 3.53 min for enantiomer P1 and 4.47 min for enantiomer P2.

Example 17: Chiral Compound 4 Demonstrates Enantiomer-Specific Activity in Multiple Cancer Cell Lines Experiments were performed to determine enantiomer-specific activity in various cancer cell lines (including lung cancer, melanoma, mesothelioma, colorectal cancer, pancreatic cancer and prostate cancer). Cancer cell lines were treated with either vehicle or a dosage range from 0.1 µM to 20 µM of compound 4, and the two purified enantiomers (P1 and P2) of compound 4 for 4 days in medium containing 0.5% FBS and determined cell toxicity $IC_{50}$ values. Data showed that enantiomer P2 was more active in suppressing cancer cell growth than enantiomer P1. The results also showed that activities of compound 4 and enantiomer P2 were specific because the $IC_{50}$ values of the P2 enantiomer were approximately 50% of those of compound 4 (i.e., an equal mixture of the P1 and P2 enantiomers). FIG. 18 shows cell toxicity $IC_{50}$ values (µM) for Gli inhibitor Compound 4 and each of its two purified enantiomers (P1 and P2) for various cancer cell lines.

Figure 19:
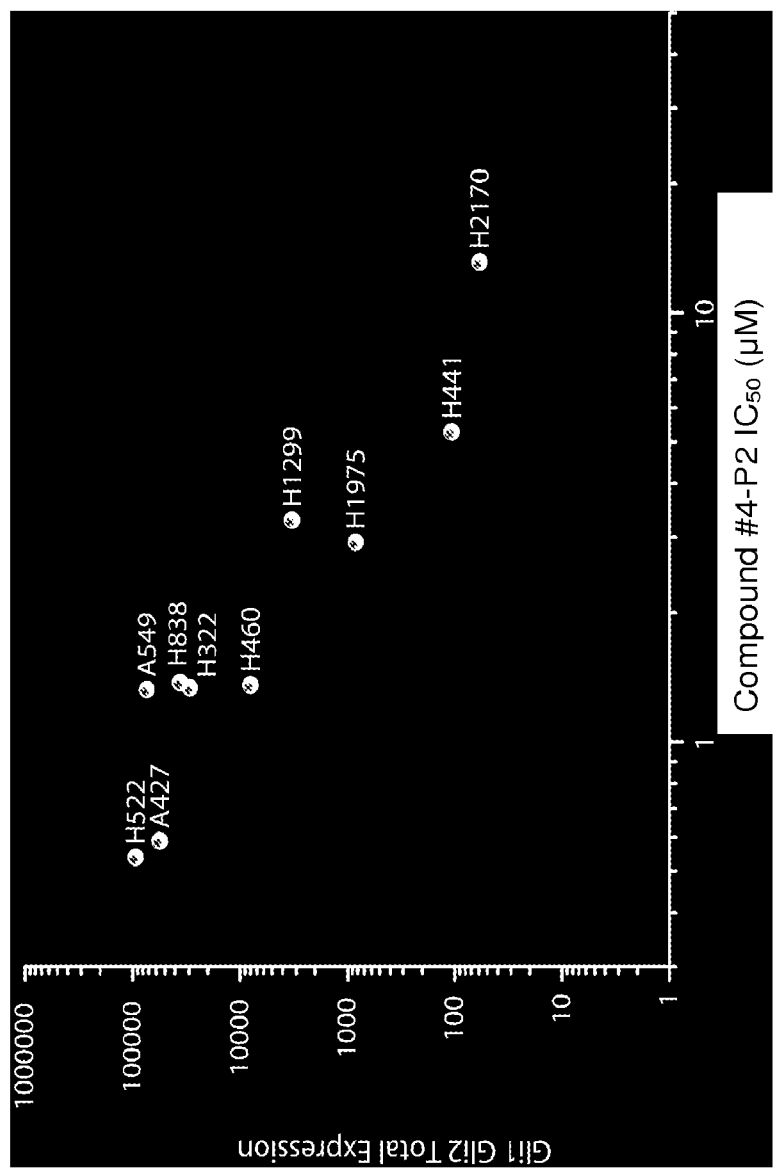
FIG. 19 shows a graph of the correlation of efficacy of Gli inhibitor Compound 4 and Gli expression in non-small cell lung cancer (NSCLC) cells, according to embodiments of the present disclosure.

Example 18: Correlation of Efficacy of Gli Inhibitor Compound 4-Enantiomer P2 and Gli Expression in Lung Cancer Cell Lines Experiments were performed to examine the correlation between efficacy of Compound 4-enantiomer P2 ($IC_{50}$ values as described in FIG. 18) and expression levels of Gli1 and Gli2 in lung cancer cell lines. $IC_{50}$ values (µM) of Compound 4-enentiomer P2 were negatively correlated with the mRNA expression levels of Gli1 and Gli2 (measured by real-time RT-PCR) in those cell lines, supporting that Compound 4-enentiomer P2 was specific in inhibition of the Gli function in human lung cancer cell lines. FIG. 19 shows a graph of the correlation of efficacy of Gli inhibitor Compound 4 and Gli expression in non-small cell lung cancer (NSCLC) cells.

Figure 20:
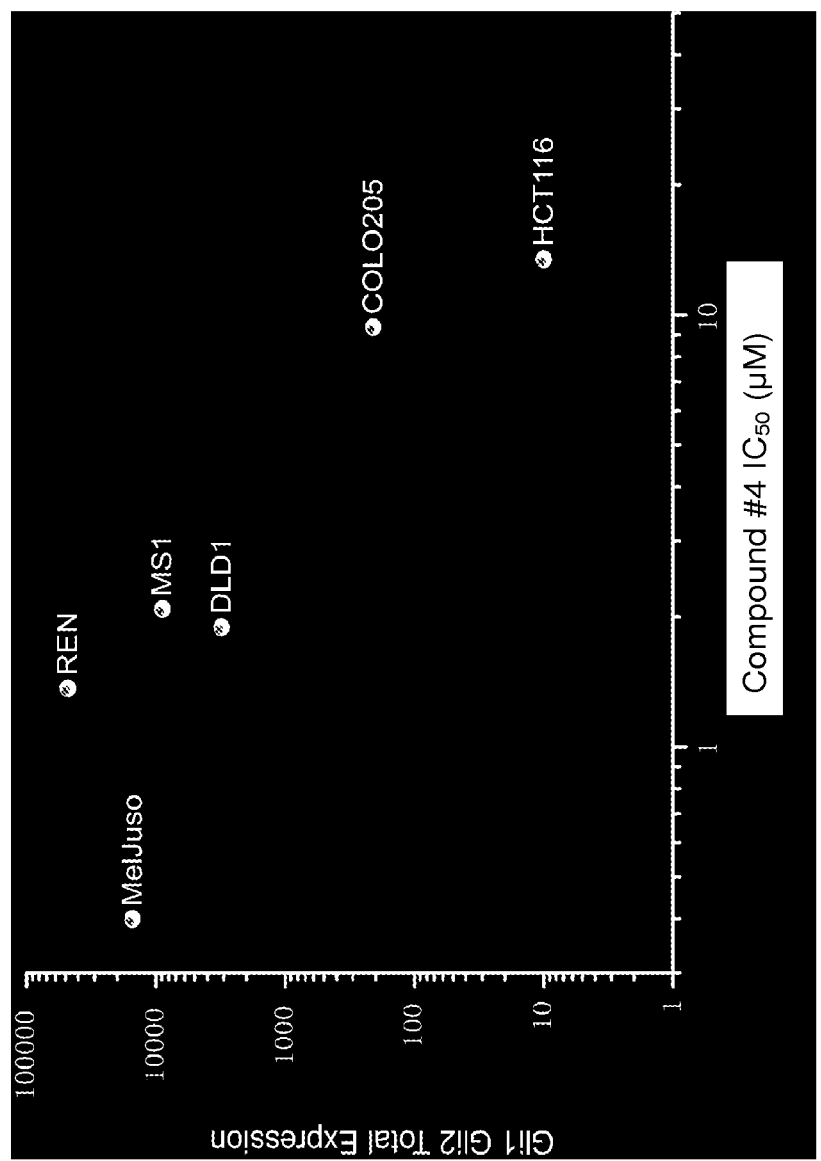
FIG. 20 shows a graph of the correlation of efficacy of Gli inhibitor Compound 4-enantiomer P2 and Gli expression in cancer cells, according to embodiments of the present disclosure.

Example 19: Correlation of Efficacy of Gli Inhibitor Compound 4-Enantiomer P2 and Gli Expression in Other Cancer Cells Experiments were performed to examine the correlation between efficacy of Compound 4-enentiomer P2 ($IC_{50}$ values as described in FIG. 18) and expression levels of Gli1 and Gli2 in several other types of cancer cell lines including mesothelioma, melanoma and colorectal cancer. $IC_{50}$ values (µM) of Compound 4-enentiomer P2 were negatively correlated with the mRNA expression levels of Gli1 and Gli2 (measured by real-time RT-PCR) in those cell lines, supporting that Compound 4-enentiomer P2 was specific in inhibition of the Gli function in cancer cell lines. FIG. 20 shows a graph of the correlation of efficacy of Gli inhibitor Compound 4-enantiomer P2 and Gli expression in these other types of cancer cell lines including mesothelioma, melanoma and colorectal cancer cancer cells.

Example 20: Inhibition of the Gli/TAF9-Dependent Transcription Activity by Small Gli Inhibitor Compound 4-Enantiomer P2 in NSCLC Cell Line A549

Figure 21:
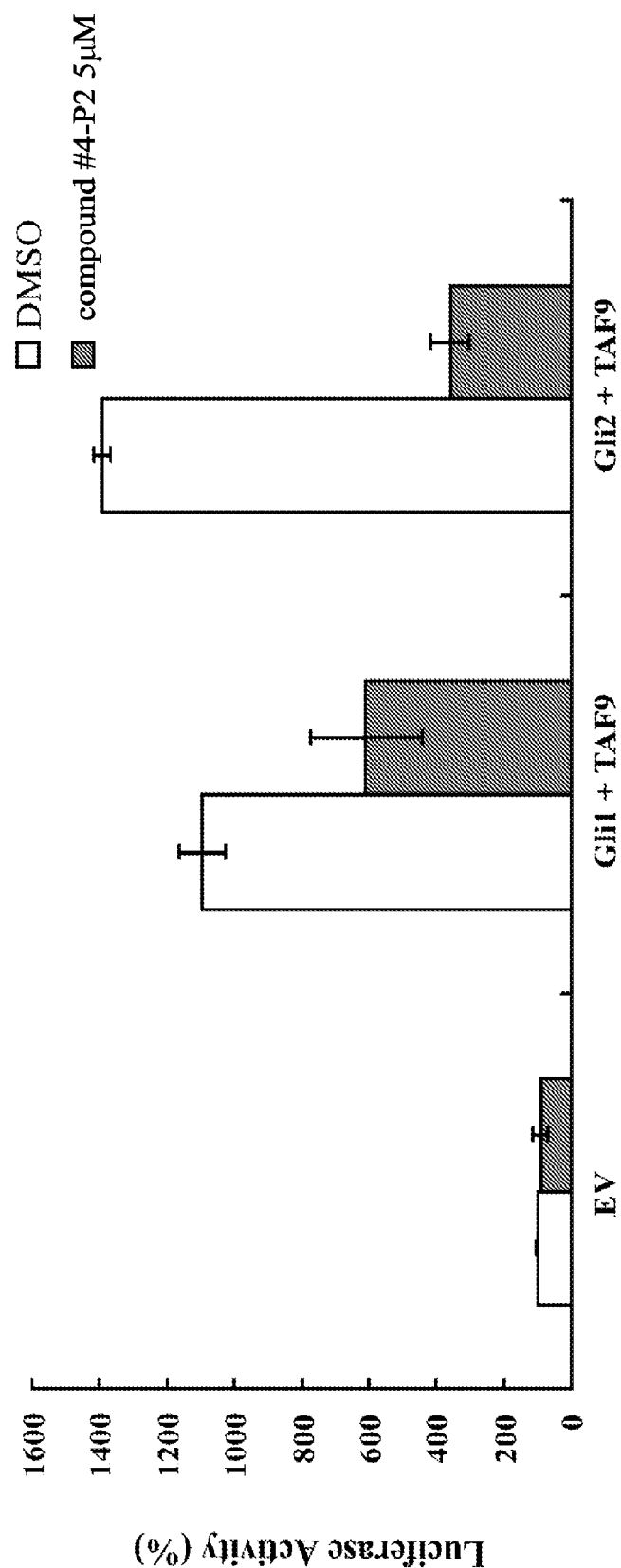
FIG. 21 shows graphs of luciferase activity (%) showing that Gli inhibitor Compound 4-enantiomer P2 inhibits Gli/TAF dependent transcription activity in NCSLC cell line A549 in vitro, according to embodiments of the present disclosure.

To examine the specificity of Compound 4-enantiomer P2 in inhibiting Gli function and to validate whether it blocks the interaction between Gli and TAF9, experiments were performed using the 8 repeats of Gli-binding sites (8×Gli BS) linked to a luciferase reporter gene as a surrogate measurement of the Gli-dependent transcription to examine the luciferase activity after Compound 4-enantiomer P2 treatments in NSCLC A549 cells. The results indicated that over-expression of Gli1 or Gli2 alone significantly increased the 8×Gli BS-luciferase activity and co-expression of TAF9 with either Gli1 or Gli2 further increased the 8×Gli BS-luciferase activity to a significantly higher level than that by Gli alone, confirming that Gli1 and Gli2 specifically bound to the Gli-binding sites and were functionally active in transcription and that TAF9 may interact with Gli proteins as a co-activator. After treatment for 16-20 hours at 5 µM, Compound 4-enantiomer P2 was found to down-regulate both Gli alone and Gli/TAF9 induced 8×Gli BS-luciferase activities significantly in A549 cells. This result indicated that Compound 4-enantiomer P2 may be specific in inhibiting the interaction between Gli proteins and TAF9. FIG. 21 shows graphs of luciferase activity (%) showing that Gli inhibitor Compound 4-enantiomer P2 inhibits Gli/TAF dependent transcription activity in NCSLC cell line A549 in vitro.

Figure 22:
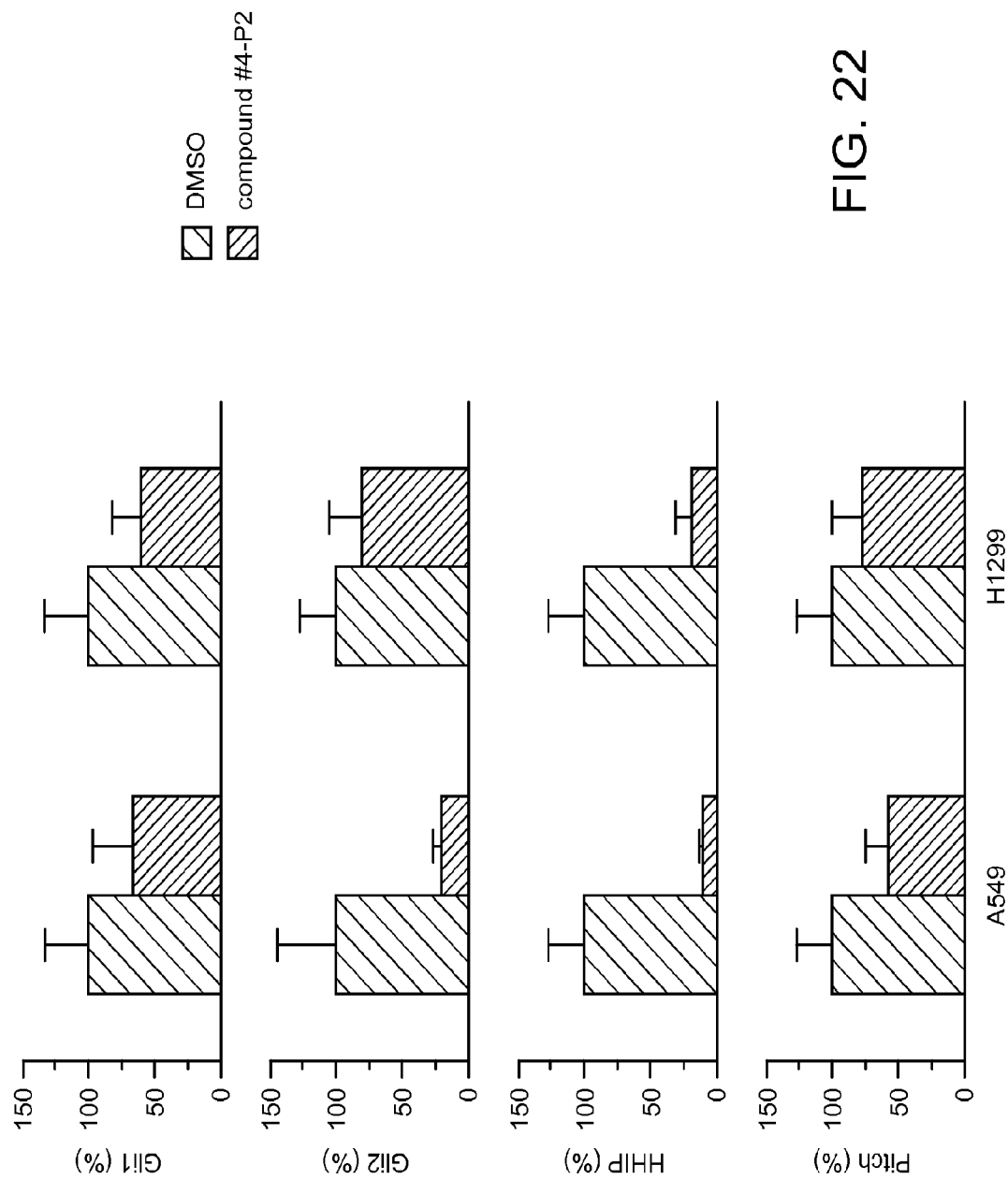
FIG. 22 shows graphs of expression levels of Gli downstream targets, which shows that Gli inhibitor Compound 4-enantiomer P2 inhibits Gli downstream targets in NSCLC cells in vitro, according to embodiments of the present disclosure.

Example 21: Gli Inhibitor Compound 4-Enantiomer P2 Inhibits Gli Downstream Targets in NSCLC Cells In Vitro Experiments were performed using real-time RT-PCR to analyze whether Compound 4-enantiomer P2 suppressed the lung cancer cell growth through inhibition of the Gli function. Total RNA was isolated from lung cancer cells (A549 and H1299) treated with Compound 4-enantiomer P2. The results indicated that expression levels of Gli downstream targets such as Gli1, Gli2, HHIP and Ptch1 were all significantly down-regulated by Compound 4-enantiomer P2 in those lung cancer cell lines. These results suggest that Compound 4-enantiomer P2 compound may specifically suppress lung cancer cell growth through inhibition of the Gli function. FIG. 22 shows graphs of expression levels of Gli downstream targets, which shows that Gli inhibitor Compound 4-enantiomer P2 inhibits Gli downstream targets in NSCLC cells in vitro.

Figure 23:
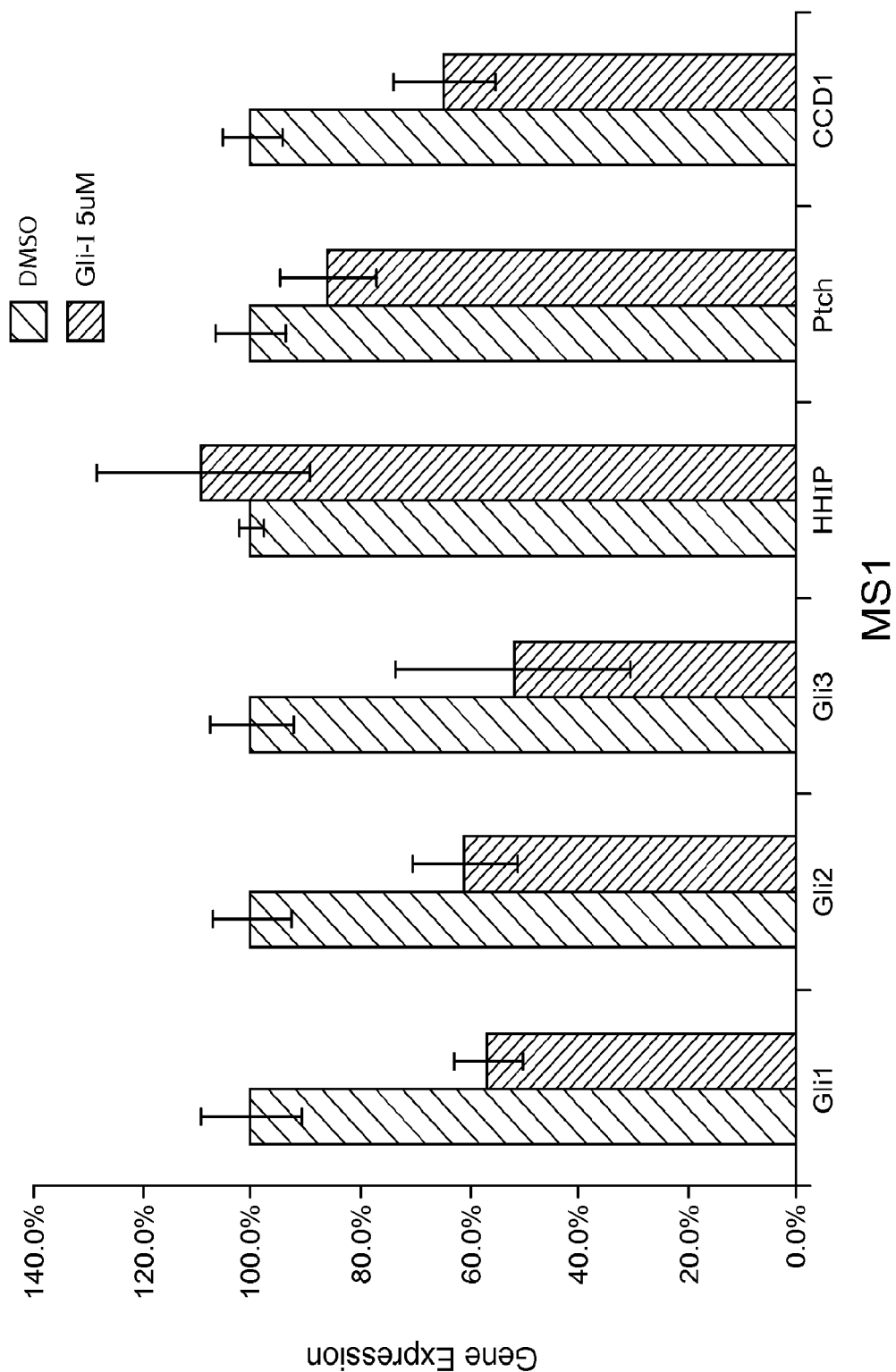
FIG. 23 shows graphs of gene expression showing that Gli inhibitor Compound 4-enantiomer P2 inhibits Gli downstream targets in mesothelioma cells in vitro, according to embodiments of the present disclosure.

Example 22: Gli Inhibitor Compound 4-Enentiomer P2 Inhibits Gli Downstream Targets in Mesothelioma Cells In Vitro Experiments were also performed using real-time RT-PCR to analyze whether Compound 4-enantiomer P2 suppressed the mesothelioma cell growth through inhibition of the Gli function. Total RNA was isolated from mesothelioma cells MS-1 treated with Compound 4-enantiomer P2 (5 uM). The results indicated that expression levels of Gli downstream targets such as Gli1, Gli2, HHIP and Ptch1, etc. were all significantly down-regulated by Compound 4-enantiomer P2 in those MS-1 cells. These results suggest that Compound 4-enantiomer P2 compound may specifically suppress mesothelioma cell growth through inhibition of the Gli function. FIG. 23 shows graphs of gene expression showing that Gli inhibitor Compound 4-enantiomer P2 inhibits Gli downstream targets in mesothelioma cells in vitro.

Example 23: Gli Inhibitor Compound 4-Enantiomer P2 Inhibits Gli Downstream Targets in Mesothelioma Cells in Tumors In Vivo (Mouse Xenograft Model: Mesothelioma MS-1)

Figure 24:
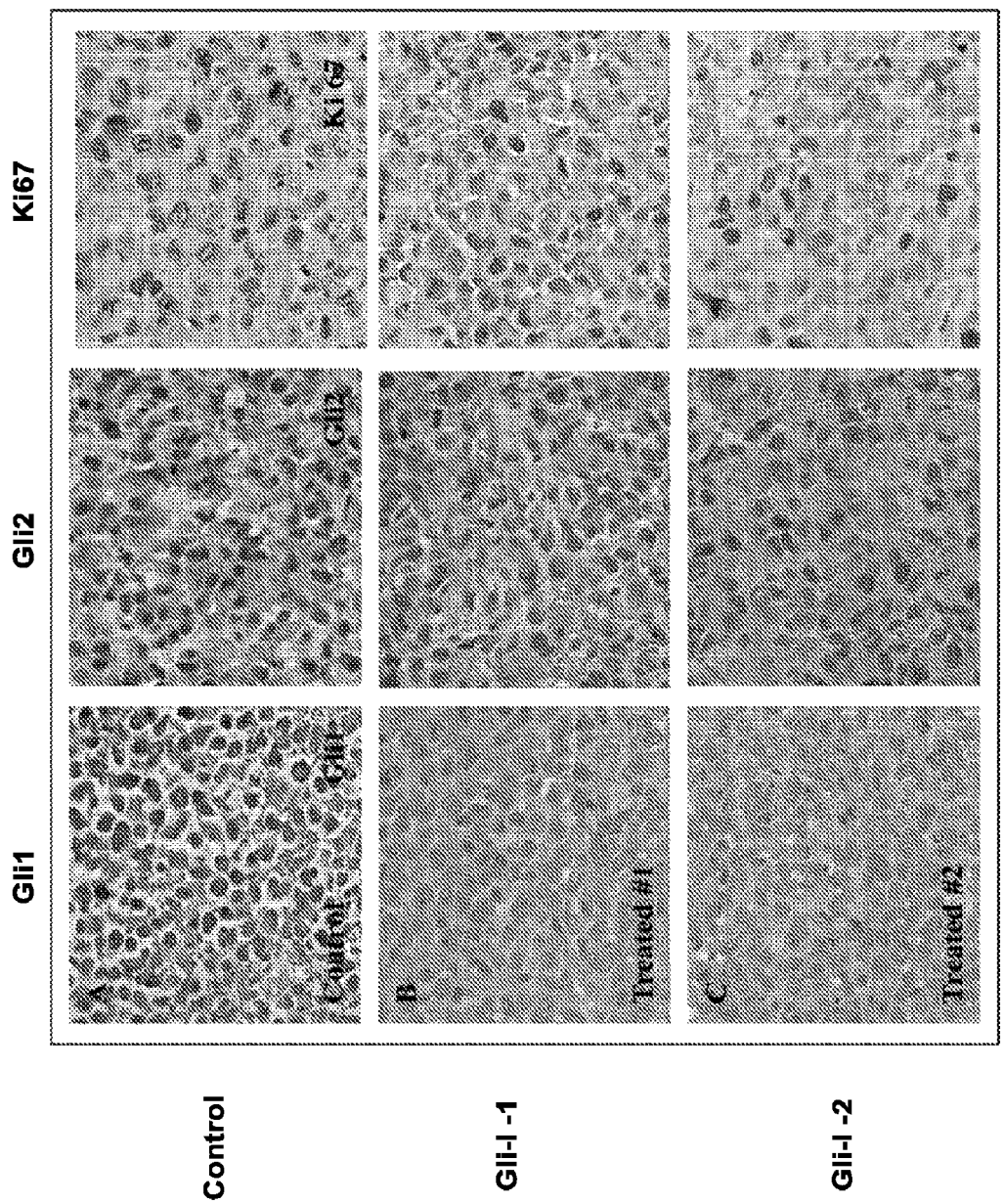
FIG. 24 shows immunohistochemistry images showing that Gli inhibitor Compound 4-enantiomer P2 inhibits Gli downstream targets in mesothelioma cells in tumors in vivo (mouse xenograft model: mesothelioma MS-1), according to embodiments of the present disclosure.

Experiments were performed using immunohistochemistry (IHC) to analyze whether Compound 4-enantiomer P2 suppressed the mesothelioma tumor growth through inhibition of the Gli function in vivo. The results indicated that protein expression levels of Gli1 and Gli2 were both significantly down-regulated by Compound 4-enantiomer P2 in those MS-1 tumors, consistent with the downregulation of a proliferation marker Ki-67 in those in vivo tumors. These results suggest that Compound 4-enantiomer P2 compound may specifically suppress mesothelioma tumor growth through inhibition of the Gli function in vivo. FIG. 24 shows immunohistochemistry images showing that Gli inhibitor Compound 4-enantiomer P2 inhibits Gli downstream targets in mesothelioma cells in tumors in vivo (mouse xenograft model: mesothelioma MS-1).

Figure 25:
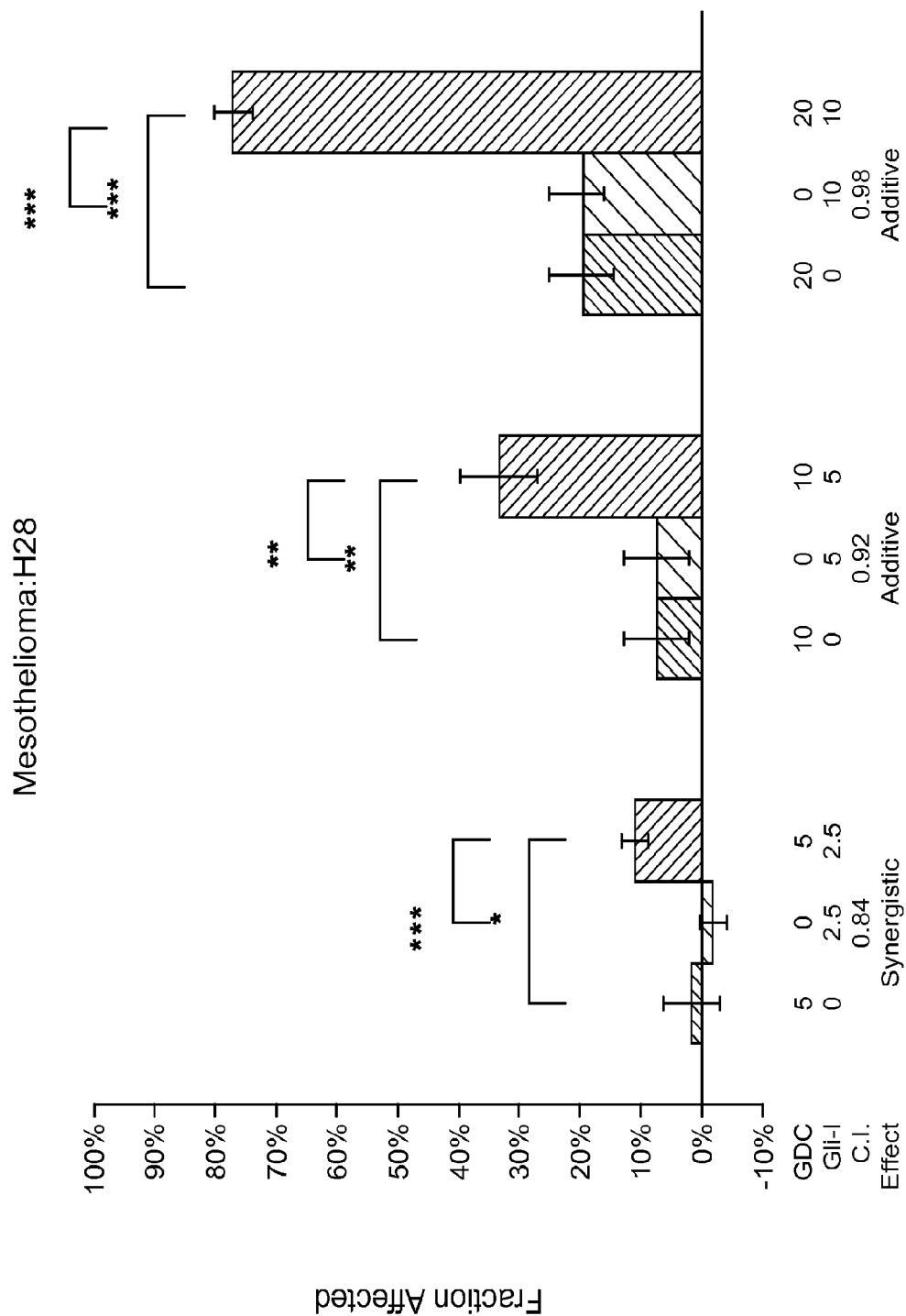
FIG. 25 shows graphs showing the synergistic effect of GDC0449 (Smo inhibitor) and the Gli inhibitor Compound 4-enantiomer P2 in suppressing growth of mesothelioma cells in vitro, according to embodiments of the present disclosure.

Example 24: Synergistic Effect of GDC0449 (Smo Inhibitor) and the Gli Inhibitor Compound 4-Enantiomer P2 in Suppressing Growth of Mesothelioma Cells In Vitro Experiments were performed to test the combination treatment of GDC0449 (Smo inhibitor) and Gli inhibitor Compound 4-enantiomer P2. A mesothelioma cell line H28 was treated by combining the Gli inhibitor Compound 4-enantiomer P2 and a Smo inhibitor GDC0449. The results indicated that the combination treatment synergistically or additively suppressed the proliferation of these mesothelioma cells. The CalcuSyn software (Biosoft) was used to calculate for each combination treatment in cancer cell lines with the Combination Index (CI) based on the Chou-Talalay method using the median effect equation to identify synergistic, additive, and antagonistic drug interactions. The CI values describe the effect of the combination effects of two compounds, where CI<1 indicates Synergism, CI=1 indicates Additive effects, and CI>1 indicates Antagonisim. Synergism is further defined as moderate synergism (CI=0.7-0.9), synergism (CI=0.3-0.7) and strong synergism (CI=0.1-0.3). FIG. 25 shows graphs showing the synergistic effect of GDC0449 (Smo inhibitor) and the Gli inhibitor Compound 4-enantiomer P2 in suppressing growth of mesothelioma cells in vitro.

Although the forgoing embodiments have been described in some detail by way of illustration and example for clarity and understanding, it will be readily apparent to one ordinary skill in the art in light of the teachings of this disclosure that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

As can be appreciated from the disclosure above, the present invention has a wide variety of applications. The invention is further illustrated by the examples above, which are only illustrative and are not intended to limit the definition and scope of the invention in any way.

What is claimed is:

1. An isolated enantiomer of a compound of formula (I):

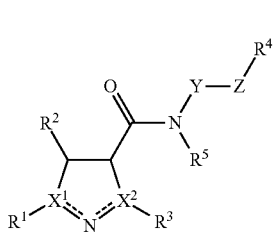

(I)

wherein
each of $X^1$ and $X^2$ is independently N or C, wherein one of $X^1$ and $X^2$ is N and one of $X^1$ and $X^2$ is C, such that the ring N forms a double bond with whichever of $X^1$ and $X^2$ is C;
$R^1$ is aryl or substituted aryl;
$R^2$ is selected from aryl, substituted aryl, heteroaryl, substituted heteroaryl, and alkyl;
$R^3$ is aryl or substituted aryl;
Y is a direct bond or $C_1$-$C_4$ alkyl;
Z is $C_1$-$C_4$ alkyl or aryl;
$R^4$ is —OH; and
$R^5$ is hydrogen or $C_1$-$C_6$ alkyl;
and salts and stereoisomers thereof.

2. The compound of claim 1, wherein the compound is a slower eluting enantiomer.

3. The compound of claim 1, wherein the compound is a faster eluting enantiomer.

4. The compound of claim 1, wherein $X^1$ is N and $X^2$ is C.

5. The compound of claim 1, wherein $R^1$ is aryl.

6. The compound of claim 1, wherein $R^2$ is alkyl.

7. The compound of claim 1, wherein $R^3$ is substituted aryl.

8. The compound of claim 1, wherein $R^5$ is hydrogen.

9. The compound of claim 1, wherein Y is $C_1$-$C_4$ alkyl and Z is $C_1$-$C_4$ alkyl.

10. The compound of claim 9, wherein Y is $C_1$-$C_4$ alkyl and Z is $C_1$-$C_4$ alkyl, such that Y and Z form —$(CH_2)_3$—$C(CH_3)_2$—$CH_2$—.

11. The compound of claim 1, wherein $R^1$ is aryl, $R^2$ is alkyl, and $R^3$ is substituted aryl.

12. The compound of claim 1, wherein the compound is

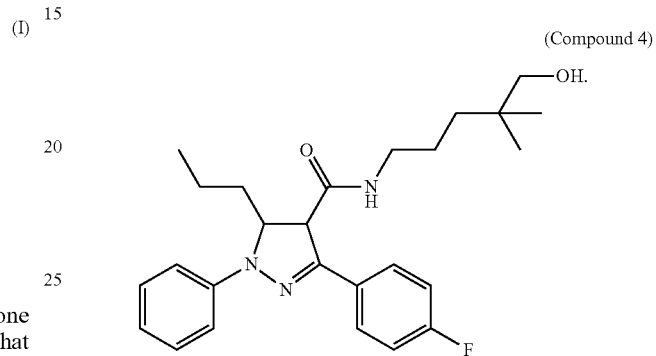

(Compound 4)

13. The compound of claim 12, wherein the compound is a slower eluting enantiomer.

14. The compound of claim 12, wherein the compound is a faster eluting enantiomer.

15. A pharmaceutical composition comprising:
(i) compound of claim 1; and
(ii) a pharmaceutically acceptable carrier.

16. A pharmaceutical composition comprising:
(i) compound of claim 1; and
(ii) a chemotherapeutic agent.

17. A pharmaceutical composition comprising:
(i) compound of claim 1; and
(ii) a therapeutic agent selected from erlotinib, pemetrexed, LY294002, SB431542, and cisplatin.

* * * * *